(12) United States Patent
Nicolaou et al.

(10) Patent No.: US 10,899,773 B2
(45) Date of Patent: Jan. 26, 2021

(54) TOTAL SYNTHESIS OF TRIOXACARCIN DC-45-A2 AND PREPARATION OF TRIOXACARCIN ANALOGS

(71) Applicant: WILLIAM MARSH RICE UNIVERSITY, Houston, TX (US)

(72) Inventors: Kyriacos C Nicolaou, Houston, TX (US); Quan Cai, Houston, TX (US)

(73) Assignee: William Marsh Rice University, Houston, TX (US)

( * ) Notice: Subject to any disclaimer, the term of this patent is extended or adjusted under 35 U.S.C. 154(b) by 119 days.

(21) Appl. No.: 15/537,319

(22) PCT Filed: Dec. 18, 2015

(86) PCT No.: PCT/US2015/066703
§ 371 (c)(1),
(2) Date: Jun. 16, 2017

(87) PCT Pub. No.: WO2016/100833
PCT Pub. Date: Jun. 23, 2016

(65) Prior Publication Data
US 2019/0023717 A1    Jan. 24, 2019

Related U.S. Application Data

(60) Provisional application No. 62/094,662, filed on Dec. 19, 2014, provisional application No. 62/186,128, filed on Jun. 29, 2015.

(51) Int. Cl.
*C07D 493/22* (2006.01)
*C07D 519/00* (2006.01)
(Continued)

(52) U.S. Cl.
CPC .......... *C07D 493/22* (2013.01); *A61K 31/357* (2013.01); *A61P 35/00* (2018.01); *C07D 491/22* (2013.01); *C07D 519/00* (2013.01)

(58) Field of Classification Search
CPC .. C07D 493/22; C07D 491/22; C07D 519/00; A61K 31/357; A61K 2300/00; A61P 35/00
(Continued)

(56) References Cited

U.S. PATENT DOCUMENTS 4,459,291 A    7/1984  Shirahata et al.
9,102,697 B2   8/2015  Myers et al.
(Continued)

FOREIGN PATENT DOCUMENTS

EP    0 157 203      10/1985
JP    S63 135389     6/1988
(Continued)

OTHER PUBLICATIONS

Svenda, J et al PNAS 2011 vol. 108 pp. 6709-6714.*
(Continued)

*Primary Examiner* — Taylor V Oh
(74) *Attorney, Agent, or Firm* — Parker Highlander PLLC

(57) ABSTRACT

In one aspect, the present invention provides novel derivatives of trioxacarin analogs of the formula (I) wherein the variables are as defined herein. The application also provides compositions, methods of treatment, and methods of synthesis thereof.

(Continued)

12 Claims, 4 Drawing Sheets

(51) Int. Cl.
 *A61K 31/357* (2006.01)
 *C07D 491/22* (2006.01)
 *A61P 35/00* (2006.01)
(58) Field of Classification Search
 USPC ........................................................ 549/432
 See application file for complete search history.

(56) References Cited

U.S. PATENT DOCUMENTS

| | | |
|---|---|---|
| 9,611,287 B2 | 4/2017 | Myers et al. |
| 2013/0150314 A1 | 6/2013 | Myers et al. |

FOREIGN PATENT DOCUMENTS

| | | |
|---|---|---|
| WO | WO 2011/119549 | 9/2011 |
| WO | WO 2014/082065 | 5/2014 |

OTHER PUBLICATIONS

Extended European Search Report issued in corresponding European Application No. 15871176.2, dated Sep. 19, 2018.
Fujimoto et al., "Antitumor Activity of Trioxacarcin C," *J. Antibiot.*, 36(9):1216-1221, 1983.
Cassidy et al., "Phase I clinical study of LL-D49194 alpha 1 with retrospective pharmacokinetic investigations in mice and humans. The EORTC ECTG." *Cancer Chemother. Pharmacol.* 1993, 31, 395-400.
Evans et al., "Synthetic studies in the lysocellin family of polyether antibiotics. The total synthesis of ferensimycin B." *J. Am. Chem. Soc.* 1991, 113, 7613-7630.
Fitzner et al., "Formation of gutingimycin: analytical investigation of trioxacarcin A-mediated alkylation of dsDNA." *Anal. Bioanal. Chem.* 2008, 390, 1139-1147.
Gaoni, "Reactions of γδ-unsaturated ketones with peracids. 2,7-Dioxabicyclo-[2,2,1]heptanes." *J. Chem. Soc. (C)* 1968, 2925-2934.
International Search Report and Written Opinion issued in International Application No. PCT/US2015/066703 dated Dec. 1, 2016.
International Preliminary Report on Patentability issued in International Application No. PCT/US2015/066703 dated Jun. 29, 2017.
Wasserman, et al., "Imine-epoxide rearrangements in the formation of substituted piperidines. A stereoselective synthesis of (±) solenopsin-A." *Tetrahedron Lett.* 1988b, 29, 4977-4980.
Maiese et al., "LL-D49194 Antibiotics, a Novel Family of Antitumor Agents: Taxonomy, Fermentation and Biological Properties. *J. Antibiot.*" 1990, 43, 253-258.
Maskey et al., "Anti-cancer and antibacterial trioxacarcins with high anti-malaria activity from a marine Streptomycete and their absolute stereochemistry." *J. Antibiot.* 2004, 57, 771-779.
Maskey et al., "Gutingimycin: a highly complex metabolite from a marine streptomycete." *Angew. Chem. Int. Ed.* 2004,43, 1281-1283.
Naruse et al., "Kinetic resolution of epoxides by chiral organoaluminum catalyst short synthesis of (−)–C16 juvenile hormone." *Tetrahedron* 1988a, 44, 4747-4756.
Naruse et al., "A new synthetic route to juvenile hormone kinetic resolution of epoxides using organoaluminum reagent." *Tetrahedron Lett.* 1988b, 29, 1417-1420.
Pfoh et al., "Crystal structure of trioxacarcin A covalently bound to DNA." *Nucleic Acids Res.* 2008, 36, 3508-3514.
Smith, et al., "DNA-Nogalamycin Interactions: The Crystal Structure of d(TGATCA) Complexed with Nogalamycin." *Biochemistry* 1995, 34, 415-425.
Sun, et al., Structure of the altromycin B (N7-guanine)-DNA adduct. A proposed prototypic DNA adduct structure for the pluramycin antitumor antibiotics. *Biochemistry* 1993, 32, 8068-8074.
Švenda et al., "A Multiply Convergent Platform for the Synthesis of Trioxacarcins." PNAS, vol. 108, pp. 6709-6714, 2011.
Tamaoki et al., "Trioxacarcins, Novel Antitumor Antibiotics Ii. Isolation, Physico-Chemical Properties and Mode of Action" *J. Antibiot.* 1981b, 34, 1525-1530.
Tomita, et al., I. Producing Organism, Fermentation and Biological ActivitieS. *J. Antibiot.* 1981a, 34, 1519-1524.
Wasserman, et al., *J. Am. Chem. Soc.* 1969, 91, 3674-3675.
Wasserman, et al., "Application of the carbonyl epoxide rearrangement to the formation of dioxabicycloalkanes and alkenes. Synthesis of the mus musculus pheromone. *Tetrahedron Lett.*"1986a, 27, 4909-4912.
Wasserman, et al., "The carbonyl epoxide rearrangement. A chiral synthesis of the mus musculus pheromone." *Tetrahedron Lett.* 1986b, 27, 4913-4916.
Wasserman, et al., "The carbonyl epoxide rearrangement. Epoxy imines in the formation of heterotropane derivatives." *Tetrahedron Lett.* 1988a, 29, 4973-4976.

\* cited by examiner

TOTAL SYNTHESIS OF TRIOXACARCIN DC-45-A2 AND PREPARATION OF TRIOXACARCIN ANALOGS

This present application is a national phase application under 35. U.S.C. § 371 of International Application No. PCT/US2015/066703, filed Dec. 18, 2015, and claims the benefit of priority to U.S. Provisional Application Ser. No. 62/094,662, filed on Dec. 19, 2014 and U.S. Provisional Application Ser. No. 62/186,128, filed Jun. 29, 2015, the entire contents of each of which are hereby incorporated by reference.

BACKGROUND

1. Field

This disclosure relates to the fields of medicine, pharmacology, chemistry, antimicrobial activity, and oncology. In particular, new compounds, compositions, methods of treatment, and methods of synthesis relating to trioxacarcin and derivatives thereof are disclosed.

2. Related Art

A group of natural products and synthetic derivatives thereof known as antitumor antibiotics are known to be powerful chemotherapeutics. These compounds have a variety of different mechanisms for their cytotoxicity, but often are associated with modification to the cellular DNA. Several commercial chemotherapeutics including actinomycin, bleomycin, daunorubicin, mitoxantrone, and doxorubicin fall within this class of compounds. One particular natural product, trioxacarcin DC-45-A2 (1, FIG. 1), is a naturally occurring antitumor antibiotic that serves as a biosynthetic precursor to a variety of other biologically active members of the family, including the highly potent DC-45-A1 (2), trioxacarcin A (3), and LL-D49194α1 (4) (FIG. 1) (Tomita et al., 1981; Tamaoki et al., 1981; Maiese et al., 1990; Maskey et al., 2004; Shirahata et al., 1984). The complex architecture with multiple oxygen containing functional groups and numerous stereocenters presents a difficult synthetic challenge limiting its commercial viability (Cassidy et al., 1993; Sun et al., 1994; Smith et al., 1995; Maskey et al., 2004; Fitzner et al., 2008; Pfoh et al., 2008). While originally these compounds were obtained by fermentation, several different synthetic routes have been developed (Gaoni, 1968; Waserman et al., 1969; Wasserman et al., 1986a; Wasserman et al., 1986b; Wasserman et al., 1988a; Wasserman et al., 1988b; Naruse et al., 1988a; Naruse et al., 1988b; Evans et al., 1991). Unfortunately, these methods are still relatively difficult and require numerous different steps to obtain the desired final product without allowing access to other derivatives. As such, analogs of trioxacarcin as well as an improved and modular synthesis method which allows for easier access to the natural product and analogs thereof are of commercial interest.

SUMMARY

Thus, there is provided compounds of the formula:

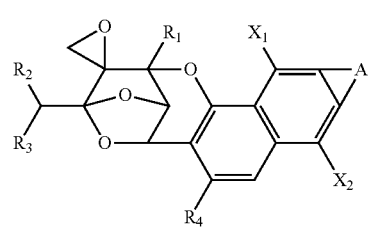

(I)

wherein: $R_1$ is amino, hydroxy, or mercapto; $alkoxy_{(C \leq 12)}$, $cycloalkoxy_{(C \leq 12)}$, $alkenyloxy_{(C \leq 12)}$, $alkynyloxy_{(C \leq 12)}$, $acyloxy_{(C \leq 12)}$, $alkylthio_{(C \leq 12)}$, $cycloalkylthio_{(C \leq 12)}$, $alkenylthio_{(C \leq 12)}$, $alkynylthio_{(C \leq 12)}$, $acylthio_{(C \leq 12)}$, $alkylamino_{(C \leq 12)}$, $cycloalkylamino_{(C \leq 12)}$, $alkenylamino_{(C \leq 12)}$, $alkynylamino_{(C \leq 12)}$, $dialkylamino_{(C \leq 12)}$, $dicycloalkylamino_{(C \leq 12)}$, $dialkenylamino_{(C \leq 12)}$, $dialkynylamino_{(C \leq 12)}$, $amido_{(C \leq 12)}$, or a substituted version of any of these groups; or $R_1$ is a group of the formula: $—O\text{-}alkanediyl_{(C \leq 8)}\text{-}alkoxy_{(C \leq 12)}$, $—O\text{-}alkanediyl_{(C \leq 8)}\text{-}alkenyloxy_{(C \leq 12)}$, $—O\text{-}alkanediyl_{(C \leq 8)}\text{-}alkynyloxy_{(C \leq 12)}$, or a substituted version thereof; or $R_1$ is a group of the formula:

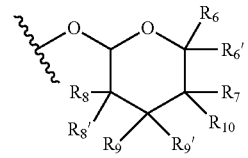

wherein: $R_6$, $R_6'$, $R_7$, $R_8$, $R_8'$, $R_9$, and $R_9'$ are each independently hydrogen, hydroxy, $alkyl_{(C \leq 8)}$, $alkoxy_{(C \leq 8)}$, $acyloxy_{(C \leq 8)}$, substituted $alkyl_{(C \leq 8)}$, substituted $alkoxy_{(C \leq 8)}$, or substituted $acyloxy_{(C \leq 8)}$; and $R_{10}$ is hydrogen, hydroxy, $alkyl_{(C \leq 12)}$, $alkoxy_{(C \leq 12)}$, $acyl_{(C \leq 12)}$, substituted $alkyl_{(C \leq 12)}$, substituted $alkoxy_{(C \leq 12)}$, substituted $acyl_{(C \leq 12)}$, or a group of the formula:

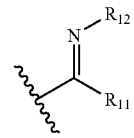

wherein: $R_{11}$ is hydrogen, $alkyl_{(C \leq 8)}$, or substituted $alkyl_{(C \leq 8)}$; and $R_{12}$ is hydrogen, hydroxy, $alkoxy_{(C \leq 12)}$, substituted $alkoxy_{(C \leq 12)}$, $—O\text{-}alkanediyl_{(C \leq 12)}$-a thiol reactive group, or a substituted version of $—O\text{-}alkanediyl_{(C \leq 12)}$-a thiol reactive group; or $R_7$ and $R_{10}$ are taken together to form a heterocyclic compound of the formula:

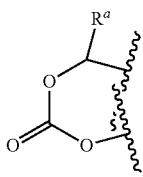

wherein: $R_a$ is hydrogen, alkyl$_{(C \leq 6)}$, or substituted alkyl$_{(C \leq 6)}$; $R_2$ and $R_3$ are independently hydrogen, amino, hydroxy, mercapto; alkyl$_{(C \leq 12)}$, cycloalkyl$_{(C \leq 12)}$, alkenyl$_{(C \leq 12)}$, alkynyl$_{(C \leq 12)}$, alkoxy$_{(C \leq 12)}$, cycloalkoxy$_{(C \leq 12)}$, alkenyloxy$_{(C \leq 12)}$, alkynyloxy$_{(C \leq 12)}$, alkylthio$_{(C \leq 12)}$, cycloalkylthio$_{(C \leq 12)}$, alkenylthio$_{(C \leq 12)}$, alkynylthio$_{(C \leq 12)}$, alkylamino$_{(C \leq 12)}$, cycloalkylamino$_{(C \leq 12)}$, alkenylamino$_{(C \leq 12)}$, alkynylamino$_{(C \leq 12)}$, or a substituted version of any of these groups; $R_2$ and $R_3$ are taken together and are alkoxydiyl$_{(C \leq 8)}$, alkylaminodiyl$_{(C \leq 12)}$, alkylthiodiyl$_{(C \leq 12)}$, or a substituted version of any of these groups; $R_4$ is hydrogen, amino, halo, hydroxy, mercapto, alkyl$_{(C \leq 12)}$ or substituted alkyl$_{(C \leq 12)}$; $X_1$ and $X_2$ are each independently hydrogen, hydroxy, or alkoxy$_{(C \leq 12)}$, alkenyloxy$_{(C \leq 12)}$, alkynyloxy$_{(C \leq 12)}$, or a substituted version of any of these groups; and A is a fused cycloalkanediyl and has the structure:

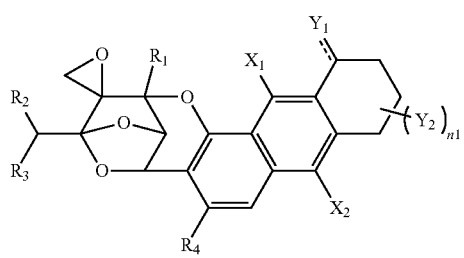

(Ia)

wherein: $Y_1$ is hydrogen, oxo, alkoxy$_{(C \leq 12)}$, or substituted alkoxy$_{(C \leq 12)}$, provided that when $Y_1$ is oxo, then the atom to which $Y_1$ is bound is part of a double bond, and provided that when the atom to which $Y_1$ is bound is part of a double bond, then $Y_1$ is oxo; $Y_2$ is hydrogen, hydroxy, alkyl$_{(C \leq 12)}$, substituted alkyl$_{(C \leq 12)}$, alkoxy$_{(C \leq 12)}$, substituted alkoxy$_{(C \leq 12)}$, or —$OX_3$, wherein $X_3$ is a hydroxy protecting group; or a group of the formula:

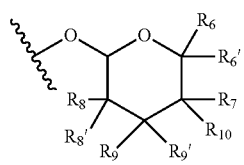

wherein: $R_6$, $R_6'$, $R_7$, $R_8$, $R_8'$, $R_9$, and $R_9'$ are each independently hydrogen, hydroxy, alkyl$_{(C \leq 8)}$, alkoxy$_{(C \leq 8)}$, acyloxy$_{(C \leq 8)}$, substituted alkyl$_{(C \leq 8)}$, substituted alkoxy$_{(C \leq 8)}$, or substituted acyloxy$_{(C \leq 8)}$; and $R_{10}$ is hydrogen, hydroxy, alkyl$_{(C \leq 12)}$, alkoxy$_{(C \leq 12)}$, acyl$_{(C \leq 12)}$, substituted alkyl$_{(C \leq 12)}$, substituted alkoxy$_{(C \leq 12)}$, substituted acyl$_{(C \leq 12)}$, or a group of the formula:

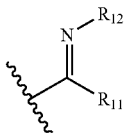

wherein: $R_{11}$ is hydrogen, alkyl$_{(C \leq 8)}$, or substituted alkyl$_{(C \leq 8)}$; and $R_{12}$ is hydrogen, hydroxy, alkoxy$_{(C \leq 12)}$, substituted alkoxy$_{(C \leq 12)}$, —O-alkanediyl$_{(C \leq 12)}$-a thiol reactive group, or a substituted version of —O-alkanediyl$_{(C \leq 12)}$-a thiol reactive group; or $R_7$ and $R_{10}$ are taken together to form a heterocyclic compound of the formula:

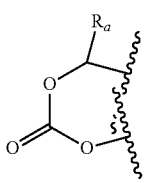

wherein: $R_a$ is hydrogen, alkyl$_{(C \leq 6)}$, or substituted alkyl$_{(C \leq 6)}$; and $n_1$ is 0, 1, 2, 3, 4, 5, or 6; or A is a fused arenediyl and has the structure:

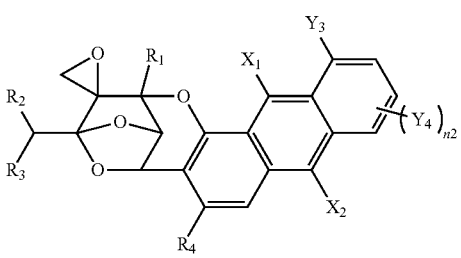

(Ib)

wherein: $Y_3$ is hydrogen, oxo, alkoxy$_{(C \leq 12)}$, or substituted alkoxy$_{(C \leq 12)}$, provided that when $Y_3$ is oxo, then the atom to which $Y_3$ is bound is part of a double bond, and provided that when the atom to which $Y_3$ is bound is part of a double bond, then $Y_3$ is oxo; $Y_4$ is hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —$OX_3$, wherein $X_3$ is a hydroxy protecting group, —$SX_4$, wherein $X_4$ is a thio protecting group, or —$NX_5X_6$, wherein either $X_5$ or $X_6$ is a monovalent amine protecting group and the other is a hydrogen or $X_5$ and $X_6$ are taken together and are a divalent amine protecting group; and $n_2$ is 0, 1, 2, or 3; or A is a fused arenediyl with a fused heterocycloalkanediyl and has the structure:

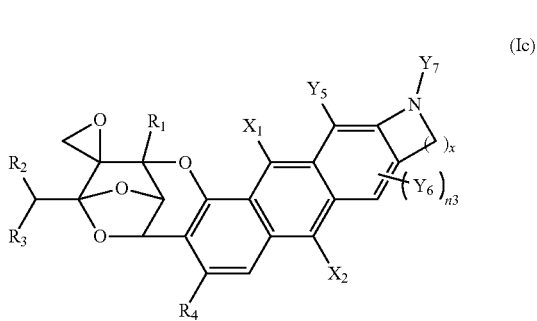

(Ic)

wherein: $Y_5$ is hydrogen, oxo, alkoxy$_{(C\leq12)}$, or substituted alkoxy$_{(C\leq12)}$, provided that when $Y_3$ is oxo, then the atom to which $Y_3$ is bound is part of a double bond, and provided that when the atom to which $Y_3$ is bound is part of a double bond, then $Y_3$ is oxo; $Y_6$ is hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein $X_3$ is a hydroxy protecting group, —SX$_4$, wherein $X_4$ is a thio protecting group, or —NX$_5$X$_6$, wherein either $X_5$ or $X_6$ is a monovalent amine protecting group and the other is a hydrogen or $X_5$ and $X_6$ are taken together and are a divalent amine protecting group; $Y_7$ is hydrogen, alkyl$_{(C\leq12)}$, or substituted alkyl$_{(C\leq12)}$; $n_3$ is 0 or 1; and x is 1, 2, 3, or 4; or A is a fused heteroarenediyl and has the structure:

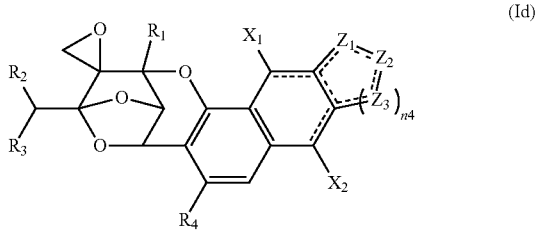

(Id)

wherein: $Z_1$, $Z_2$, and $Z_3$ are each independently selected from $CR_5R_5'$, $NR_5''$, O, or S; $R_5$ and $R_5'$ are each independently hydrogen, amino, hydroxy, halo, cyano, nitro, sulfato, sulfamido; alkyl$_{(C\leq6)}$, alkoxy$_{(C\leq6)}$, alkylamino$_{(C\leq6)}$, dialkylamino$_{(C\leq12)}$, amido$_{(C\leq6)}$, or a substituted version of any of these groups; and $R_5''$ is hydrogen, alkyl$_{(C\leq12)}$, or substituted alkyl$_{(C\leq12)}$; provided that at least one of $Z_1$, $Z_2$, or $Z_3$ is $NR_5''$, O, or S; $n_4$ is 1, 2, 3, or 4; or A is a fused arenediyl with a fused cycloalkanediyl and has the structure:

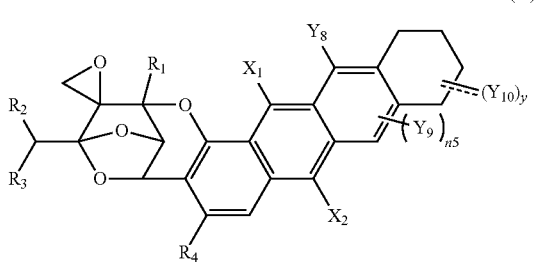

(Ie)

wherein: $Y_8$ and $Y_9$ are each independently selected from hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein $X_3$ is a hydroxy protecting group, —SX$_4$, wherein $X_4$ is a thio protecting group, or —NX$_5$X$_6$, wherein either $X_5$ or $X_6$ is a monovalent amine protecting group and the other is a hydrogen or $X_5$ and $X_6$ are taken together and are a divalent amine protecting group; $Y_{10}$ is hydrogen, oxo, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein $X_3$ is a hydroxy protecting group, —SX$_4$, wherein $X_4$ is a thio protecting group, or —NX$_5$X$_6$, wherein either $X_5$ or $X_6$ is a monovalent amine protecting group and the other is a hydrogen or $X_5$ and $X_6$ are taken together and are a divalent amine protecting group, provided that when $Y_3$ is oxo, then the atom to which $Y_3$ is bound is part of a double bond, and provided that when the atom to which $Y_3$ is bound is part of a double bond, then $Y_3$ is oxo; $n_5$ is 0 or 1; and y is 0, 1, 2, 3, 4, 5, 6, 7, or 8; A is a fused arenediyl and has the structure:

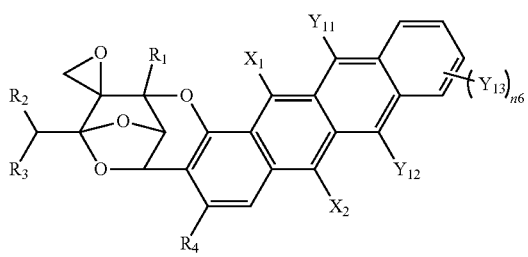

(If)

wherein: $Y_{11}$ and $Y_{12}$ are each independently selected from hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein $X_3$ is a hydroxy protecting group, —SX$_4$, wherein $X_4$ is a thio protecting group, or —NX$_5$X$_6$, wherein either $X_5$ or $X_6$ is a monovalent amine protecting group and the other is a hydrogen or $X_5$ and $X_6$ are taken together and are a divalent amine protecting group; $Y_{13}$ is hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein $X_3$ is a hydroxy protecting group, —SX$_4$, wherein $X_4$ is a thio protecting group, or —NX$_5$X$_6$, wherein either $X_5$ or $X_6$ is a monovalent amine protecting group and the other is a hydrogen or $X_5$ and $X_6$ are taken together and are a divalent amine protecting group, provided that when $Y_3$ is oxo, then the atom to which $Y_3$ is bound is part of a double bond, and provided that when the atom to which $Y_3$ is bound is part of a double bond, then $Y_3$ is oxo; and $n_6$ is 0, 1, 2, 3, or 4; provided that $R_1$ is not hydroxy and either $R_2$ or $R_3$ is methoxy when A is a fused cycloalkanediyl of the formula:

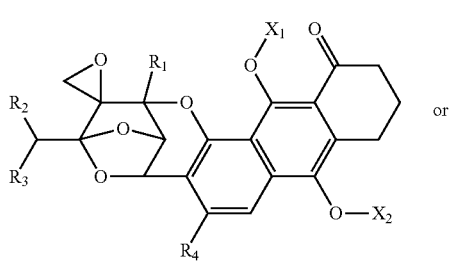

or

-continued

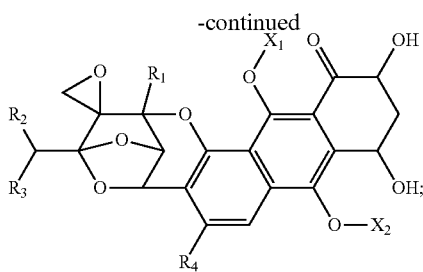

or a pharmaceutically acceptable salt thereof. In some embodiments, the compounds are further defined as:

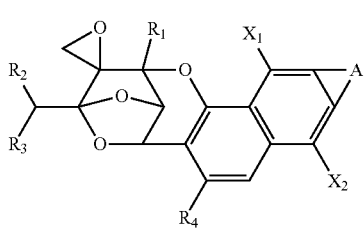

wherein: $R_1$ is amino, hydroxy, or mercapto; alkoxy$_{(C≤12)}$, cycloalkoxy$_{(C≤12)}$, alkenyloxy$_{(C≤12)}$, alkynyloxy$_{(C≤12)}$, acyloxy$_{(C≤12)}$, alkylthio$_{(C≤12)}$, cycloalkylthio$_{(C≤12)}$, alkenylthio$_{(C≤12)}$, alkynylthio$_{(C≤12)}$, acylthio$_{(C≤12)}$, alkylamino$_{(C≤12)}$, cycloalkylamino$_{(C≤12)}$, alkenylamino$_{(C≤12)}$, alkynylamino$_{(C≤12)}$, dialkylamino$_{(C≤12)}$, dicycloalkylamino$_{(C≤12)}$, dialkenylamino$_{(C≤12)}$, dialkynylamino$_{(C≤12)}$, amido$_{(C≤12)}$, or a substituted version of any of these groups; or $R_1$ is a group of the formula: —O-alkanediyl$_{(C≤8)}$-alkoxy$_{(C≤12)}$, —O-alkanediyl$_{(C≤8)}$-alkenyloxy$_{(C≤12)}$, —O-alkanediyl$_{(C≤8)}$-alkynyloxy$_{(C≤12)}$, or a substituted version thereof; or $R_1$ is a group of the formula:

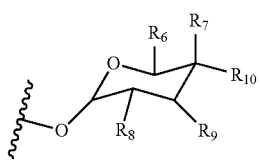

wherein: $R_6$, $R_7$, $R_8$, and $R_9$ are each independently hydrogen, hydroxy, alkyl$_{(C≤8)}$, alkoxy$_{(C≤8)}$, substituted alkyl$_{(C≤8)}$, or substituted alkoxy$_{(C≤8)}$; and $R_{10}$ is hydrogen, hydroxy, alkyl$_{(C≤12)}$, alkoxy$_{(C≤12)}$, acyl$_{(C≤12)}$, substituted alkyl$_{(C≤12)}$, substituted alkoxy$_{(C≤12)}$, substituted acyl$_{(C≤12)}$, or a group of the formula:

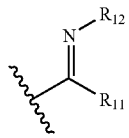

wherein: $R_{11}$ is hydrogen, alkyl$_{(C≤8)}$, or substituted alkyl$_{(C≤8)}$; and $R_{12}$ is hydrogen, hydroxy, alkoxy$_{(C≤12)}$, substituted alkoxy$_{(C≤12)}$, —O-alkanediyl$_{(C≤12)}$-a thiol reactive group, or a substituted version of —O-alkanediyl$_{(C≤12)}$-a thiol reactive group; $R_2$ and $R_3$ are independently selected from hydrogen, amino, hydroxy, mercapto; alkyl$_{(C≤12)}$, cycloalkyl$_{(C≤12)}$, alkenyl$_{(C≤12)}$, alkynyl$_{(C≤12)}$, alkoxy$_{(C≤12)}$, cycloalkoxy$_{(C≤12)}$, alkenyloxy$_{(C≤12)}$, alkynyloxy$_{(C≤12)}$, alkylthio$_{(C≤12)}$, cycloalkylthio$_{(C≤12)}$, alkenylthio$_{(C≤12)}$, alkynylthio$_{(C≤12)}$, alkylamino$_{(C≤12)}$, cycloalkylamino$_{(C≤12)}$, alkenylamino$_{(C≤12)}$, alkynylamino$_{(C≤12)}$, or a substituted version of any of these groups; $R_2$ and $R_3$ are taken together and are alkoxydiyl$_{(C≤8)}$, alkylaminodiyl$_{(C≤12)}$, alkylthiodiyl$_{(C≤12)}$, or a substituted version of any of these groups; $R_4$ is hydrogen, amino, halo, hydroxy, mercapto, alkyl$_{(C≤12)}$ or substituted alkyl$_{(C≤12)}$; $X_1$ and $X_2$ are each independently hydrogen, hydroxy, or alkoxy$_{(C≤12)}$, alkenyloxy$_{(C≤12)}$, alkynyloxy$_{(C≤12)}$, or a substituted version of any of these groups; and A is a fused cycloalkanediyl and has the structure:

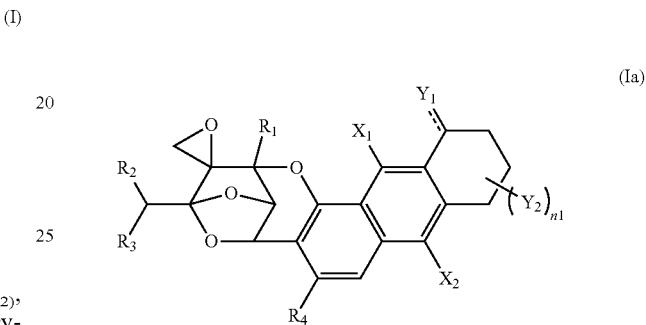

wherein: $Y_1$ is hydrogen, oxo, alkoxy$_{(C≤12)}$, or substituted alkoxy$_{(C≤12)}$, provided that when $Y_1$ is oxo, then the atom to which $Y_1$ is bound is part of a double bond, and provided that when the atom to which $Y_1$ is bound is part of a double bond, then $Y_1$ is oxo; $Y_2$ is hydrogen, hydroxy, alkoxy$_{(C≤12)}$, substituted alkoxy$_{(C≤12)}$, or —$OX_3$, wherein $X_3$ is a hydroxy protecting group; and $n_1$ is 0, 1, 2, 3, 4, 5, or 6; or A is a fused arenediyl and has the structure:

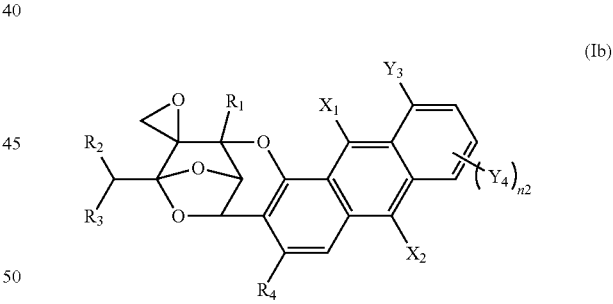

wherein: $Y_3$ is hydrogen, oxo, alkoxy$_{(C≤12)}$, or substituted alkoxy$_{(C≤12)}$, provided that when $Y_3$ is oxo, then the atom to which $Y_3$ is bound is part of a double bond, and provided that when the atom to which $Y_3$ is bound is part of a double bond, then $Y_3$ is oxo; $Y_4$ is hydrogen, hydroxy, amino, mercapto, alkoxy$_{(C≤12)}$, substituted alkoxy$_{(C≤12)}$, alkylthio$_{(C≤12)}$, substituted alkylthio$_{(C≤12)}$, alkylamino$_{(C≤12)}$, substituted alkylamino$_{(C≤12)}$, —$OX_3$, wherein $X_3$ is a hydroxy protecting group, —$SX_4$, wherein $X_4$ is a thio protecting group, or —$NX_5X_6$, wherein either $X_5$ or $X_6$ is a monovalent amine protecting group and the other is a hydrogen or $X_5$ and $X_6$ are taken together and are a divalent amine protecting group; and $n_2$ is 0, 1, 2, or 3; or A is a fused arenediyl with a fused heterocycloalkanediyl and has the structure:

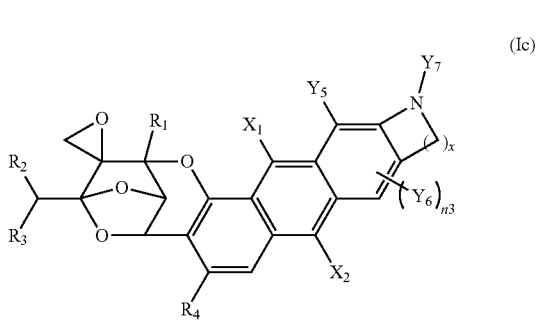

(Ic)

wherein: $Y_5$ is hydrogen, oxo, alkoxy$_{(C\leq12)}$, or substituted alkoxy$_{(C\leq12)}$, provided that when $Y_3$ is oxo, then the atom to which $Y_3$ is bound is part of a double bond, and provided that when the atom to which $Y_3$ is bound is part of a double bond, then $Y_3$ is oxo; $Y_6$ is hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group; $Y_7$ is hydrogen, alkyl$_{(C\leq12)}$, or substituted alkyl$_{(C\leq12)}$; $n_3$ is 0 or 1; and x is 1, 2, 3, or 4; or A is a fused heteroarenediyl and has the structure:

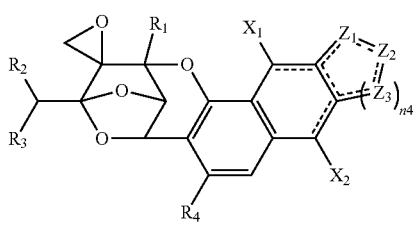

(Id)

wherein: $Z_1$, $Z_2$, and $Z_3$ are each independently selected from CR$_5$R$_5$', NR$_5$'', O, or S; R$_5$ and R$_5$' are each independently hydrogen, amino, hydroxy, halo, cyano, nitro, sulfato, sulfamido; alkyl$_{(C\leq6)}$, alkoxy$_{(C\leq6)}$, alkylamino$_{(C\leq6)}$, dialkylamino$_{(C\leq12)}$, amido$_{(C\leq6)}$, or a substituted version of any of these groups; and R$_5$'' is hydrogen, alkyl$_{(C\leq12)}$, or substituted alkyl$_{(C\leq12)}$; provided that at least one of Z$_1$, Z$_2$, or Z$_3$ is NR$_5$'', O, or S; $n_4$ is 1, 2, 3, or 4; or A is a fused arenediyl with a fused cycloalkanediyl and has the structure:

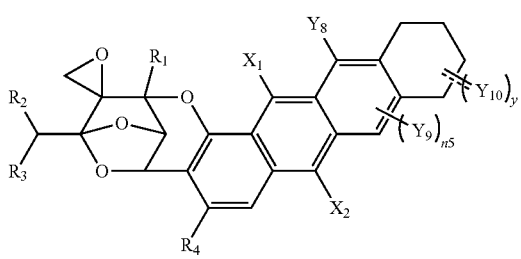

(Ie)

wherein: $Y_8$ and $Y_9$ are each independently selected from hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group; $Y_{10}$ is hydrogen, oxo, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group, provided that when Y$_3$ is oxo, then the atom to which Y$_3$ is bound is part of a double bond, and provided that when the atom to which Y$_3$ is bound is part of a double bond, then Y$_3$ is oxo; $n_5$ is 0 or 1; and y is 0, 1, 2, 3, 4, 5, 6, 7, or 8; A is a fused arenediyl and has the structure:

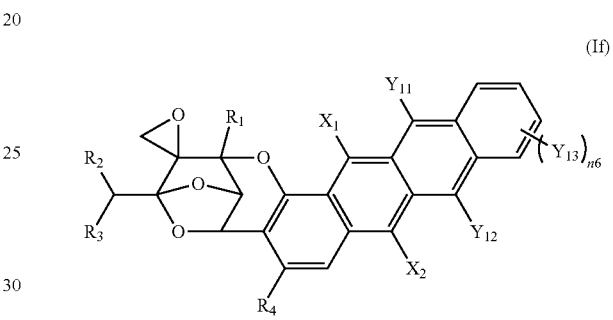

(If)

wherein: $Y_{11}$ and $Y_{12}$ are each independently selected from hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group; $Y_{13}$ is hydrogen, hydroxy, amino, mercapto, alkoxy$_{(C\leq12)}$, substituted alkoxy$_{(C\leq12)}$, alkylthio$_{(C\leq12)}$, substituted alkylthio$_{(C\leq12)}$, alkylamino$_{(C\leq12)}$, substituted alkylamino$_{(C\leq12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group, provided that when Y$_3$ is oxo, then the atom to which Y$_3$ is bound is part of a double bond, and provided that when the atom to which Y$_3$ is bound is part of a double bond, then Y$_3$ is oxo; and $n_6$ is 0, 1, 2, 3, or 4; provided that R$_1$ is not hydroxy and either R$_2$ or R$_3$ is methoxy when A is a fused cycloalkanediyl of the formula:

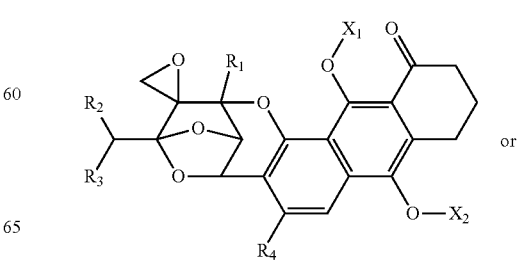

or

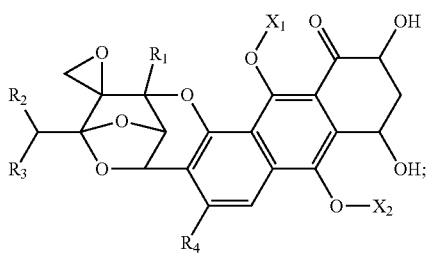

or a pharmaceutically acceptable salt thereof.

In some embodiments, the formula is further defined as Ia.
In some embodiments, the formula is further defined as Ib.
In some embodiments, the formula is further defined as Ic.
In some embodiments, the formula is further defined as Id.
In some embodiments, the formula is further defined as Ie.
In some embodiments, the formula is further defined as If.

The compound according to any one of claims 1-7, wherein $R_1$ is:

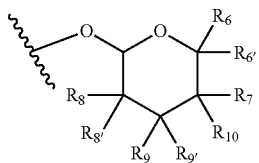

wherein: $R_6$, $R_6'$, $R_7$, $R_8$, $R_8'$, $R_9$, and $R_9'$ are each independently hydrogen, hydroxy, alkyl$_{(C\leq 8)}$, alkoxy$_{(C\leq 8)}$, acyloxy$_{(C\leq 8)}$, substituted alkyl$_{(C\leq 8)}$, substituted alkoxy$_{(C\leq 8)}$, or substituted acyloxy$_{(C\leq 8)}$; and $R_{10}$ is hydrogen, hydroxy, alkyl$_{(C\leq 12)}$, alkoxy$_{(C\leq 12)}$, acyl$_{(C\leq 12)}$, substituted alkyl$_{(C\leq 12)}$, substituted alkoxy$_{(C\leq 12)}$, substituted acyl$_{(C\leq 12)}$, or a group of the formula:

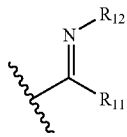

wherein: $R_{11}$ is hydrogen, alkyl$_{(C\leq 8)}$, or substituted alkyl$_{(C\leq 8)}$; and $R_{12}$ is hydrogen, hydroxy, alkoxy$_{(C\leq 12)}$, substituted alkoxy$_{(C\leq 12)}$, —O-alkanediyl$_{(C\leq 12)}$-a thiol reactive group, or a substituted version of —O-alkanediyl$_{(C\leq 12)}$-a thiol reactive group; or $R_7$ and $R_{10}$ are taken together to form a heterocyclic compound of the formula:

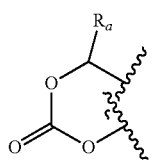

wherein: $R_a$ is hydrogen, alkyl$_{(C\leq 6)}$, or substituted alkyl$_{(C\leq 6)}$.
In some embodiments, $R_1$ is:

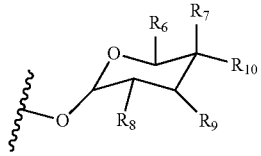

wherein: $R_6$, $R_7$, $R_8$, and $R_9$ are each independently hydrogen, hydroxy, alkyl$_{(C\leq 8)}$, alkoxy$_{(C\leq 8)}$, substituted alkyl$_{(C\leq 8)}$, or substituted alkoxy$_{(C\leq 8)}$; and $R_{10}$ is hydrogen, hydroxy, alkyl$_{(C\leq 12)}$, alkoxy$_{(C\leq 12)}$, acyl$_{(C\leq 12)}$, substituted alkyl$_{(C\leq 12)}$, substituted alkoxy$_{(C\leq 12)}$, substituted acyl$_{(C\leq 12)}$, or a group of the formula:

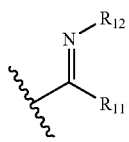

wherein: $R_{11}$ is hydrogen, alkyl$_{(C\leq 8)}$, or substituted alkyl$_{(C\leq 8)}$; and $R_{12}$ is hydrogen, hydroxy, alkoxy$_{(C\leq 12)}$, substituted alkoxy$_{(C\leq 12)}$, —O-alkanediyl$_{(C\leq 12)}$-a thiol reactive group, or a substituted version of —O-alkanediyl$_{(C\leq 12)}$-a thiol reactive group. In some embodiments, the thiol reactive group of $R_{12}$ is a maleimide. In other embodiments, $R_1$ is a group of the formula: —O-alkanediyl$_{(C\leq 8)}$-alkoxy$_{(C\leq 12)}$, —O-alkanediyl$_{(C\leq 8)}$-alkenyloxy$_{(C\leq 12)}$, —O-alkanediyl$_{(C\leq 8)}$-alkynyloxy$_{(C\leq 12)}$, or a substituted version thereof. In some embodiments, the alkanediyl$_{(C\leq 8)}$ of $R_1$ is —CH$_2$—. In other embodiments, $R_1$ is alkoxy$_{(C\leq 12)}$ or substituted alkoxy$_{(C\leq 12)}$. In some embodiments, $R_1$ is alkoxy$_{(C\leq 12)}$. In some embodiments, $R_1$ is substituted alkoxy$_{(C\leq 12)}$. In some embodiments, $R_1$ is —O(CH$_2$)$_6$OH or —OCH$_2$CH$_2$SH. In some embodiments, $R_1$ is alkynyloxy$_{(C\leq 12)}$ or substituted alkynyloxy$_{(C\leq 12)}$. In some embodiments, $R_1$ is alkynyloxy$_{(C\leq 12)}$. In some embodiments, $R_1$ is —CH$_2$C≡CH. In some embodiments, $R_1$ is alkylthio$_{(C\leq 12)}$ or substituted alkylthio$_{(C\leq 12)}$. In some embodiments, $R_1$ is alkylthio$_{(C\leq 12)}$. In some embodiments, $R_1$ is —SCH$_2$CH$_3$.

In some embodiments, $R_2$ is hydrogen. In some embodiments, $R_2$ is alkyl$_{(C\leq 12)}$ or substituted alkyl$_{(C\leq 12)}$. In some embodiments, $R_2$ is alkyl$_{(C\leq 12)}$. In some embodiments, $R_2$ is methyl. In some embodiments, $R_2$ is alkoxy$_{(C\leq 12)}$ or substituted alkoxy$_{(C\leq 12)}$. In some embodiments, $R_2$ is alkoxy$_{(C\leq 12)}$. In some embodiments, $R_2$ is methoxy. In some embodiments, $R_2$ is alkylthio$_{(C\leq 12)}$ or substituted alkylthio$_{(C\leq 12)}$. In some embodiments, $R_2$ is alkylthio$_{(C\leq 12)}$. In some embodiments, $R_2$ is —SCH$_3$.

In some embodiments, $R_2$ and $R_3$ are taken together and is alkoxydiyl$_{(C\leq 12)}$ or substituted alkoxydiyl$_{(C\leq 12)}$. In some embodiments, $R_2$ and $R_3$ are taken together and are alkoxydiyl$_{(C\leq 12)}$. In some embodiments, $R_2$ and $R_3$ are —OCH$_2$CH$_2$O—, —OCH$_2$CH$_2$CH$_2$O—, or —OCH$_2$C(CH$_3$)$_2$CH$_2$O—. In other embodiments, $R_2$ and $R_3$ are taken together and are alkoxydiyl$_{(C\leq 12)}$. In some embodiments, $R_2$ and $R_3$ are —OCH$_2$CH(CH$_2$OH)CH$_2$O—, —OCH$_2$CH(CH$_2$SH)CH$_2$O—, or —OCH$_2$CH(CH$_2$NHAc)CH$_2$O—. In other embodiments, $R_2$ and $R_3$ are taken together and is alkylthiodiyl$_{(C\leq 12)}$ or substituted alkylthiodiyl$_{(C\leq 12)}$. In some embodiments, $R_2$ and $R_3$ are taken together and are alkylthiodiyl$_{(C\leq 12)}$. In some embodiments, $R_2$ and $R_3$ are —SCH$_2$CH$_2$CH$_2$S— or —SCH$_2$C(CH$_3$)$_2$CH$_2$S—.

In some embodiments, $R_3$ is hydrogen. In some embodiments, $R_3$ is alkyl$_{(C\leq12)}$ or substituted alkyl$_{(C\leq12)}$. In some embodiments, $R_3$ is alkyl$_{(C\leq12)}$. In some embodiments, $R_3$ is methyl. In some embodiments, $R_3$ is alkoxy$_{(C\leq12)}$ or substituted alkoxy$_{(C\leq12)}$. In some embodiments, $R_3$ is alkoxy$_{(C\leq12)}$. In some embodiments, $R_3$ is methoxy. In some embodiments, $R_3$ is alkylthio$_{(C\leq12)}$ or substituted alkylthio$_{(C\leq12)}$. In some embodiments, $R_3$ is alkylthio$_{(C\leq12)}$. In some embodiments, $R_3$ is —SCH$_3$.

In some embodiments, $R_4$ is halo. In some embodiments, $R_4$ is fluoro, chloro, or bromo. In some embodiments, $R_4$ is fluoro. In some embodiments, $R_4$ is alkyl$_{(C\leq12)}$ or substituted alkyl$_{(C\leq12)}$. In some embodiments, $R_4$ is alkyl$_{(C\leq12)}$. In some embodiments, $R_4$ is methyl. In some embodiments, $R_4$ is substituted alkyl$_{(C\leq12)}$. In some embodiments, $R_4$ is trifluoromethyl.

In some embodiments, $X_1$ is hydrogen. In some embodiments, $X_1$ is hydroxy. In some embodiments, $X_1$ is alkoxy$_{(C\leq12)}$ or substituted alkoxy$_{(C\leq12)}$. In some embodiments, $X_1$ is alkoxy$_{(C\leq12)}$. In some embodiments, $X_1$ is methoxy. In other embodiments, $X_1$ is substituted alkoxy$_{(C\leq12)}$. In some embodiments, $X_1$ is —O(CH$_2$)$_3$NH$_2$, —O(CH$_2$)$_2$C(O)NH$_2$, or —O(CH$_2$)$_3$SH. In other embodiments, $X_1$ is alkenyloxy$_{(C\leq12)}$. In some embodiments, $X_1$ is —OCH$_2$CHCH$_2$. In other embodiments, $X_1$ is alkynyloxy$_{(C\leq12)}$. In some embodiments, $X_1$ is —OCH$_2$CCH.

In some embodiments, $X_2$ is hydrogen. In some embodiments, $X_2$ is hydroxy. In some embodiments, $X_2$ is alkoxy$_{(C\leq12)}$ or substituted alkoxy$_{(C\leq12)}$. In some embodiments, $X_2$ is alkoxy$_{(C\leq12)}$. In some embodiments, $X_2$ is methoxy.

In some embodiments, $Y_1$ is oxo. In some embodiments, $Y_2$ is hydrogen. In some embodiments, $Y_2$ is hydroxy. In some embodiments, 76.1. The compound according to any one of claim 1-2 or 12-74, wherein $Y_2$ is:

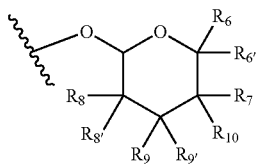

wherein: $R_6$, $R_6'$, $R_7$, $R_8$, $R_8'$, $R_9$, and $R_9'$ are each independently hydrogen, hydroxy, alkyl$_{(C\leq8)}$, alkoxy$_{(C\leq8)}$, acyloxy$_{(C\leq8)}$, substituted alkyl$_{(C\leq8)}$, substituted alkoxy$_{(C\leq8)}$, or substituted acyloxy$_{(C\leq8)}$; and $R_{10}$ is hydrogen, hydroxy, alkyl$_{(C\leq12)}$, alkoxy$_{(C\leq12)}$, acyl$_{(C\leq12)}$, substituted alkyl$_{(C\leq12)}$, substituted alkoxy$_{(C\leq12)}$, substituted acyl$_{(C\leq12)}$, or a group of the formula:

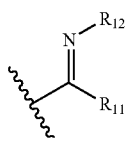

wherein: $R_{11}$ is hydrogen, alkyl$_{(C\leq8)}$, or substituted alkyl$_{(C\leq8)}$; and $R_{12}$ is hydrogen, hydroxy, alkoxy$_{(C\leq12)}$, substituted alkoxy$_{(C\leq12)}$, —O-alkanediyl$_{(C\leq12)}$-a thiol reactive group, or a substituted version of —O-alkanediyl$_{(C\leq12)}$-a thiol reactive group; or $R_7$ and $R_{10}$ are taken together to form a heterocyclic compound of the formula:

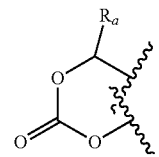

wherein: $R_a$ is hydrogen, alkyl$_{(C\leq6)}$, or substituted alkyl$_{(C\leq6)}$. In some embodiments, $Y_2$ is:

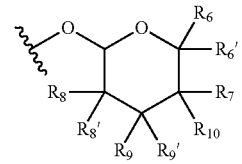

wherein: $R_6$, $R_6'$, $R_7$, $R_8$, $R_8'$, $R_9$, and $R_9'$ are each independently hydrogen, hydroxy, alkyl$_{(C\leq8)}$, alkoxy$_{(C\leq8)}$, acyloxy$_{(C\leq8)}$, substituted alkyl$_{(C\leq8)}$, substituted alkoxy$_{(C\leq8)}$, or substituted acyloxy$_{(C\leq8)}$; and $R_{10}$ is hydrogen, hydroxy, alkyl$_{(C\leq12)}$, alkoxy$_{(C\leq12)}$, acyloxy$_{(C\leq12)}$, acyl$_{(C\leq12)}$, substituted alkyl$_{(C\leq12)}$, substituted alkoxy$_{(C\leq12)}$, substituted acyloxy$_{(C\leq12)}$, or substituted acyl$_{(C\leq12)}$. In some embodiments, $Y_2$ is:

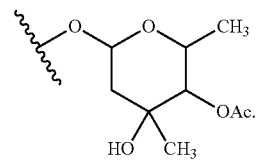 [SMILES: *OC1CC(C)(O)C(OC(C)=O)C(C)O1]

In some embodiments, $n_1$ is 0, 1, 2, or 3. In some embodiments, $n_1$ is 0, 1, or 2.

In some embodiments, $Y_3$ is hydroxy. In some embodiments, $Y_3$ is alkoxy$_{(C\leq12)}$ or substituted alkoxy$_{(C\leq12)}$. In some embodiments, $Y_3$ is alkoxy$_{(C\leq12)}$. In some embodiments, $Y_3$ is methoxy. In some embodiments, $Y_3$ is substituted alkoxy$_{(C\leq12)}$. In some embodiments, $Y_3$ is methoxymethoxy. In some embodiments, $Y_4$ is hydrogen. In some embodiments, $Y_4$ is hydroxy. In some embodiments, $Y_4$ is alkoxy$_{(C\leq12)}$ or substituted alkoxy$_{(C\leq12)}$. In some embodiments, $Y_4$ is alkoxy$_{(C\leq12)}$. In some embodiments, $Y_4$ is methoxy. In some embodiments, $Y_4$ is alkylamino$_{(C\leq12)}$ or substituted alkylamino$_{(C\leq12)}$. In some embodiments, $Y_4$ is alkylamino$_{(C\leq12)}$. In some embodiments, $Y_4$ is methylamino. In some embodiments, $n_2$ is 1, 2, or 3.

In some embodiments, $Y_5$ is hydroxy. In some embodiments, $Y_5$ is alkoxy$_{(C\leq12)}$ or substituted alkoxy$_{(C\leq12)}$. In some embodiments, $Y_5$ is alkoxy$_{(C\leq12)}$. In some embodiments, $Y_5$ is methoxy. In some embodiments, $Y_6$ is hydrogen. In some embodiments, $Y_6$ is hydroxy. In some embodiments, $Y_6$ is alkoxy$_{(C\leq12)}$ or substituted alkoxy$_{(C\leq12)}$. In some embodiments, $Y_6$ is alkoxy$_{(C\leq12)}$. In some embodiments, $Y_6$ is methoxy. In some embodiments, $Y_7$ is hydrogen. In some embodiments, $Y_7$ is alkyl$_{(C\leq6)}$ or substituted alkyl$_{(C\leq6)}$. In some embodiments, x is 2 or 3. In some embodiments, x is 2. In some embodiments, x is 3. In some embodiments, $n_3$ is 0. In some embodiments, $n_3$ is 1.

In some embodiments, $Z_1$ is S. In some embodiments, $Z_1$ is N. In some embodiments, $Z_1$ is O. In some embodiments, $Z_2$ is S. In some embodiments, $Z_2$ is N. In some embodiments, $Z_2$ is O. In some embodiments, $Z_2$ is $CR_5''$. In some embodiments, $R_5''$ is hydrogen, hydroxy, halo, $alkyl_{(C≤12)}$, substituted $alkyl_{(C≤12)}$, $alkoxy_{(C≤12)}$, or substituted $alkoxy_{(C≤12)}$. In some embodiments, $R_5''$ is hydrogen. In some embodiments, $R_5''$ is $alkoxy_{(C≤12)}$ or substituted $alkoxy_{(C≤12)}$. In some embodiments, $R_5''$ is methoxy. In some embodiments, $R_5''$ is $alkyl_{(C≤12)}$ or substituted $alkyl_{(C≤12)}$. In some embodiments, $R_5''$ is methyl. In some embodiments, $Z_3$ is S. In some embodiments, $Z_3$ is N. In some embodiments, $Z_3$ is O. In some embodiments, $Z_3$ is $CR_5''$. In some embodiments, $R_5''$ is hydrogen, hydroxy, halo, $alkyl_{(C≤12)}$, substituted $alkyl_{(C≤12)}$, $alkoxy_{(C≤12)}$, or substituted $alkoxy_{(C≤12)}$. In some embodiments, $R_5''$ is hydrogen. In some embodiments, $R_5''$ is $alkoxy_{(C≤12)}$ or substituted $alkoxy_{(C≤12)}$. In some embodiments, $R_5''$ is methoxy. In some embodiments, $R_5''$ is $alkyl_{(C≤12)}$ or substituted $alkyl_{(C≤12)}$. In some embodiments, $R_5''$ is methyl. In some embodiments, $n_4$ is 1, 2, or 3.

In some embodiments, $Y_8$ is hydrogen. In some embodiments, $Y_8$ is hydroxy. In some embodiments, $Y_8$ is $alkoxy_{(C≤12)}$ or substituted $alkoxy_{(C≤12)}$. In some embodiments, $Y_8$ is $alkoxy_{(C≤12)}$. In some embodiments, $Y_8$ is methoxy. In some embodiments, $Y_9$ is hydrogen. In some embodiments, $Y_9$ is hydroxy. In some embodiments, $Y_9$ is $alkoxy_{(C≤12)}$ or substituted $alkoxy_{(C≤12)}$. In some embodiments, $Y_9$ is $alkoxy_{(C≤12)}$. In some embodiments, $Y_9$ is methoxy. In some embodiments, $Y_{10}$ is hydrogen. In some embodiments, $Y_{10}$ is hydroxy. In some embodiments, $Y_{10}$ is oxo. In some embodiments, $Y_{10}$ is $alkoxy_{(C≤12)}$ or substituted $alkoxy_{(C≤12)}$. In some embodiments, $Y_{10}$ is $alkoxy_{(C≤12)}$. In some embodiments, $Y_{10}$ is methoxy. In some embodiments, $Y_{10}$ is $alkylamino_{(C≤12)}$ or substituted $alkylamino_{(C≤12)}$. In some embodiments, $Y_{10}$ is $alkylamino_{(C≤12)}$. In some embodiments, $Y_{10}$ is methylamino. In some embodiments, $n_5$ is 1. In some embodiments, y is 1, 2, 3, 4, 5, or 6.

In some embodiments, $Y_{11}$ is hydrogen. In some embodiments, $Y_{11}$ is hydroxy. In some embodiments, $Y_{11}$ is $alkoxy_{(C≤12)}$ or substituted $alkoxy_{(C≤12)}$. In some embodiments, $Y_{11}$ is $alkoxy_{(C≤12)}$. In some embodiments, $Y_{11}$ is methoxy. In some embodiments, $Y_{12}$ is hydrogen. In some embodiments, $Y_{12}$ is hydroxy. In some embodiments, $Y_{12}$ is $alkoxy_{(C≤12)}$ or substituted $alkoxy_{(C≤12)}$. In some embodiments, $Y_{12}$ is $alkoxy_{(C≤12)}$. In some embodiments, $Y_{12}$ is methoxy. In some embodiments, $Y_{13}$ is hydrogen. In some embodiments, $Y_{13}$ is hydroxy. In some embodiments, $Y_{13}$ is oxo. In some embodiments, $Y_{13}$ is $alkoxy_{(C≤12)}$ or substituted $alkoxy_{(C≤12)}$. In some embodiments, $Y_{13}$ is $alkoxy_{(C≤12)}$. In some embodiments, $Y_{13}$ is methoxy. In some embodiments, $Y_{13}$ is $alkylamino_{(C≤12)}$ or substituted $alkylamino_{(C≤12)}$. In some embodiments, $Y_{13}$ is $alkylamino_{(C≤12)}$. In some embodiments, $Y_{13}$ is methylamino. In some embodiments, $n_6$ is 1, 2, or 3. In some embodiments, $n_6$ is 2 or 3.

In some embodiments, the compound is further defined as:

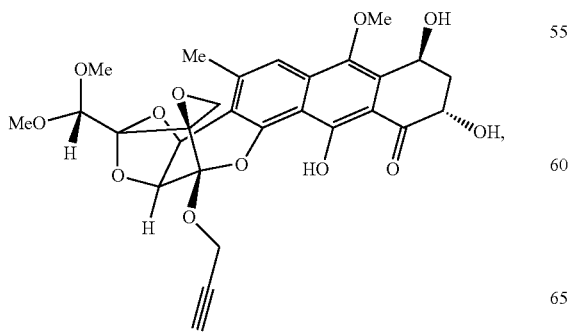

-continued

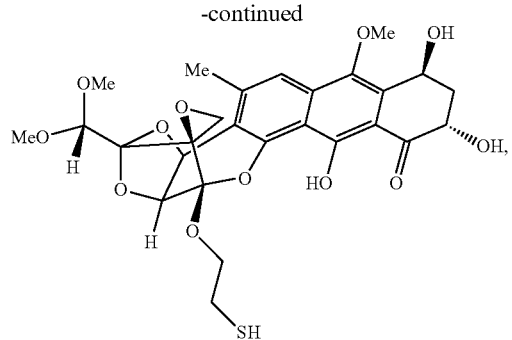

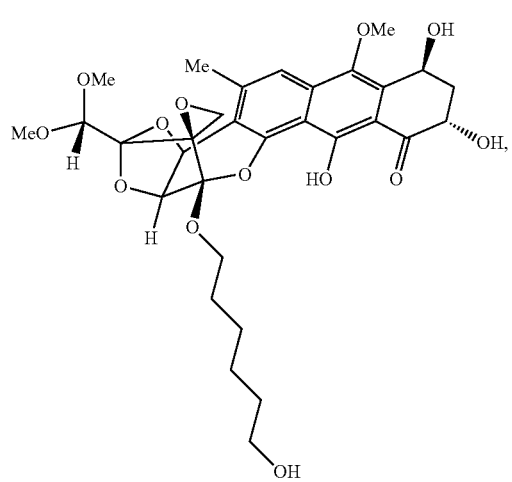

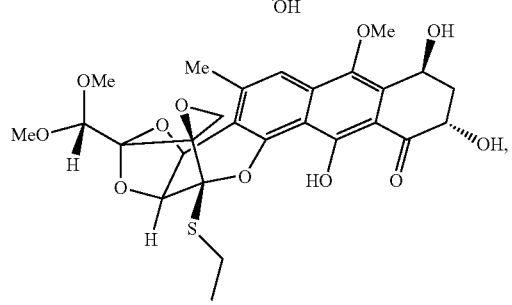

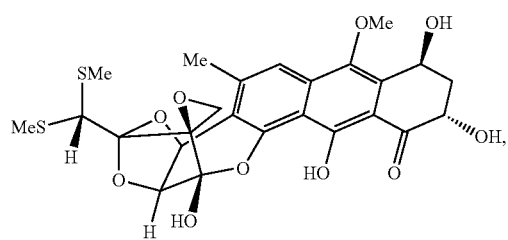

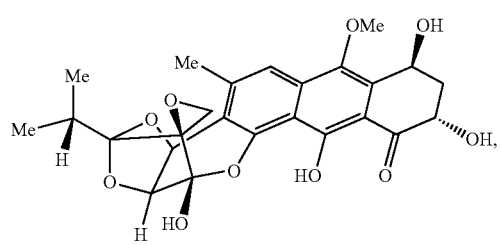

-continued
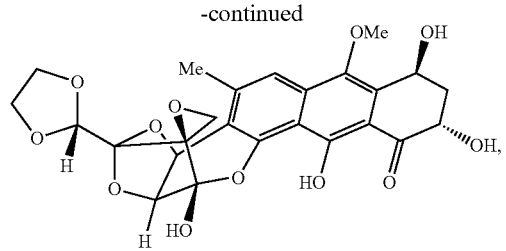
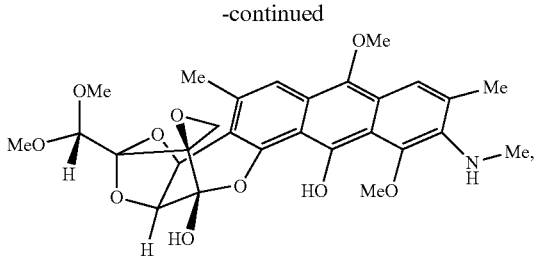
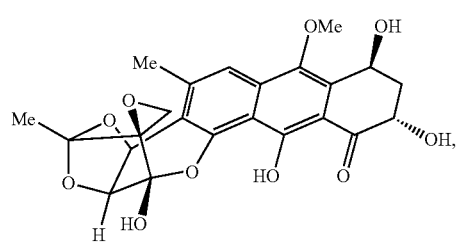
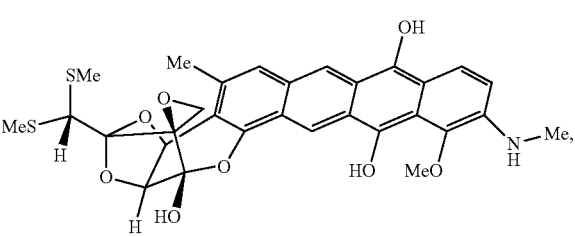
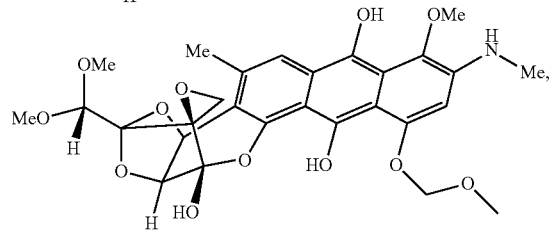
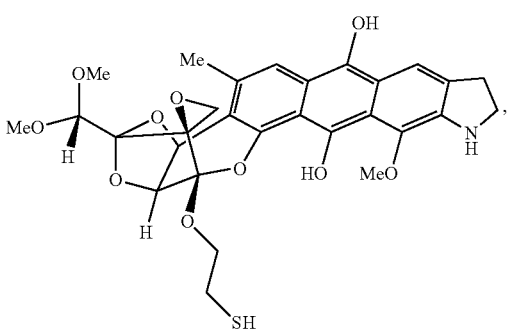
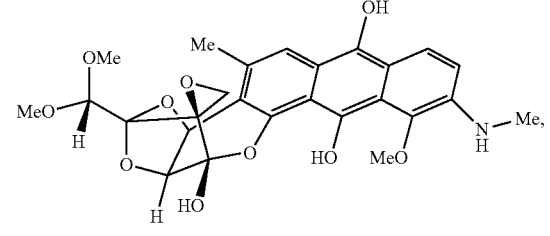
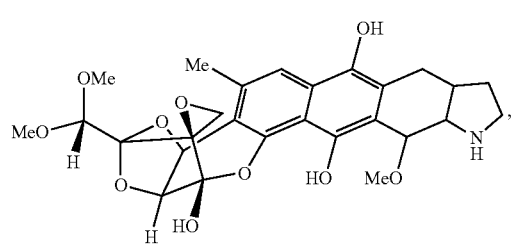
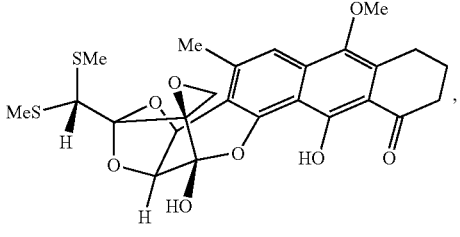
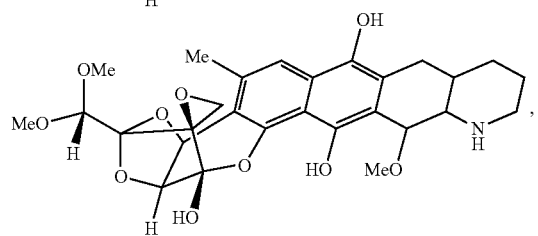
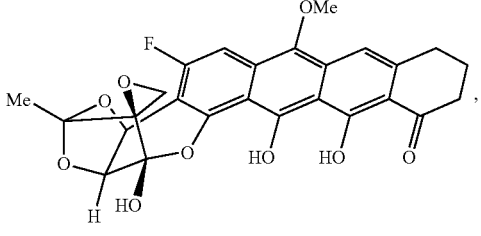
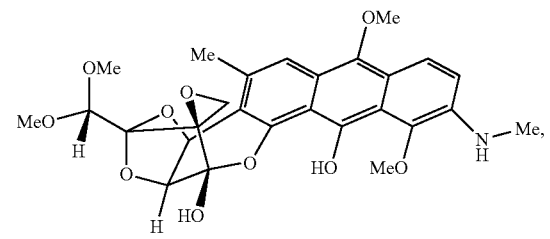
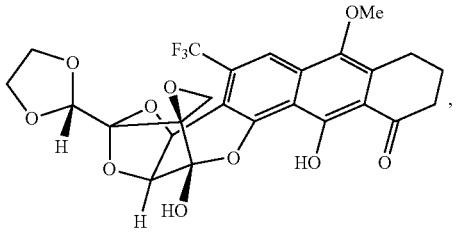

-continued
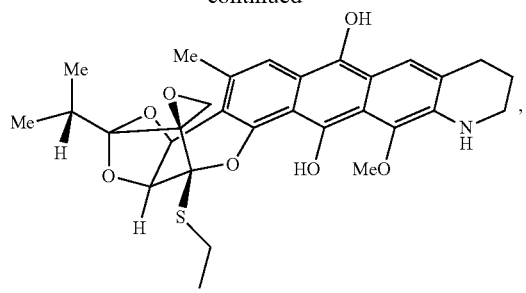
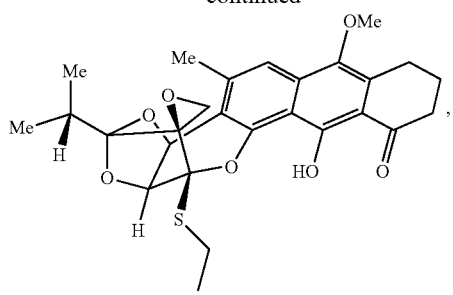
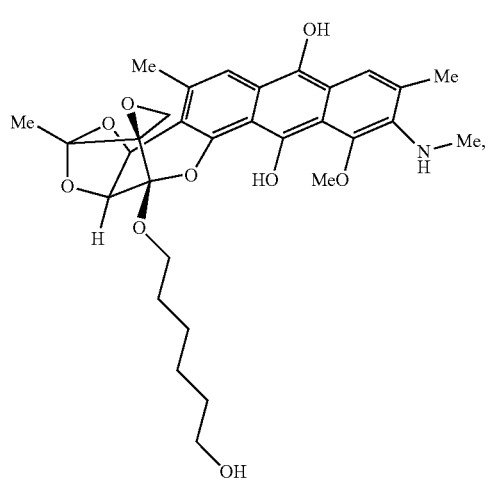
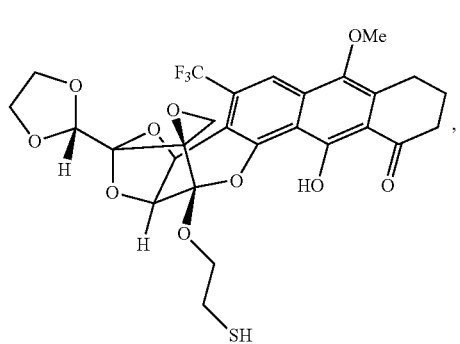
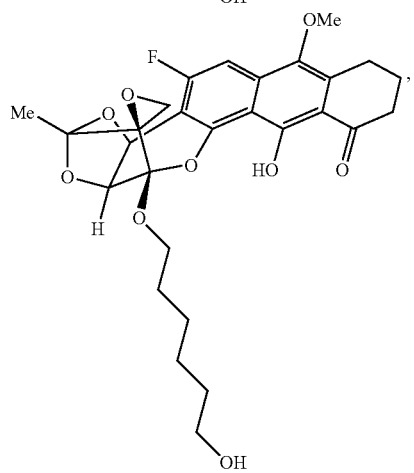
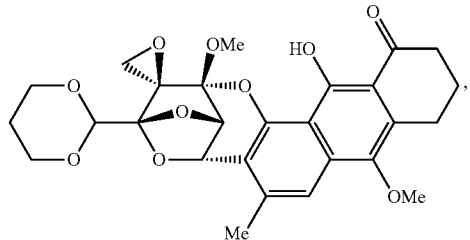
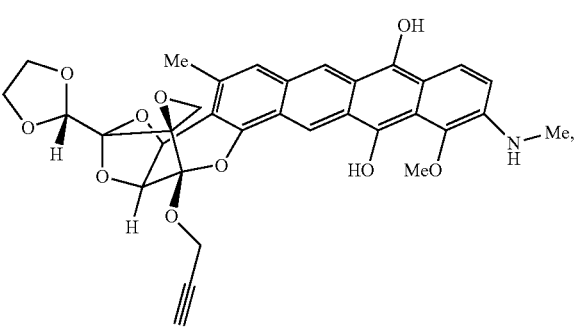
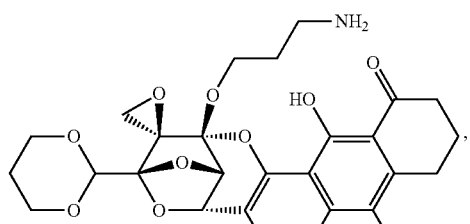
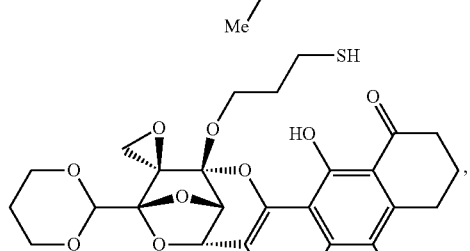

21
-continued
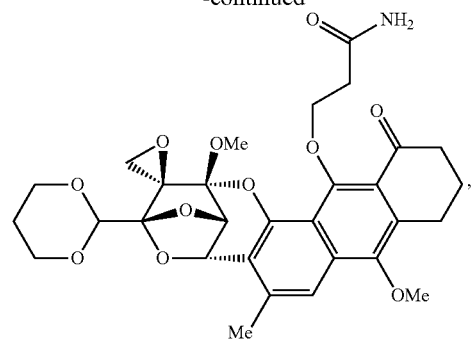
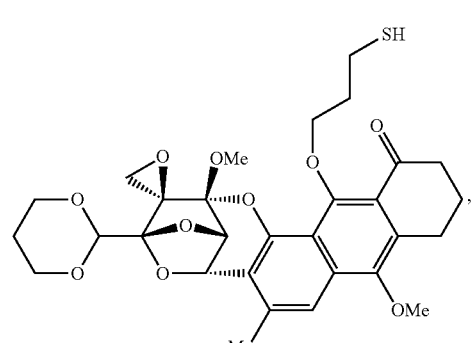
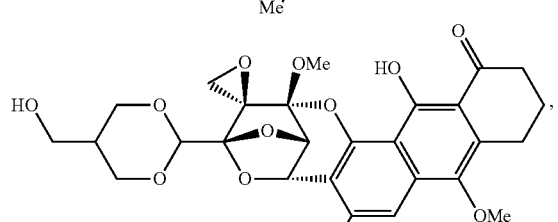
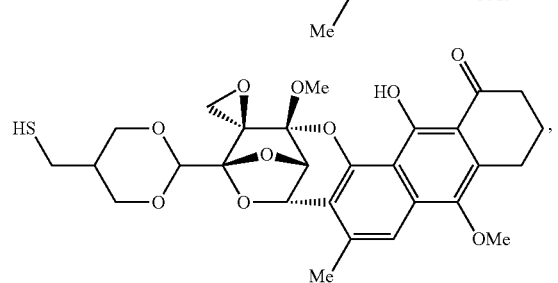
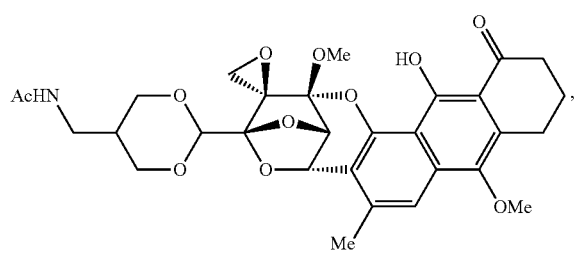
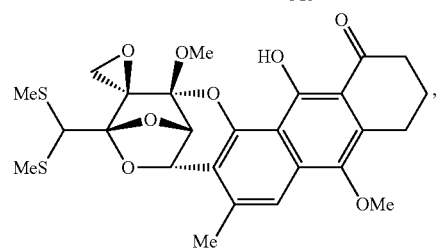
22
-continued
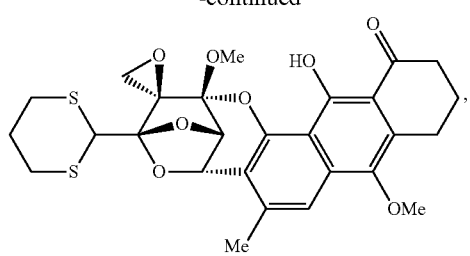
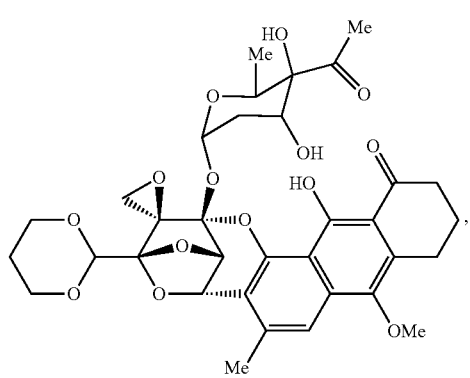
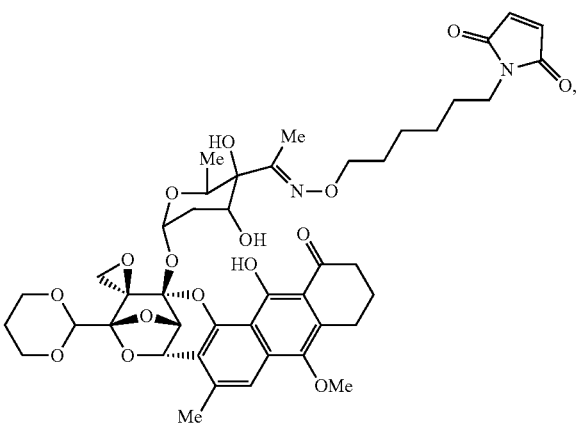
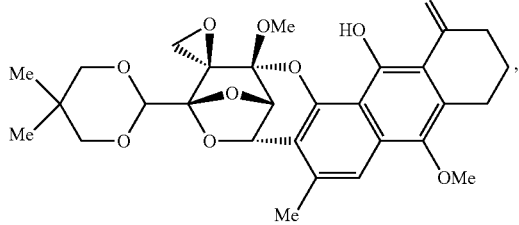
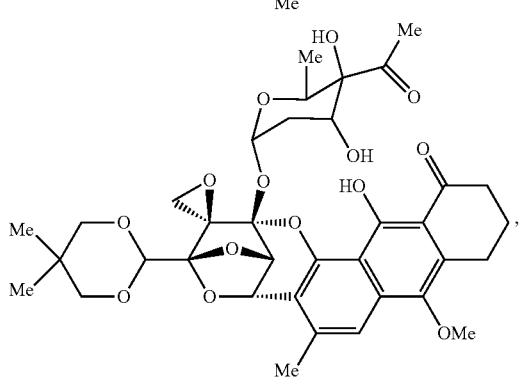

23
-continued
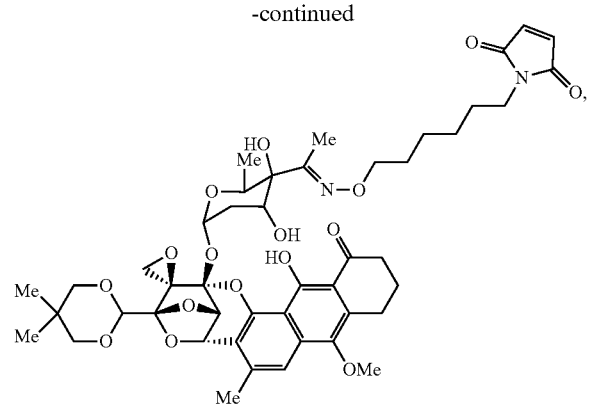
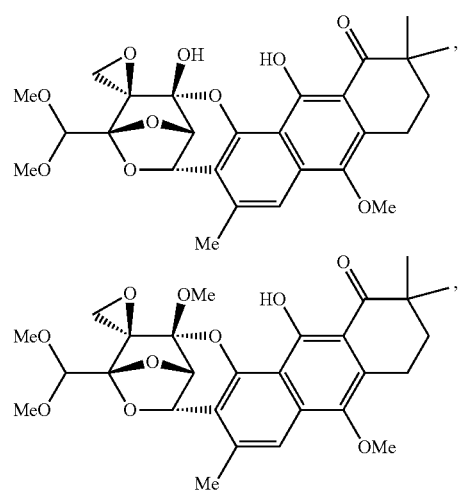
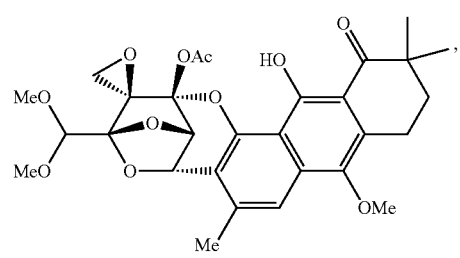
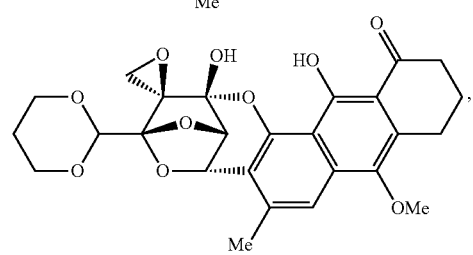
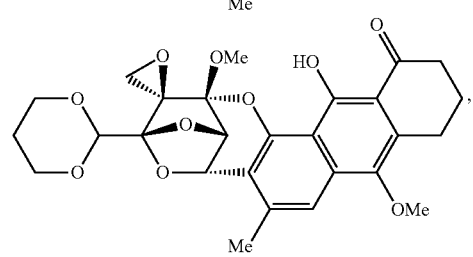
24
-continued
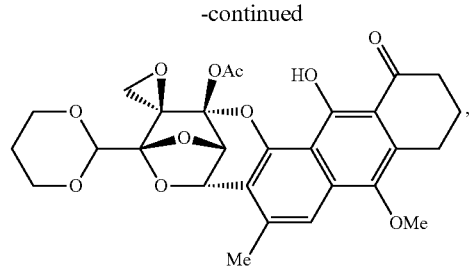
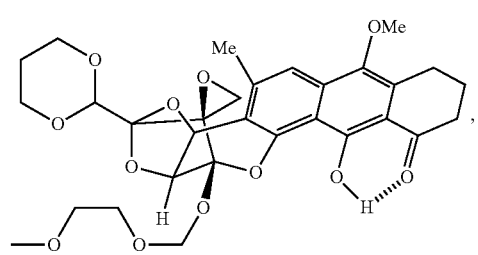
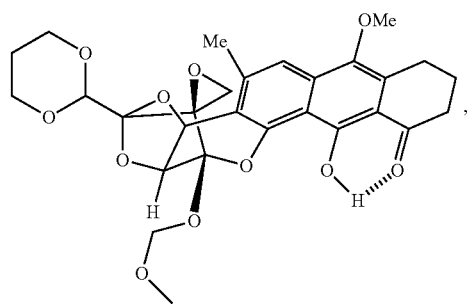
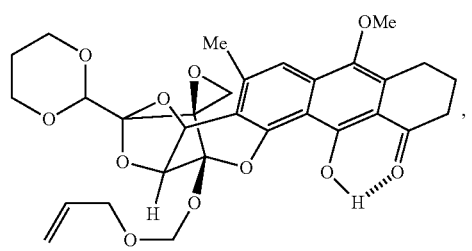
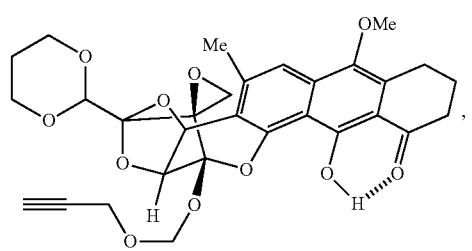
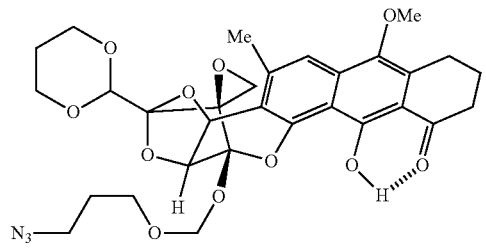

25
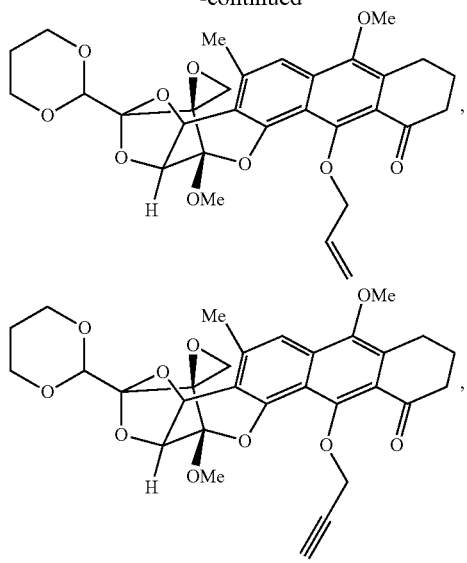
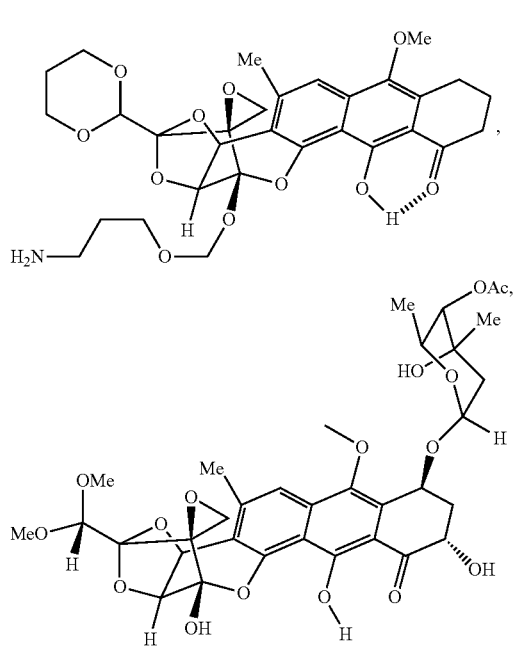
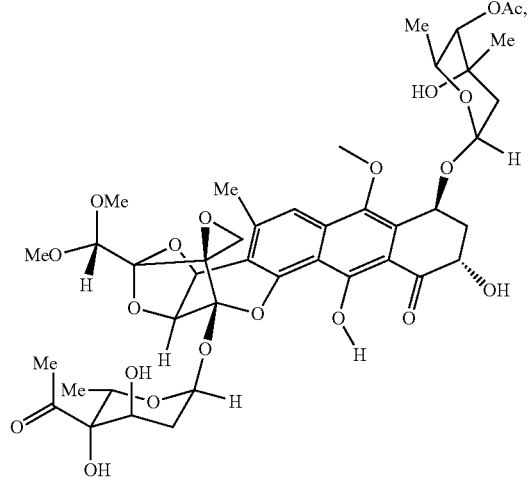
26
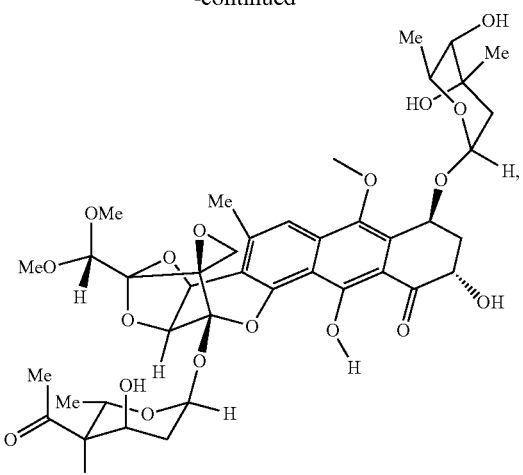
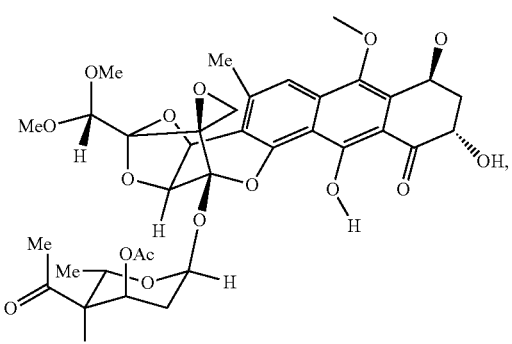
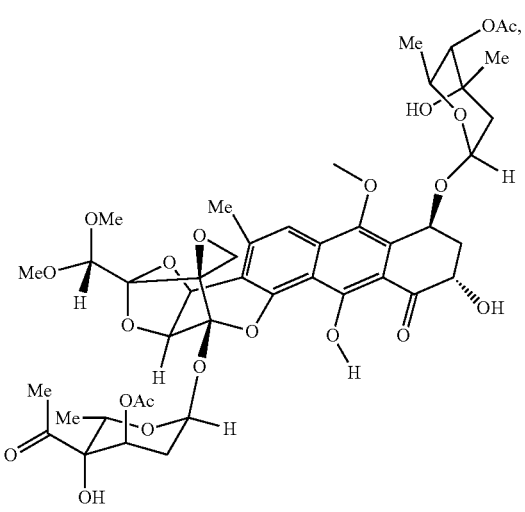

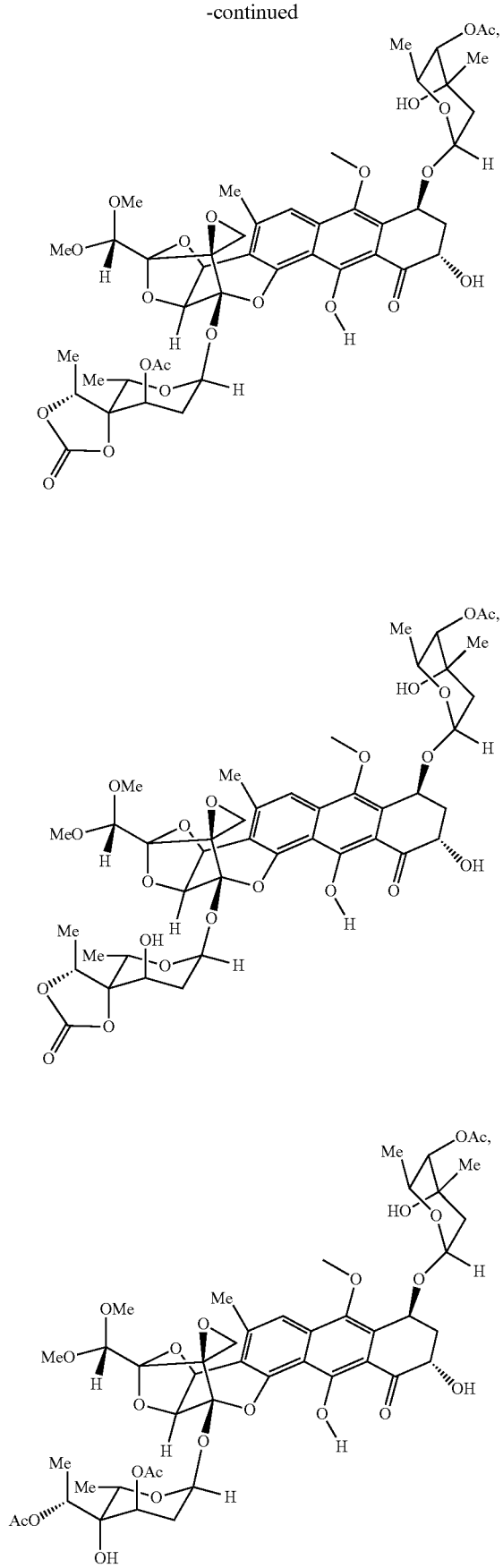
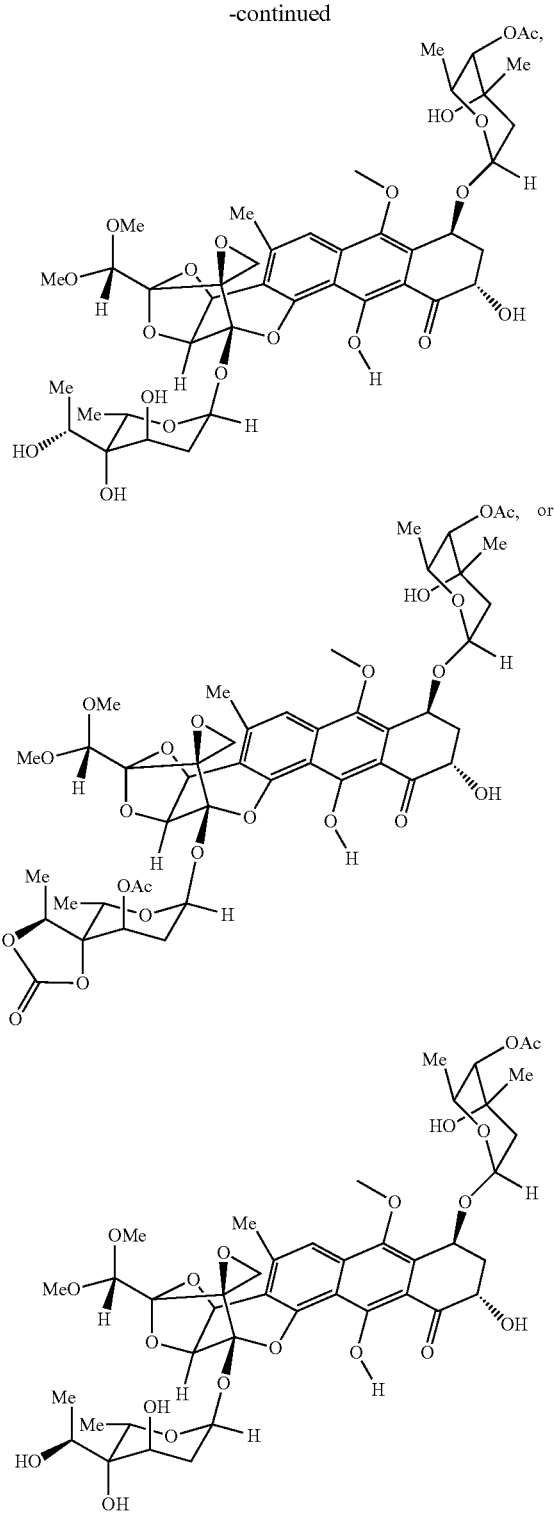

or a pharmaceutically acceptable salt thereof.

In yet another aspect, the present disclosure provides pharmaceutical compositions comprising a compound of the present disclosure and a pharmaceutically acceptable carrier. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

In yet another aspect, the present disclosure provides methods of treating a disease or disorder in a patient in need thereof comprising administering to the patient a pharmaceutically effective amount of a compound or composition of the present disclosure. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the method further comprises a second therapeutic agent or modality. In some embodiments, the compound is administered once. In some embodiments, the compound is administered two or more times.

In yet another aspect, the present disclosure provides methods of treating a disease or disorder in a patient in need thereof comprising administering to the patient a pharmaceutically effective amount of a compound or composition of the present disclosure. In some embodiments, the disease or disorder is a bacterial infection, a parasitic infection, or a viral infection. In some embodiments, the disease or disorder is a bacteria infection wherein the bacteria is a gram positive bacteria. In other embodiments, the disease or disorder is a bacteria infection wherein the bacteria is a gram negative bacteria. In some embodiments, the disease is a parasitic infection. In some embodiments, the parasitic infection causes malaria.

In still another aspect, the present disclosure provides methods of preparing a compound comprising reacting a compound of the formula:

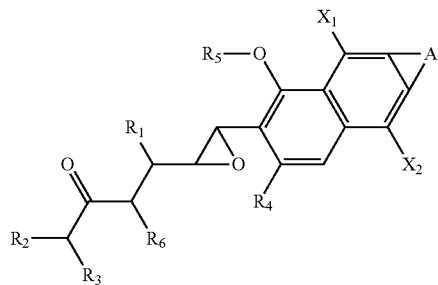

(II)

wherein: $R_1$ is amino, hydroxy, or mercapto; or $-OX_3$, wherein $X_3$ is a hydroxy protecting group, $-SX_4$, wherein $X_4$ is a thio protecting group, or $-NX_5X_6$, wherein either $X_5$ or $X_6$ is a monovalent amine protecting group and the other is a hydrogen or $X_5$ and $X_6$ are taken together and are a divalent amine protecting group; $R_2$ and $R_3$ are independently selected from hydrogen, amino, hydroxy, mercapto; alkyl$_{(C\leq12)}$, cycloalkyl$_{(C\leq12)}$, alkenyl$_{(C\leq12)}$, alkynyl$_{(C\leq12)}$, alkoxy$_{(C\leq12)}$, cycloalkoxy$_{(C\leq12)}$, alkenyloxy$_{(C\leq12)}$, alkynyloxy$_{(C\leq12)}$, alkylthio$_{(C\leq12)}$, cycloalkylthio$_{(C\leq12)}$, alkenylthio$_{(C\leq12)}$, alkynylthio$_{(C\leq12)}$, alkylamino$_{(C\leq12)}$, cycloalkylamino$_{(C\leq12)}$, alkenylamino$_{(C\leq12)}$, alkynylamino$_{(C\leq12)}$, or a substituted version of any of these groups, or $-OX_7$, wherein $X_7$ is a hydroxy protecting group, $-SX_8$, wherein $X_8$ is a thio protecting group, or $-NX_9X_{10}$, wherein either $X_9$ or $X_{10}$ is a monovalent amine protecting group and the other is a hydrogen or $X_9$ and $X_{10}$ are taken together and are a divalent amine protecting group; $R_2$ and $R_3$ are taken together and are alkoxydiyl$_{(C\leq8)}$, alkylaminodiyl$_{(C\leq12)}$, alkylthiodiyl$_{(C\leq12)}$, or a substituted version of any of these groups; $R_4$ is hydrogen, amino, halo, hydroxy, mercapto, alkyl$_{(C\leq12)}$ or substituted alkyl$_{(C\leq12)}$, or $-OX_{11}$, wherein $X_{11}$ is a hydroxy protecting group, $-SX_{12}$, wherein $X_{12}$ is a thio protecting group, or $-NX_{13}X_{14}$, wherein either $X_{13}$ or $X_{14}$ is a monovalent amine protecting group and the other is a hydrogen or $X_{13}$ and $X_{14}$ are taken together and are a divalent amine protecting group; $R_5$ is hydrogen or a hydroxy protecting group; $R_6$ is hydrogen or alkylidene$_{(C\leq12)}$, alkyl$_{(C\leq12)}$, cycloalkyl$_{(C\leq12)}$, alkenyl$_{(C\leq12)}$, alkynyl$_{(C\leq12)}$, alkoxy$_{(C\leq12)}$, cycloalkoxy$_{(C\leq12)}$, alkenyloxy$_{(C\leq12)}$, alkynyloxy$_{(C\leq12)}$, alkylamino$_{(C\leq12)}$, dialkylamino$_{(C\leq12)}$, or a substituted version of any of these groups $X_1$ and $X_2$ are each independently hydrogen, hydroxy, alkoxy$_{(C\leq12)}$, substituted alkoxy$_{(C\leq12)}$, or $-OX_{15}$, wherein $X_{15}$ is a hydroxy protecting group; or $X_{15}$ and $R_5$ are taken together and are a divalent diol protecting group; and A is a fused cycloalkanediyl and has the structure:

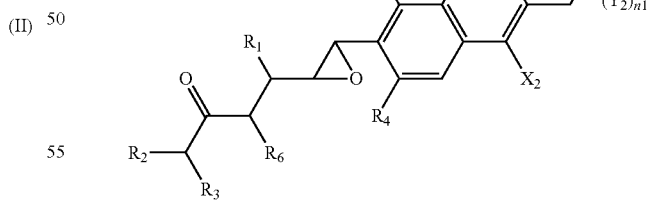

(IIIa)

wherein: $Y_1$ is hydrogen, oxo, alkoxy$_{(C\leq12)}$, substituted alkoxy$_{(C\leq12)}$, or $-OX_{16}$, wherein $X_{16}$ is a hydroxy protecting group; provided that when $Y_1$ is oxo, then the atom to which $Y_1$ is bound is part of a double bond, and provided that when the atom to which $Y_1$ is bound is part of a double bond, then $Y_1$ is oxo; $Y_2$ is hydrogen, hydroxy, alkoxy$_{(C\leq12)}$, substituted alkoxy$_{(C\leq12)}$, or $-OX_{17}$, wherein $X_{17}$ is a hydroxy protecting group; and $n_1$ is 0, 1, 2, 3, 4, 5, or 6; or A is a fused arenediyl and has the structure:

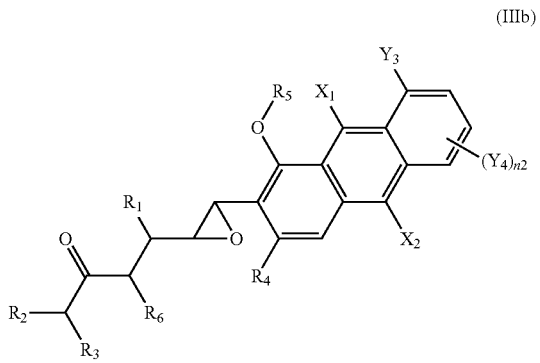

(IIIb)

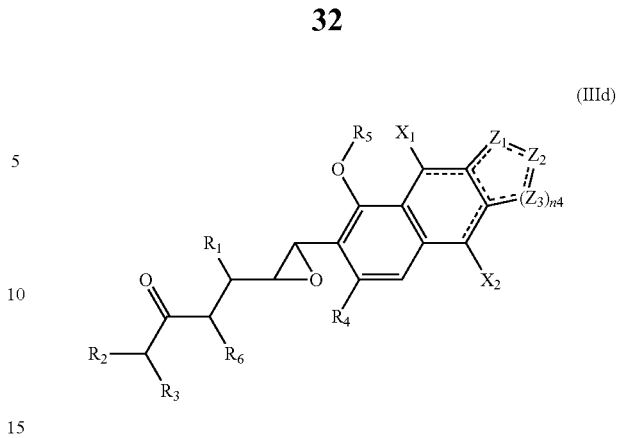

(IIId)

wherein: $Y_3$ is hydrogen, oxo, alkoxy$_{(C \leq 12)}$, substituted alkoxy$_{(C \leq 12)}$, or —$OX_{18}$, wherein $X_{18}$ is a hydroxy protecting group; provided that when $Y_3$ is oxo, then the atom to which $Y_3$ is bound is part of a double bond, and provided that when the atom to which $Y_3$ is bound is part of a double bond, then $Y_3$ is oxo; $Y_4$ is hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —$OX_{19}$, wherein $X_{19}$ is a hydroxy protecting group, —$SX_{20}$, wherein $X_{20}$ is a thio protecting group, or —$NX_{21}X_{22}$, wherein either $X_{21}$ or $X_{22}$ is a monovalent amine protecting group and the other is a hydrogen or $X_{21}$ and $X_{22}$ are taken together and are a divalent amine protecting group; and $n_2$ is 0, 1, 2, or 3; or A is a fused arenediyl with a fused heterocycloalkanediyl and has the structure:

wherein: $Z_1$, $Z_2$, and $Z_3$ are each independently selected from $CR_7R_7'$, $NR_8$, O, or S; $R_7$ and $R_7'$ are each independently hydrogen, amino, hydroxy, halo, cyano, nitro, sulfato, sulfamido; alkyl$_{(C \leq 6)}$, alkoxy$_{(C \leq 6)}$, alkylamino$_{(C \leq 6)}$, dialkylamino$_{(C \leq 12)}$, amido$_{(C \leq 6)}$, or a substituted version of any of these groups; and $R_8$ is hydrogen, alkyl$_{(C \leq 12)}$, or substituted alkyl$_{(C \leq 12)}$; provided that at least one of $Z_1$, $Z_2$, or $Z_3$ is $NR_7$, O, or S; $n_4$ is 1, 2, 3, or 4; or A is a fused arenediyl with a fused cycloalkanediyl and has the structure:

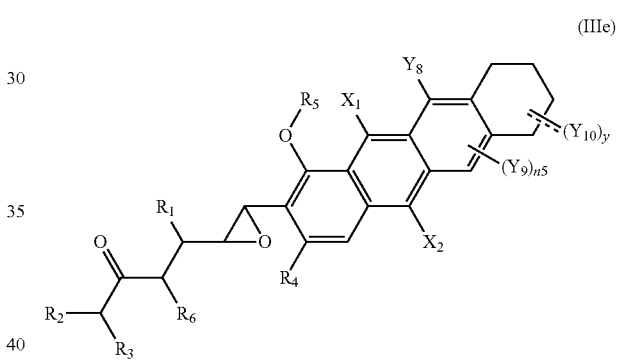

(IIIe)

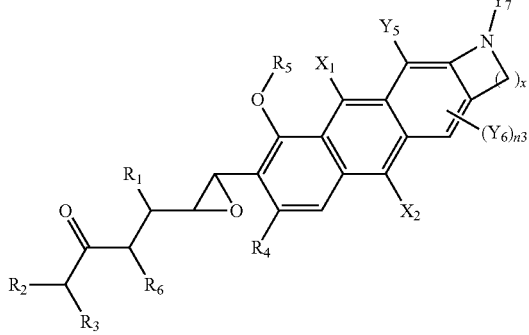

(IIIc)

wherein: $Y_8$ and $Y_9$ are each independently selected from hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —$OX_{28}$, wherein $X_{28}$ is a hydroxy protecting group, —$SX_{29}$, wherein $X_{29}$ is a thio protecting group, or —$NX_{30}X_{31}$, wherein either $X_{30}$ or $X_{31}$ is a monovalent amine protecting group and the other is a hydrogen or $X_{30}$ and $X_{31}$ are taken together and are a divalent amine protecting group; $Y_{10}$ is hydrogen, oxo, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —$OX_{32}$, wherein $X_{32}$ is a hydroxy protecting group, —$SX_{33}$, wherein $X_{33}$ is a thio protecting group, or —$NX_{34}X_{35}$, wherein either $X_{34}$ or $X_{35}$ is a monovalent amine protecting group and the other is a hydrogen or $X_{34}$ and $X_{35}$ are taken together and are a divalent amine protecting group, provided that when $Y_{10}$ is oxo, then the atom to which $Y_{10}$ is bound is part of a double bond, and provided that when the atom to which $Y_{10}$ is bound is part of a double bond, then $Y_{10}$ is oxo; $n_5$ is 0 or 1; and y is 0, 1, 2, 3, 4, 5, 6, 7, or 8; A is a fused arenediyl and has the structure:

wherein: $Y_5$ is hydrogen, alkoxy$_{(C \leq 12)}$, substituted alkoxy$_{(C \leq 12)}$, or —$OX_{23}$, wherein $X_{23}$ is a hydroxy protecting group; $Y_6$ is hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —$OX_{24}$, wherein $X_{24}$ is a hydroxy protecting group, —$SX_{25}$, wherein $X_{25}$ is a thio protecting group, or —$NX_{26}X_{27}$, wherein either $X_{26}$ or $X_{27}$ is a monovalent amine protecting group and the other is a hydrogen or $X_{26}$ and $X_{27}$ are taken together and are a divalent amine protecting group; $Y_7$ is hydrogen, alkyl$_{(C \leq 12)}$, or substituted alkyl$_{(C \leq 12)}$; $n_3$ is 0 or 1; and x is 1, 2, 3, or 4; or A is a fused heteroarenediyl and has the structure:

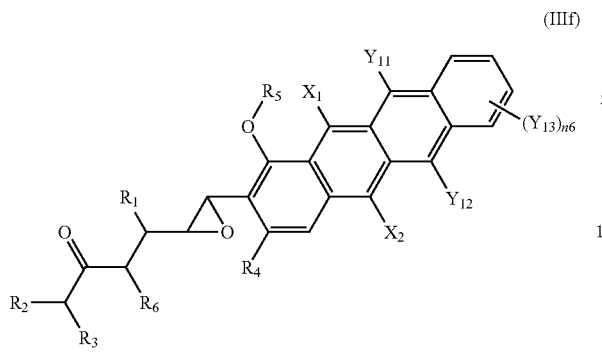
(IIIf)

wherein: $Y_{11}$ and $Y_{12}$ are each independently selected from hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —OX$_{36}$, wherein X$_{36}$ is a hydroxy protecting group, —SX$_{37}$, wherein X$_{37}$ is a thio protecting group, or —NX$_{38}$X$_{39}$, wherein either X$_{38}$ or X$_{39}$ is a monovalent amine protecting group and the other is a hydrogen or X$_{38}$ and X$_{39}$ are taken together and are a divalent amine protecting group; $Y_{13}$ is hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —OX$_{40}$, wherein X$_{40}$ is a hydroxy protecting group, —SX$_{41}$, wherein X$_{41}$ is a thio protecting group, or —NX$_{42}$X$_{43}$, wherein either X$_{42}$ or X$_{43}$ is a monovalent amine protecting group and the other is a hydrogen or X$_{42}$ and X$_{43}$ are taken together and are a divalent amine protecting group; and $n_6$ is 0, 1, 2, 3, or 4; with a Lewis acid under conditions sufficient to produce a compound of the formula:

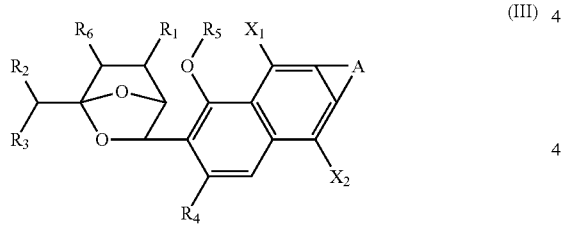
(III)

wherein: $R_1$, $R_2$, $R_3$, $R_4$, $R_5$, $R_6$, $X_1$, and $X_2$ are as defined above; A is a fused cycloalkanediyl and has the structure:

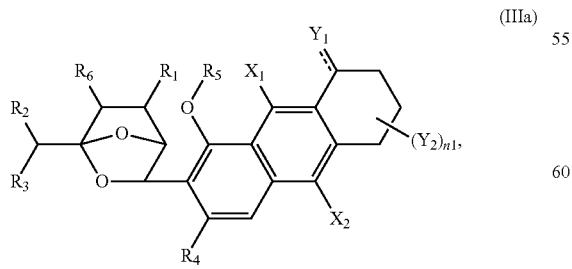
(IIIa)

wherein: $Y_1$, $Y_2$, and $n_1$ are as defined above; A is a fused arenediyl and has the structure:

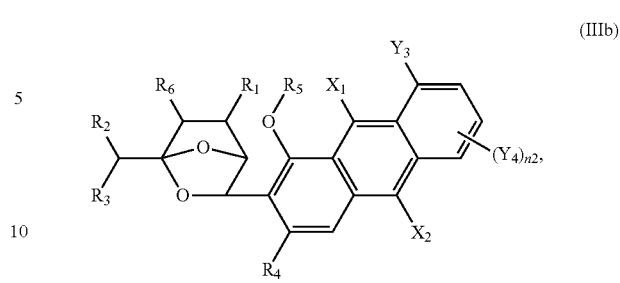
(IIIb)

wherein: $Y_3$, $Y_4$, and $n_2$ are as defined above; A is a fused arenediyl with a fused heterocycloalkanediyl and has the structure:

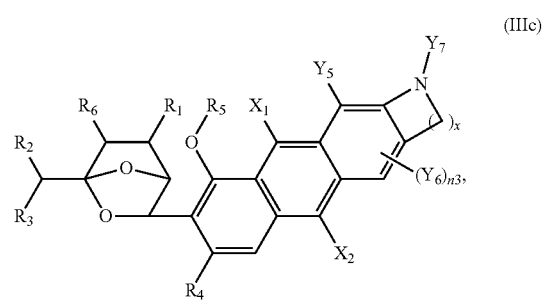
(IIIc)

wherein: $Y_5$, $Y_6$, $Y_7$, x, and $n_3$ are as defined above; A is a fused heteroarenediyl and has the structure:

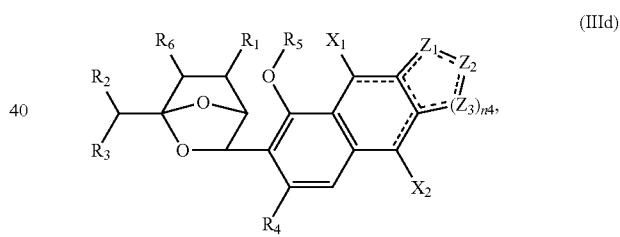
(IIId)

wherein: $Z_1$, $Z_2$, $Z_3$, and $n_4$ are as defined above; A is a fused arenediyl with a fused cycloalkanediyl and has the structure:

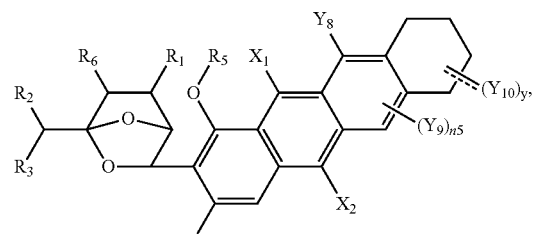
(IIIe)

or wherein: $Y_8$, $Y_9$, and $n_5$ are as defined above; A is a fused arenediyl and has the structure:

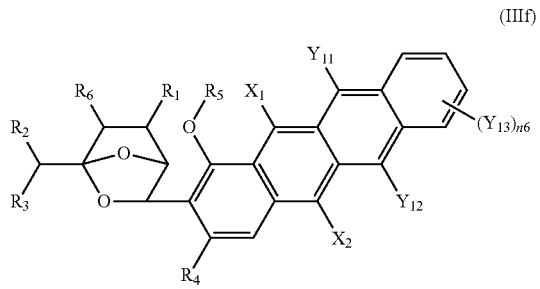
(IIIf)

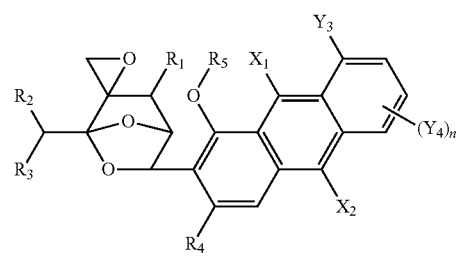
(IVb)

wherein: $Y_{11}$, $Y_{12}$, $Y_{13}$, and $n_6$ are as defined above; or a salt thereof. In some embodiments, the Lewis acid is a transition metal or a boron complex. In some embodiments, the Lewis acid is a boron complex. In some embodiments, the Lewis acid is boron trifluoride etherate. In some embodiments, the Lewis acid is a transition metal complex. In some embodiments, the Lewis acid is $SnCl_4$. In some embodiments, the method further comprises a solvent. In some embodiments, the solvent is chloroalkane$_{(C\leq12)}$. In some embodiments, the solvent is dichloromethane. In some embodiments, $R_6$ is alkylidene$_{(C\leq12)}$ or substituted alkyldiene$_{(C\leq12)}$. In some embodiments, the method further comprises reacting the compound with an epoxidizing agent under conditions to sufficient to produce a compound of the formula:

wherein: $Y_3$, $Y_4$, and $n_2$ are as defined above; A is a fused arenediyl with a fused heterocycloalkanediyl and has the structure:

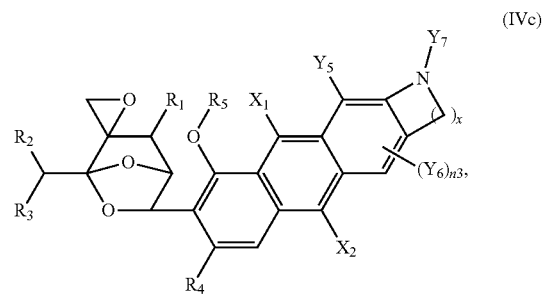
(IVc)

wherein: $Y_5$, $Y_6$, $Y_7$, x, and $n_3$ are as defined above; A is a fused heteroarenediyl and has the structure:

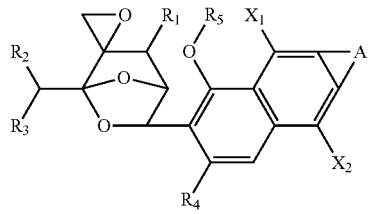
(IV)

wherein: $R_1$, $R_2$, $R_3$, $R_4$, $R_5$, $X_1$, and $X_2$ are as defined above; A is a fused cycloalkanediyl and has the structure:

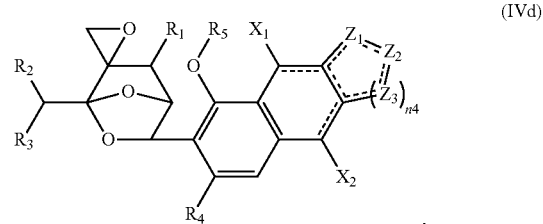
(IVd)

wherein: $Z_1$, $Z_2$, $Z_3$, and $n_4$ are as defined above; A is a fused arenediyl with a fused cycloalkanediyl and has the structure:

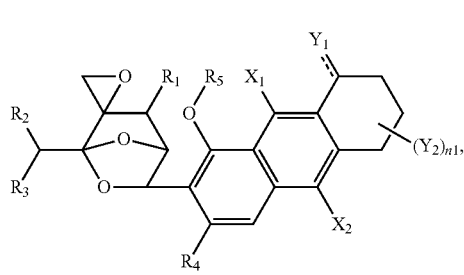
(IVa)

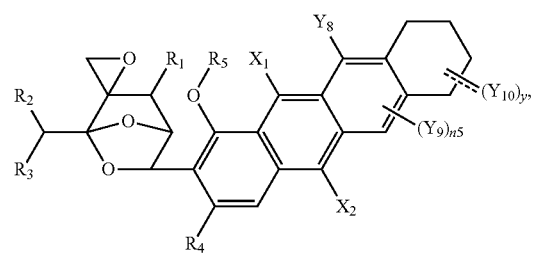
(IVe)

wherein: $Y_1$, $Y_2$, and $n_1$ are as defined above; A is a fused arenediyl and has the structure:

or wherein: $Y_8$, $Y_9$, and $n_5$ are as defined above; A is a fused arenediyl and has the structure:

(IVf)

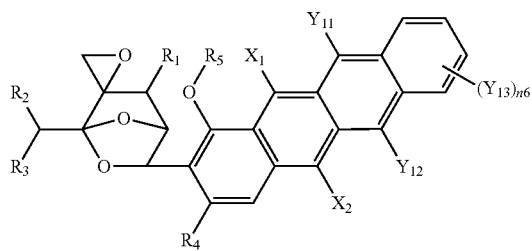

wherein: $Y_{11}$, $Y_{12}$, $Y_{13}$, and $n_6$ are as defined above; In some embodiments, the epoxidizing agent is osmium tetraoxide with tosyl chloride and a base. In some embodiments, the osmium tetraoxide is added to the compound and after a time period of about 1 hour to about 24 hours, the tosyl chloride and the base are added. In some embodiments, the method further comprises reacting the compound with an oxidizing agent under conditions sufficient to produce a compound of the formula:

(V)

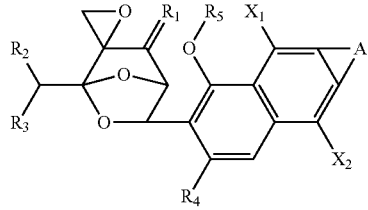

wherein: $R_2$, $R_3$, $R_4$, $R_5$, $X_1$, and $X_2$ are as defined above; $R_1$ is O, S, or NH; and A is a fused cycloalkanediyl and has the structure:

(Va)

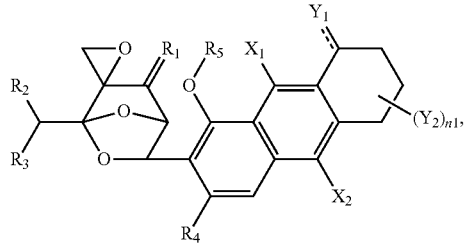

wherein: $Y_1$, $Y_2$, and $n_1$ are as defined above; A is a fused arenediyl and has the structure:

(Vb)

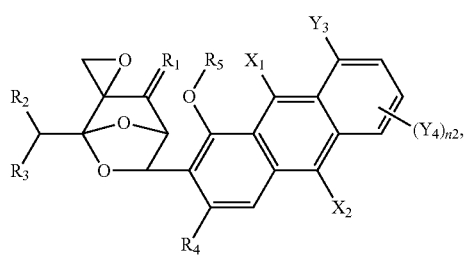

wherein: $Y_3$, $Y_4$, and $n_2$ are as defined above; A is a fused arenediyl with a fused heterocycloalkanediyl and has the structure:

(Vc)

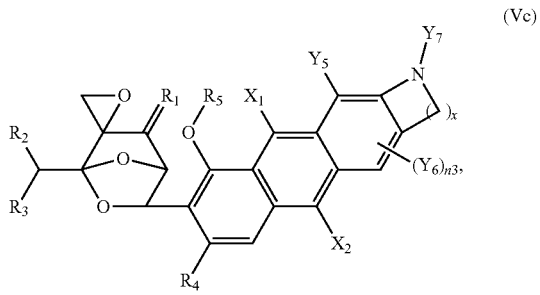

wherein: $Y_5$, $Y_6$, $Y_7$, x, and $n_3$ are as defined above; A is a fused heteroarenediyl and has the structure:

(Vd)

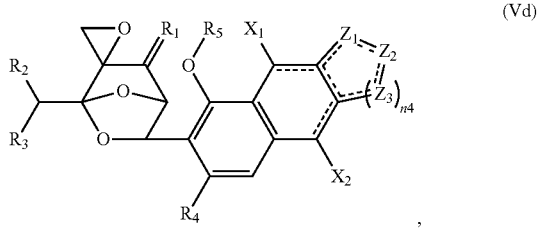

wherein: $Z_1$, $Z_2$, $Z_3$, and $n_4$ are as defined above; A is a fused arenediyl with a fused cycloalkanediyl and has the structure:

(Ve)

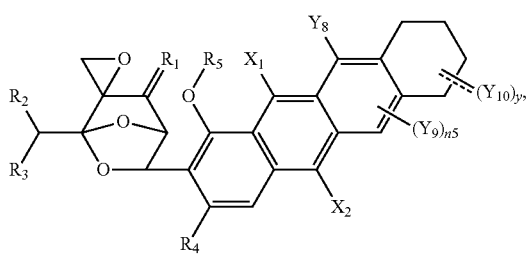

or wherein: $Y_8$, $Y_9$, and $n_5$ are as defined above; A is a fused arenediyl and has the structure:

(Vf)

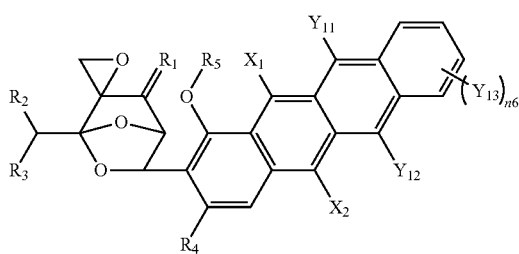

wherein: $Y_{11}$, $Y_{12}$, $Y_{13}$, and $n_6$ are as defined above; or a salt thereof. In some embodiments, the oxidizing agent is tetrapropylammonium perruthenate and N-methylmorpholine N-oxide.

In some embodiments, the method further comprises reacting the compound with a fluoride source under condition sufficient to produce a compound of the formula:

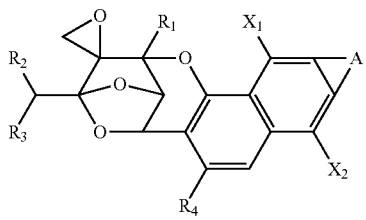

(I)

wherein: $R_2$, $R_3$, $R_4$, $X_1$, and $X_2$ are as defined above; $R_1$ is amino, hydroxy, or mercapto; alkoxy$_{(C \leq 12)}$, cycloalkoxy$_{(C \leq 12)}$, alkenyloxy$_{(C \leq 12)}$, alkynyloxy$_{(C \leq 12)}$, alkylthio$_{(C \leq 12)}$, cycloalkylthio$_{(C \leq 12)}$, alkenylthio$_{(C \leq 12)}$, alkynylthio$_{(C \leq 12)}$, alkylamino$_{(C \leq 12)}$, cycloalkylamino$_{(C \leq 12)}$, alkenylamino$_{(C \leq 12)}$, alkynylamino$_{(C \leq 12)}$, dialkylamino$_{(C \leq 12)}$, dicycloalkylamino$_{(C \leq 12)}$, dialkenylamino$_{(C \leq 12)}$, dialkynylamino$_{(C \leq 12)}$, or a substituted version of any of these groups; A is a fused cycloalkanediyl and has the structure:

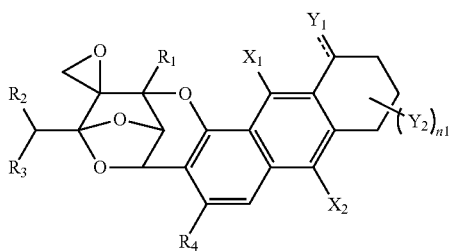

(Ia)

wherein: $Y_1$, $Y_2$, and $n_1$ are as defined above; A is a fused arenediyl and has the structure:

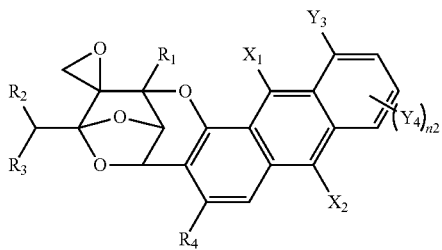

(Ib)

wherein: $Y_3$, $Y_4$, and $n_2$ are as defined above; A is a fused arenediyl with a fused heterocycloalkanediyl and has the structure:

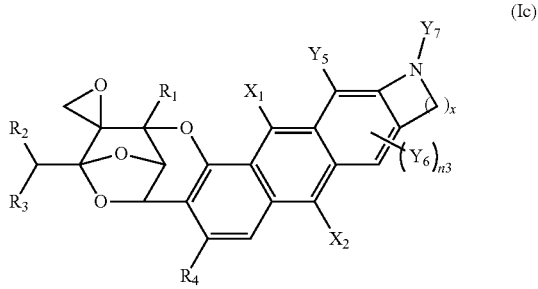

(Ic)

wherein: $Y_5$, $Y_6$, $Y_7$, x, and $n_3$ are as defined above; A is a fused heteroarenediyl and has the structure:

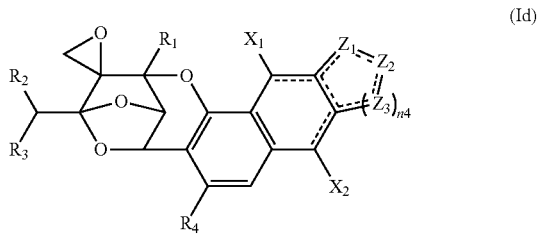

(Id)

wherein: $Z_1$, $Z_2$, $Z_3$, and $n_4$ are as defined above; A is a fused arenediyl with a fused cycloalkanediyl and has the structure:

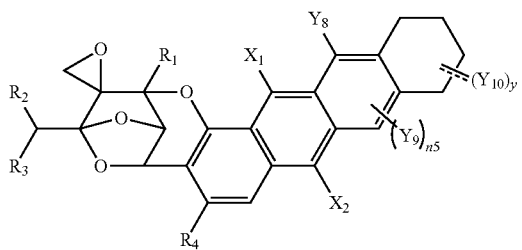

(Ie)

wherein: $Y_8$, $Y_9$, and $n_5$ are as defined above; A is a fused arenediyl and has the structure:

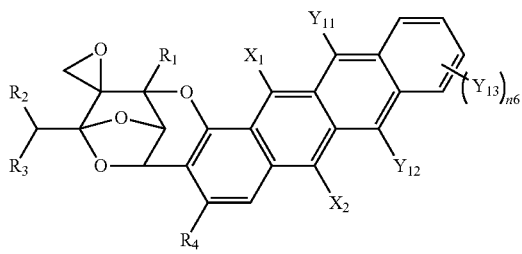

(If)

wherein: $Y_{11}$, $Y_{12}$, $Y_{13}$, and $n_6$ are as defined above; or a salt thereof. In some embodiments, the fluoride source is Et$_3$N.3HF. In some embodiments, the method further comprises one or more deprotection steps.

In another aspect, the present disclosure provides conjugates of the formula:

(A-L)$_n$-X  (VI)

wherein: A is a compound described herein; L is a covalent bond or a linker; n is 1, 2, 3, 4, 5, 6, 7, 8, 9, 10, 11, or 12; and X is a cell targeting moiety.

In some embodiments, one or more steps of the reaction further comprises purifying the reaction in a purification step. In some embodiments, the purification method is chromatography. In some embodiments, the purification method is column chromatography or high performance liquid chromatography.

It is contemplated that any method or composition described herein can be implemented with respect to any other method or composition described herein. For example, an aldehyde synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description.

DESCRIPTION OF ILLUSTRATIVE EMBODIMENTS

Figure 1:
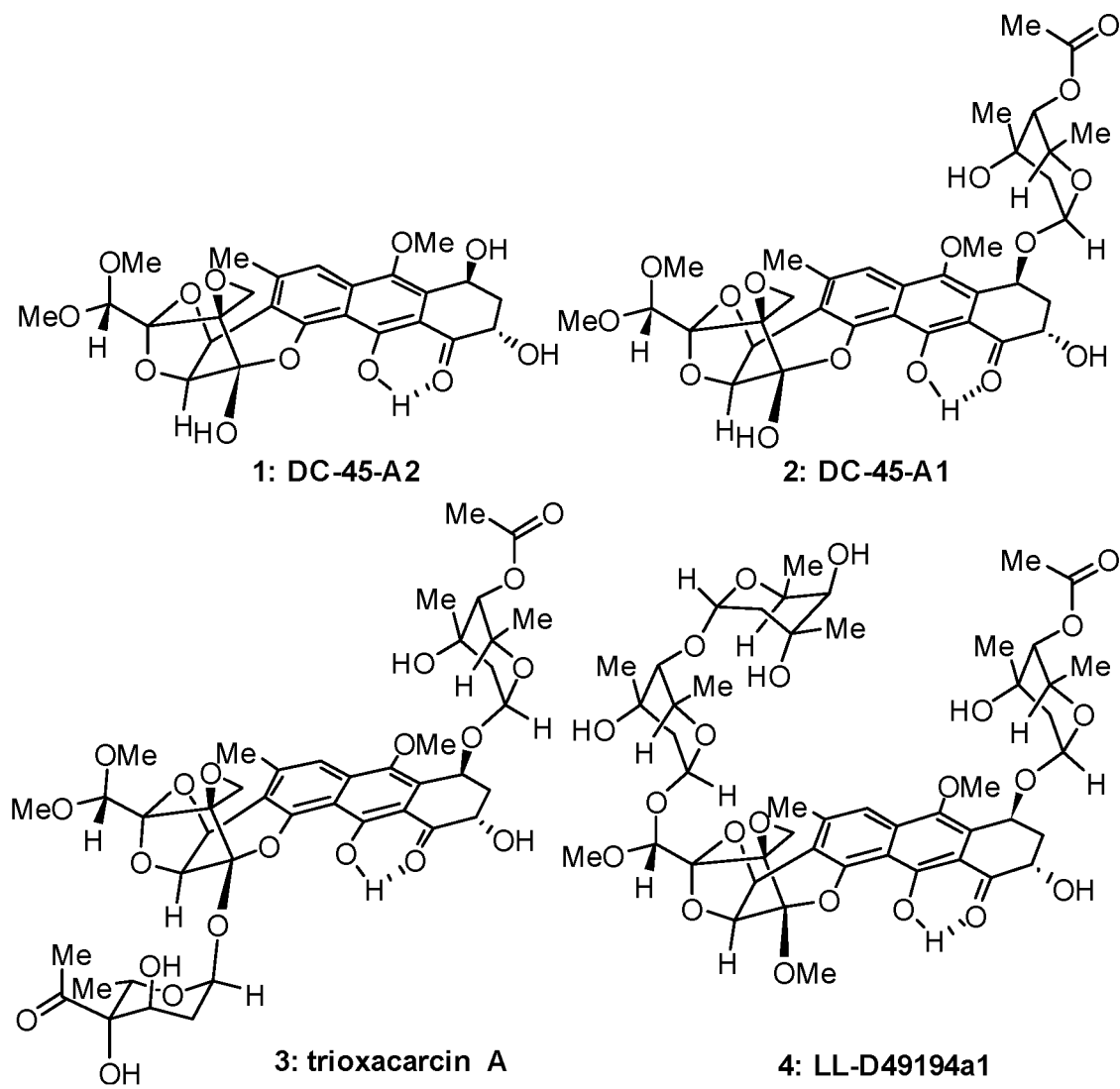
FIG. 1—Molecular structures of trioxacarcins: DC-45-A2 (1), DC-45-A1 (2), A (3) and LL-D49194α1 (4).

The present disclosure relates to a modular synthesis of trioxacarcin DC-45-A2 and development of trioxacarcin analogs. In some aspects, the present disclosure provides novel analogs of trioxacarcin which may be useful in the treatment of proliferative diseases such as cancer. Without wishing to be bound by any theory, trioxacarcin are antitumor antibiotics. In yet another aspect, the present disclosure relates to a modular synthesis which incorporates a macrocyclic rearrangement which constructs the dioxabicyclo [2.2.1]heptane. These and other aspects of the disclosure are described in greater detail below.

I. Compounds and Formulations Thereof

A. Compounds

In one aspect, the present disclosure provides compounds of the formula:

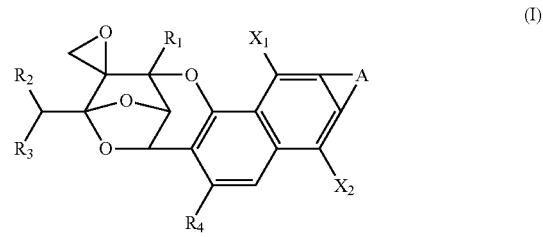

(I)

wherein:
R$_1$ is amino, hydroxy, or mercapto;
alkoxy$_{(C\leq12)}$, cycloalkoxy$_{(C\leq12)}$, alkenyloxy$_{(C\leq12)}$, alkynyloxy$_{(C\leq12)}$, acyloxy$_{(C\leq12)}$, alkylthio$_{(C\leq12)}$, cycloalkylthio$_{(C\leq12)}$, alkenylthio$_{(C\leq12)}$, alkynylthio$_{(C\leq12)}$, acylthio$_{(C\leq12)}$, alkylamino$_{(C\leq12)}$, cycloalkylamino$_{(C\leq12)}$, alkenylamino$_{(C\leq12)}$, alkynylamino$_{(C\leq12)}$, dialkylamino$_{(C\leq12)}$, dicycloalkylamino$_{(C\leq12)}$, dialkenylamino$_{(C\leq12)}$, dialkynylamino$_{(C\leq12)}$, amido$_{(C\leq12)}$, or a substituted version of any of these groups; or
R$_1$ is a group of the formula: —O-alkanediyl$_{(C\leq8)}$-alkoxy$_{(C\leq12)}$, —O-alkanediyl$_{(C\leq8)}$-alkenyloxy$_{(C\leq12)}$, —O-alkanediyl$_{(C\leq8)}$-alkynyloxy$_{(C\leq12)}$, or a substituted version thereof; or
R$_1$ is a group of the formula:

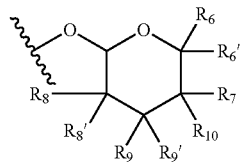

wherein:
R$_6$, R$_6'$, R$_7$, R$_8$, R$_8'$, R$_9$, and R$_9'$ are each independently hydrogen, hydroxy, alkyl$_{(C\leq8)}$, alkoxy$_{(C\leq8)}$, acyloxy$_{(C\leq8)}$, substituted alkyl$_{(C\leq8)}$, substituted alkoxy$_{(C\leq8)}$, or substituted acyloxy$_{(C\leq8)}$; and
R$_{10}$ is hydrogen, hydroxy, alkyl$_{(C\leq12)}$, alkoxy$_{(C\leq12)}$, acyl$_{(C\leq12)}$, substituted alkyl$_{(C\leq12)}$, substituted alkoxy$_{(C\leq12)}$, substituted acyl$_{(C\leq12)}$, or a group of the formula:

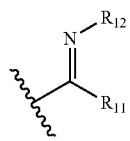

wherein:
R$_{11}$ is hydrogen, alkyl$_{(C\leq8)}$, or substituted alkyl$_{(C\leq8)}$; and
R$_{12}$ is hydrogen, hydroxy, alkoxy$_{(C\leq12)}$, substituted alkoxy$_{(C\leq12)}$, —O-alkanediyl$_{(C\leq12)}$-a thiol reactive group, or a substituted version of —O-al-kanediyl$_{(C≤12)}$-a thiol reactive group; or R$_7$ and R$_{10}$ are taken together to form a heterocyclic compound of the formula:

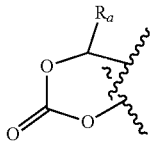

wherein:
R$_a$ is hydrogen, alkyl$_{(C≤6)}$, or substituted alkyl$_{(C≤6)}$;

R$_2$ and R$_3$ are independently hydrogen, amino, hydroxy, mercapto;

alkyl$_{(C≤12)}$, cycloalkyl$_{(C≤12)}$, alkenyl$_{(C≤12)}$, alkynyl$_{(C≤12)}$, alkoxy$_{(C≤12)}$, cycloalkoxy$_{(C≤12)}$, alkenyloxy$_{(C≤12)}$, alkynyloxy$_{(C≤12)}$, alkylthio$_{(C≤12)}$, cycloalkylthio$_{(C≤12)}$, alkenylthio$_{(C≤12)}$, alkynylthio$_{(C≤12)}$, alkylamino$_{(C≤12)}$, cycloalkylamino$_{(C≤12)}$, alkenylamino$_{(C≤12)}$, alkynylamino$_{(C≤12)}$, or a substituted version of any of these groups;

R$_2$ and R$_3$ are taken together and are alkoxydiyl$_{(C≤8)}$, alkylaminodiyl$_{(C≤12)}$, alkylthiodiyl$_{(C≤12)}$, or a substituted version of any of these groups;

R$_4$ is hydrogen, amino, halo, hydroxy, mercapto, alkyl$_{(C≤12)}$ or substituted alkyl$_{(C≤12)}$;

X$_1$ and X$_2$ are each independently hydrogen, hydroxy, or alkoxy$_{(C≤12)}$, alkenyloxy$_{(C≤12)}$, alkynyloxy$_{(C≤12)}$, or a substituted version of any of these groups; and A is a fused cycloalkanediyl and has the structure:

(Ia)

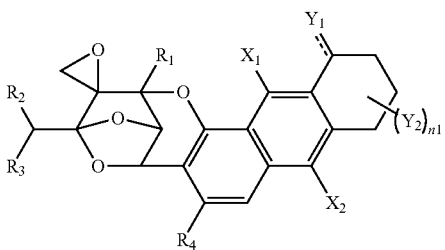

wherein:
Y$_1$ is hydrogen, oxo, alkoxy$_{(C≤12)}$, or substituted alkoxy$_{(C≤12)}$, provided that when Y$_1$ is oxo, then the atom to which Y$_1$ is bound is part of a double bond, and provided that when the atom to which Y$_1$ is bound is part of a double bond, then Y$_1$ is oxo;

Y$_2$ is hydrogen, hydroxy, alkyl$_{(C≤12)}$, substituted alkyl$_{(C≤12)}$, alkoxy$_{(C≤12)}$, substituted alkoxy$_{(C≤12)}$, or —OX$_3$, wherein X$_3$ is a hydroxy protecting group; or a group of the formula:

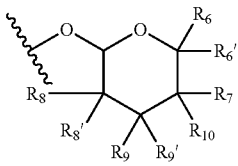

wherein:
R$_6$, R$_6$', R$_7$, R$_8$, R$_8$', R$_9$, and R$_9$' are each independently hydrogen, hydroxy, alkyl$_{(C≤8)}$, alkoxy$_{(C≤8)}$, acyloxy$_{(C≤8)}$, substituted alkyl$_{(C≤8)}$, substituted alkoxy$_{(C≤8)}$, or substituted acyloxy$_{(C≤8)}$; and R$_{10}$ is hydrogen, hydroxy, alkyl$_{(C≤12)}$, alkoxy$_{(C≤12)}$, acyl$_{(C≤12)}$, substituted alkyl$_{(C≤12)}$, substituted alkoxy$_{(C≤12)}$, substituted acyl$_{(C≤12)}$, or a group of the formula:

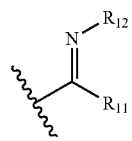

wherein:
R$_{11}$ is hydrogen, alkyl$_{(C≤8)}$, or substituted alkyl$_{(C≤8)}$; and R$_{12}$ is hydrogen, hydroxy, alkoxy$_{(C≤12)}$, substituted alkoxy$_{(C≤12)}$, —O— alkanediyl$_{(C≤12)}$-a thiol reactive group, or a substituted version of —O-alkanediyl$_{(C≤12)}$-a thiol reactive group; or R$_7$ and R$_{10}$ are taken together to form a heterocyclic compound of the formula:

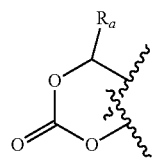

wherein:
R$_a$ is hydrogen, alkyl$_{(C≤6)}$, or substituted alkyl$_{(C≤6)}$; and n$_1$ is 0, 1, 2, 3, 4, 5, or 6; or A is a fused arenediyl and has the structure:

(Ib)

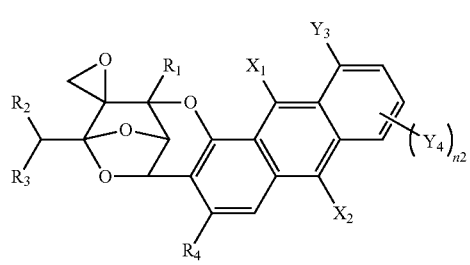

wherein:
Y$_3$ is hydrogen, oxo, alkoxy$_{(C≤12)}$, or substituted alkoxy$_{(C≤12)}$, provided that when Y$_3$ is oxo, then the atom to which Y$_3$ is bound is part of a double bond, and provided that when the atom to which Y$_3$ is bound is part of a double bond, then Y$_3$ is oxo;

Y$_4$ is hydrogen, hydroxy, amino, mercapto, alkoxy$_{(C≤12)}$, substituted alkoxy$_{(C≤12)}$, alkylthio$_{(C≤12)}$, substituted alkylthio$_{(C≤12)}$, alkylamino$_{(C≤12)}$, substituted alkylamino$_{(C≤12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or $X_5$ and $X_6$ are taken together and are a divalent amine protecting group; and $n_2$ is 0, 1, 2, or 3; or A is a fused arenediyl with a fused heterocycloalkanediyl and has the structure:

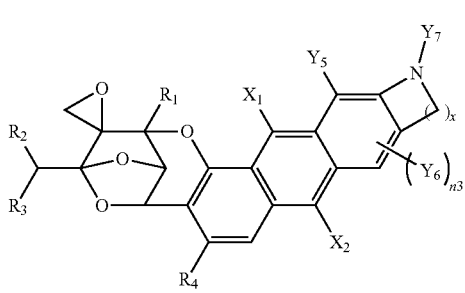

(Ic)

wherein:

$Y_5$ is hydrogen, oxo, alkoxy$_{(C≤12)}$, or substituted alkoxy$_{(C≤12)}$, provided that when $Y_3$ is oxo, then the atom to which $Y_3$ is bound is part of a double bond, and provided that when the atom to which $Y_3$ is bound is part of a double bond, then $Y_3$ is oxo;

$Y_6$ is hydrogen, hydroxy, amino, mercapto, alkoxy$_{(C≤12)}$, substituted alkoxy$_{(C≤12)}$, alkylthio$_{(C≤12)}$, substituted alkylthio$_{(C≤12)}$, alkylamino$_{(C≤12)}$, substituted alkylamino$_{(C≤12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group;

$Y_7$ is hydrogen, alkyl$_{(C≤12)}$, or substituted alkyl$_{(C≤12)}$;

$n_3$ is 0 or 1; and x is 1, 2, 3, or 4; or

A is a fused heteroarenediyl and has the structure:

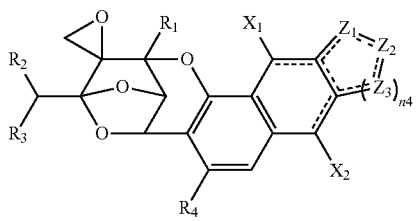

(Id)

wherein:

$Z_1$, $Z_2$, and $Z_3$ are each independently selected from CR$_5$R$_5$', NR$_5$", O, or S;

R$_5$ and R$_5$' are each independently hydrogen, amino, hydroxy, halo, cyano, nitro, sulfato, sulfamido; alkyl$_{(C≤6)}$, alkoxy$_{(C≤6)}$, alkylamino$_{(C≤6)}$, dialkylamino$_{(C≤12)}$, amido$_{(C≤6)}$, or a substituted version of any of these groups; and R$_5$" is hydrogen, alkyl$_{(C≤12)}$, or substituted alkyl$_{(C≤12)}$;

provided that at least one of $Z_1$, $Z_2$, or $Z_3$ is NR$_5$", O, or S;

$n_4$ is 1, 2, 3, or 4; or

A is a fused arenediyl with a fused cycloalkanediyl and has the structure:

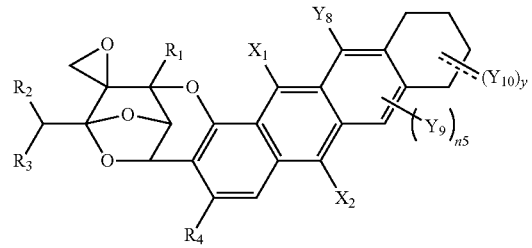

(Ie)

wherein:

$Y_8$ and $Y_9$ are each independently selected from hydrogen, hydroxy, amino, mercapto, alkoxy$_{(C≤12)}$, substituted alkoxy$_{(C≤12)}$, alkylthio$_{(C≤12)}$, substituted alkylthio$_{(C≤12)}$, alkylamino$_{(C≤12)}$, substituted alkylamino$_{(C≤12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group;

$Y_{10}$ is hydrogen, oxo, hydroxy, amino, mercapto, alkoxy$_{(C≤12)}$, substituted alkoxy$_{(C≤12)}$, alkylthio$_{(C≤12)}$, substituted alkylthio$_{(C≤12)}$, alkylamino$_{(C≤12)}$, substituted alkylamino$_{(C≤12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group, provided that when $Y_3$ is oxo, then the atom to which $Y_3$ is bound is part of a double bond, and provided that when the atom to which $Y_3$ is bound is part of a double bond, then $Y_3$ is OXO;

$n_5$ is 0 or 1; and y is 0, 1, 2, 3, 4, 5, 6, 7, or 8;

A is a fused arenediyl and has the structure:

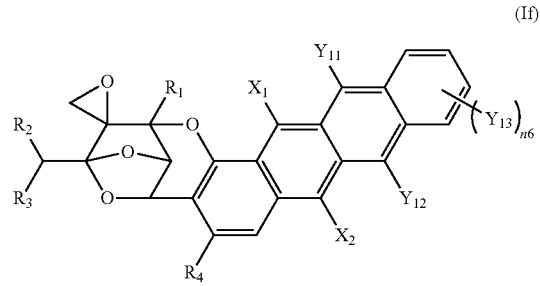

(If)

wherein:

$Y_{11}$ and $Y_{12}$ are each independently selected from hydrogen, hydroxy, amino, mercapto, alkoxy$_{(C≤12)}$, substituted alkoxy$_{(C≤12)}$, alkylthio$_{(C≤12)}$, substituted alkylthio$_{(C≤12)}$, alkylamino$_{(C≤12)}$, substituted alkylamino$_{(C≤12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group;

$Y_{13}$ is hydrogen, hydroxy, amino, mercapto, alkoxy$_{(C \leq 12)}$, substituted alkoxy$_{(C \leq 12)}$, alkylthio$_{(C \leq 12)}$, substituted alkylthio$_{(C \leq 12)}$, alkylamino$_{(C \leq 12)}$, substituted alkylamino$_{(C \leq 12)}$, —OX$_3$, wherein X$_3$ is a hydroxy protecting group, —SX$_4$, wherein X$_4$ is a thio protecting group, or —NX$_5$X$_6$, wherein either X$_5$ or X$_6$ is a monovalent amine protecting group and the other is a hydrogen or X$_5$ and X$_6$ are taken together and are a divalent amine protecting group, provided that when Y$_3$ is oxo, then the atom to which Y$_3$ is bound is part of a double bond, and provided that when the atom to which Y$_3$ is bound is part of a double bond, then Y$_3$ is oxo; and
$n_6$ is 0, 1, 2, 3, or 4;

provided that R$_1$ is not hydroxy and either R$_2$ or R$_3$ is methoxy when A is a fused cycloalkanediyl of the formula:

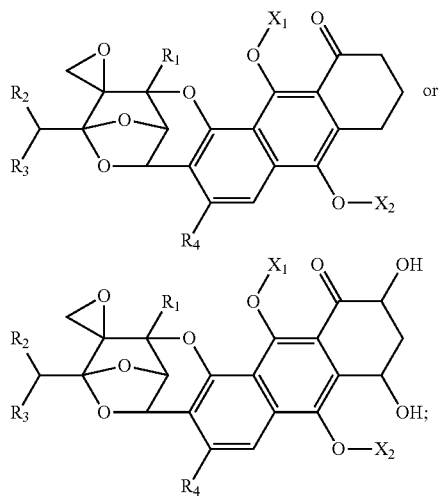

or a pharmaceutically acceptable salt thereof.

Additionally, the compounds provided by the present disclosure are shown, for example, above in the summary of the invention section and in the examples and claims below. They may be made using the methods outlined in the Examples section. Trioxacarcin and derivatives thereof can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Trioxacarcin and derivatives of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent trioxacarcin and derivatives thereof of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Trioxacarcin and derivatives thereof of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up trioxacarcin and derivatives thereof of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

Trioxacarcin and derivatives thereof of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the invention contemplates prodrugs of compounds of the present invention as well as methods of delivering prodrugs. Prodrugs of trioxacarcin and derivatives thereof employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of trioxacarcin and its derivatives provided herein are within the scope of the invention. It will also be appreciated by those skilled in organic chemistry that many organic compounds can exist in more than one crystalline form. For example, crystalline form may vary from solvate to solvate. Thus, all crystalline forms of trioxacarcin and derivatives thereof or the pharmaceutically acceptable solvates thereof are within the scope of the present invention.

B. Formulations

In some embodiments of the present disclosure, the compounds are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., trioxacarcin and its derivatives) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. Bacterial Infections

In some aspects of the present disclosure, the compounds disclosed herein may be used to treat a bacterial infection. While humans contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy.

Additionally, different bacteria have a wide range of interactions with body and those interactions can modulate ability of the bacteria to cause an infection. For example, bacteria can be conditionally pathogenic such that they only cause an infection under specific conditions. For example, *Staphylococcus* and *Streptococcus* bacteria exist in the normal human bacterial biome, but these bacteria when they are allowed to colonize other parts of the body causing a skin infection, pneumonia, or sepsis. Other bacteria are known as opportunistic pathogens and only cause diseases in a patient with a weakened immune system or another disease or disorder.

Bacteria can also be intracellular pathogens which can grow and reproduce within the cells of the host organism. Such bacteria can be divided into two major categories as either obligate intracellular parasites or facultative intracellular parasites. Obligate intracellular parasites require the host cell in order to reproduce and include such bacteria as but are not limited to *Chlamydophila, Rickettsia*, and *Ehrlichia* which are known to cause pneumonia, urinary tract infections, typhus, and Rocky Mountain spotted fever. Facultative intracellular parasites can reproduce either intracellular or extracellular. Some non-limiting examples of facultative intracellular parasites include *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis.

Finally, bacterial infections could be targeted to a specific location in or on the body. For example, bacteria could be harmless if only exposed to the specific organs, but when it comes in contact with a specific organ or tissue, the bacteria can begin replicating and cause a bacterial infection.

A. Gram-Positive Bacteria

In some aspects of the present disclosure, the compounds disclosed herein may be used to treat a bacterial infection by a gram-positive bacteria. Gram-positive bacteria contain a thick peptidoglycan layer within the cell wall which prevents the bacteria from releasing the stain when dyed with crystal violet. Without being bound by theory, the gram-positive bacteria are often more susceptible to antibiotics. Generally, gram-positive bacteria, in addition to the thick peptidoglycan layer, also comprise a lipid monolayer and contain teichoic acids which react with lipids to form lipoteichoic acids that can act as a chelating agent. Additionally, in gram-positive bacteria, the peptidoglycan layer is outer surface of the bacteria. Many gram-positive bacteria have been known to cause disease including, but are not limited to, *Streptococcus, Straphylococcus, Corynebacterium, Enterococcus, Listeria, Bacillus, Clostridium, Rathybacter, Leifsonia*, and *Clavibacter.*

B. Gram-Negative Bacteria

In some aspects of the present disclosure, the compounds disclosed herein may be used to treat a bacterial infection by a gram-negative bacteria. Gram-negative bacteria do not retain the crystal violet stain after washing with alcohol. Gram-negative bacteria, on the other hand, have a thin peptidoglycan layer with an outer membrane of lipopolysaccharides and phospholipids as well as a space between the peptidoglycan and the outer cell membrane called the periplasmic space. Gram-negative bacterial generally do not have teichoic acids or lipoteichoic acids in their outer coating. Generally, gram-negative bacteria also release some endotoxin and contain prions which act as molecular transport units for specific compounds. Most bacteria are gram-negative. Some non-limiting examples of gram-negative bacteria include *Bordetella, Borrelia, Burcelia, Campylobacteria, Escherichia, Francisella, Haemophilus, Helico-*

*bacter, Legionella, Leptospira, Neisseria, Pseudomonas, Rickettsia, Salmonella, Shigella, Treponema, Vibrio*, and *Yersinia*.

C. Gram-Indeterminate Bacteria

In some aspects of the present disclosure, the compounds disclosed herein may be used to treat a bacterial infection by a gram-indeterminate bacteria. Gram-indeterminate bacteria do not full stain or partially stain when exposed to crystal violet. Without being bound by theory, a gram-indeterminate bacteria may exhibit some of the properties of the gram-positive and gram-negative bacteria. A non-limiting example of a gram-indeterminate bacteria include *Mycobacterium tuberculosis* or *mycobacterium leprae*.

III. Hyperproliferative Diseases

A. Cancer and Other Hyperproliferative Disease

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the trioxacarcin and derivatives thereof may be used to lead to decreased cell counts and as such can potentially be used to treat a variety of types of cancer lines. In some aspects, it is anticipated that the trioxacarcin and derivatives thereof of the present disclosure may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

IV. Cell Targeting Moieties

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example is the cell targeting agents described in U.S. Patent Publication No. 2004/005647 and in Winthrop et al. (2003) that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that bind to the Fn14 receptor, such as TWEAK (see, e.g., Winkles, 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

V. Therapies

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration trioxacarcin and derivatives thereof of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

In particular, the compositions that may be used in treating microbial infections and cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (complete blood count—CBC), or cancer cell growth or proliferation. In some embodiments, amounts of the trioxacarcin derivatives used to inhibit bacterial growth or induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the new derivatives of trioxacarcin may be more efficacious and thus a smaller dose is required to achieve a similar effect. Such a dose is typically administered once a day for a few weeks or until sufficient reducing in cancer cells has been achieved.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the invention provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the trioxacarcin derivatives described herein may be used in combination therapies with an additional antimicrobial agent such as an antibiotic or a compound which mitigates one or more of the side effects experienced by the patient.

Furthermore, it is very common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, trioxacarcin derivatives of the present disclosure may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Agents or factors suitable for use in a combined therapy with agents according to the present disclosure against an infectious disease include antibiotics such as penicillins, cephalosporins, carbapenems, macrolides, aminoglycosides, quinolones (including fluoroquinolones), sulfonamides and tetracylcines. Other combinations are contemplated. The following is a general discussion of antibiotic, antiviral, and cancer therapies that may be used combination with the compounds of the present disclosure.

1. Antibiotics

The term "antibiotics" are drugs which may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

The first commercially available antibiotic was released in the 1930's. Since then, many different antibiotics have been developed and widely prescribed. In 2010, on average, 4 in 5 Americans are prescribed antibiotics annually. Given the prevalence of antibiotics, bacteria have started to develop resistance to specific antibiotics and antibiotic mechanisms. Without being bound by theory, the use of antibiotics in combination with another antibiotic may modulate resistance and enhance the efficacy of one or both agents.

In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug which acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim.

2. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

3. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

4. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance antitumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

5. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurrence of the tumor. Additionally, the compounds of the present disclosure can also be used in a neoadjuvant setting.

6. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

VI. Synthetic Methods

In some aspects, the compounds of this invention can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of trioxacarcin and derivatives thereof.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfato" means —SO$_3$H, "sulfamido" means —S(O)$_2$NH$_2$, "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⹀" represents a single bond or a double bond. Thus, for example, the formula

includes

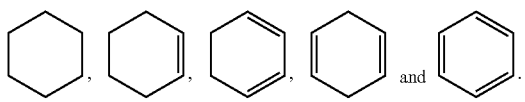

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⦀" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

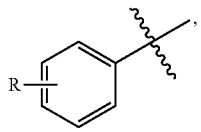

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

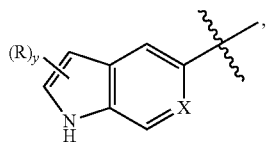

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH₂CH₃), and =C(CH₃)₂. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted alkyl groups: —CH₂OH, —CH₂Cl, —CF₃, —CH₂CN, —CH₂C(O)OH, CH₂C(O)OCH₃, CH₂C(O)NH₂, CH₂C(O)CH₃, —CH₂OCH₃, CH₂OC(O)CH₃, CH₂NH₂, —CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH₂)₂ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

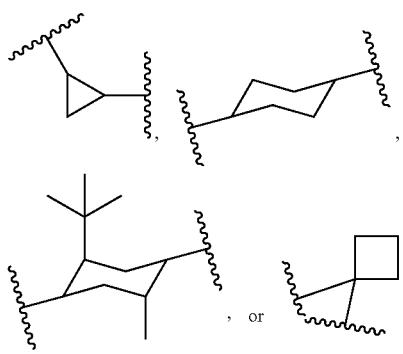

are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted cycloalkyl groups: —C(OH)(CH₂)₂,

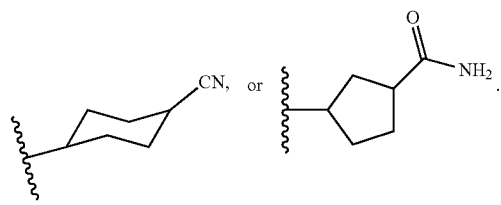 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, and —CH=CHCH₂—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —CH=CHF, —CH=CHCl and —CH=CHBr, are non-limiting examples of substituted alkenyl groups.

The term "cycloalkenyl" when used without the "substituted" modifier refers to a monovalent unsaturated aliphatic group with a carbon atom as the point of attachment, said carbon atom forms part of one or more non-aromatic ring structures, a cyclo or cyclic structure, at least one non-aromatic carbon-carbon double bond, no carbon-carbon triple bonds, and no atoms other than carbon and hydrogen. In some non-limiting examples of cycloalkenyl groups include

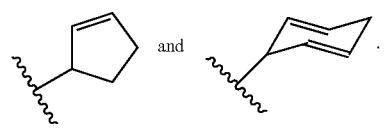 [SMILES: *C1C=CCC1 ; *C1C=CCC=C1]

The term "cycloalkenediyl" when used without the "substituted" modifier refers to a divalent unsaturated aliphatic group with one or two carbon atom(s) as the point(s) of attachment, said carbon atom(s) forms part of one or more non-aromatic ring structures, a cyclo or cyclic structure, at least one non-aromatic carbon-carbon double bond, no carbon-carbon triple bonds, and no atoms other than carbon and hydrogen.

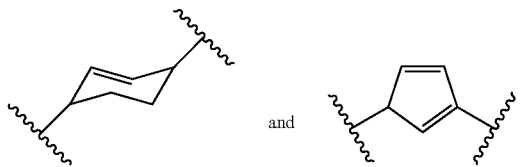 [SMILES: *C1C=CC(*)CC1 ; *C1=CC(*)C=C1]

are non-limiting examples of cycloalkenediyl. It is noted that while the cycloalkenediyl group is aliphatic, once connected at both ends, this group is not precluded from forming part of an aromatic structure. The terms "cycloalkene" and refer to a compound having the formula H—R, wherein R is cycloalkenyl as this term is defined above. The term "olefin" is synonymous with the terms "alkene" or a "cycloalkane" as those terms are defined above. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some non-limiting examples of substituted cycloalkenyl include

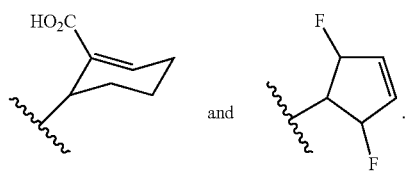 [SMILES: *C1CCCC=C1C(=O)O ; *C1C(F)C=CC1F]

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

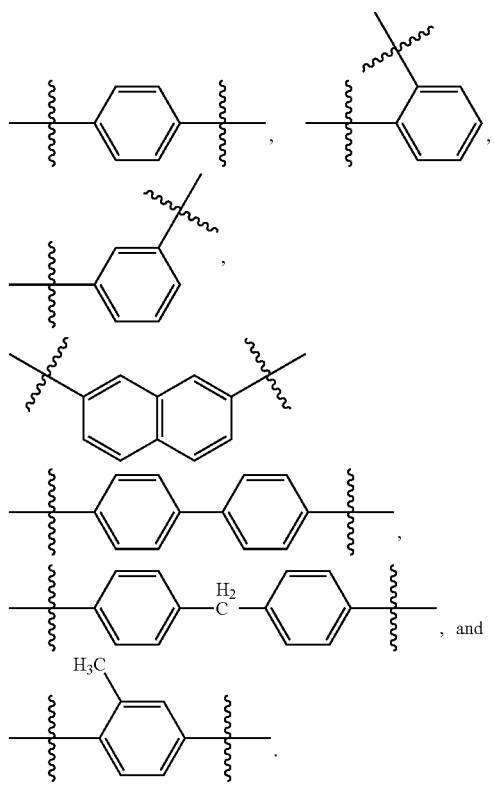

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

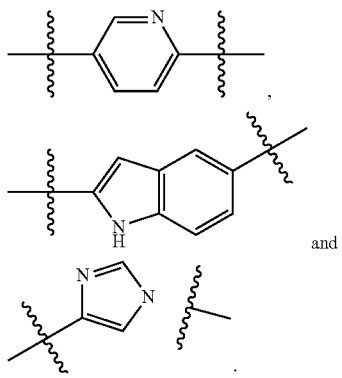

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: 2-pyridylmethyl and 2-indazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH₂, —N₃, —NO₂, —CO₂H, —CO₂CH₃, —CN, —SH, —OCH₃, —OCH₂CH₃, —C(O) CH₃, —NHCH₃, —NHCH₂CH₃, —N(CH₃)₂, —C(O)NH₂, —OC(O)CH₃, or —S(O)₂NH₂. Non-limiting examples of substituted heteroaralkyls are: (3-chloroquinolyl)-methyl, and 2-chloro-2-thienyl-eth-1-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

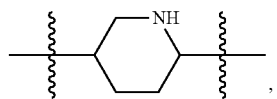

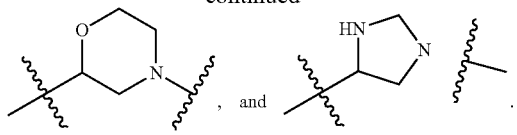, and

When these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, C(O)CH(CH$_2$)$_2$, C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-.

When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula alkyl$_{(C \leq 12)}$-Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine. A metal alkoxide is an alkoxy group wherein the oxygen atom, which was the point of connectivity, has an extra electron and thus a negative charge which is charged balanced by the metal ion. For example, a metal alkoxide could be a sodium tert-butoxide or potassium methoxide.

An "oxidizing agent" in the context of this application is a compound which causes the oxidation of a compound by accepting an electron. Some non-limiting examples of oxidizing agent are oxygen gas, peroxides, chlorite, hypochlorite, or a chromium compound such as pyridinium chlorochromate or hydrochromic acid.

A "metal" in the context of this application is a transition metal or a metal of groups I or II. It may also be an element of Group 13 such as, but not limited to, boron and aluminum.

A "Lewis acid" is a atom or functional group which can accept a pair of electrons. In some embodiments, the Lewis acid is a metal atom. Without being bound by any theory, the Lewis acid increases the reactivity of one or more group to which it attached by increasing the polarization of a bond.

A "linker" in the context of this application is divalent chemical group which may be used to join one or more molecules to the compound of the instant disclosure. In some embodiments, the linker contains a reactive functional group, such as a carboxyl, an amide, a amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$— wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth).

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxy carbonyl, fluorenyl-9-methoxy carbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxy carbonyl, fluorenyl-9-methoxy carbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Synthesis of Trioxacarcin and Analogs Thereof

Figure 2:
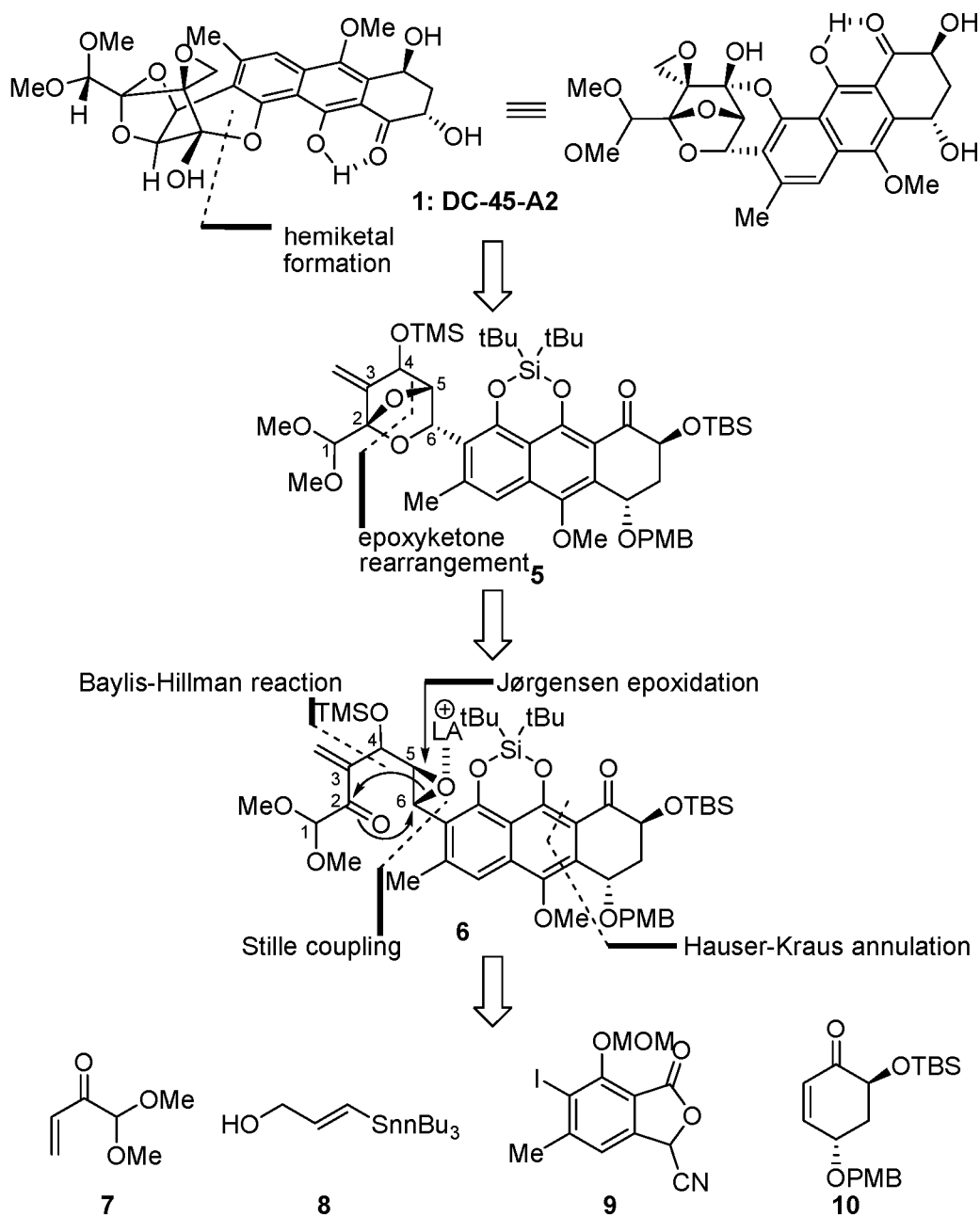
FIG. 2—Retrosynthetic analysis of trioxacarcin DC-45-A2 (1). TBS=tert-butyldimethylsilyl, PMB=p-methoxybenzyl, TMS=trimethylsilyl, MOM=methoxymethyl.
Figure 3A:
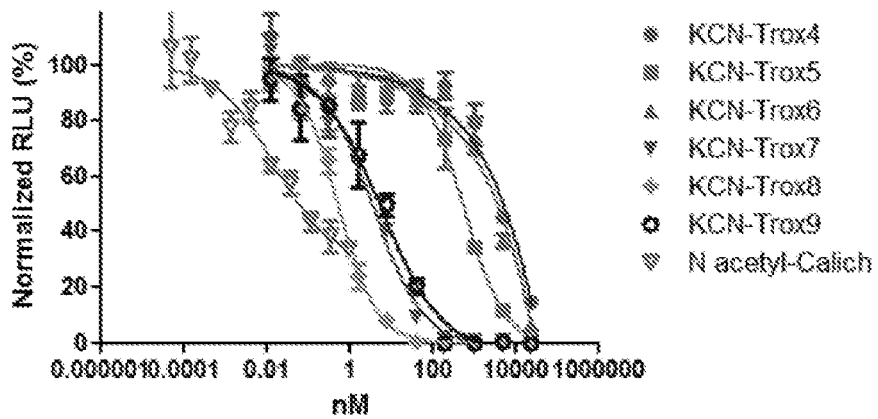
FIGS. 3A-3C—Graph of luminescence as a function of compound concentration for Trox4-Trox9 in cytotoxicity assay for (FIG. 3A) MES SA, (FIG. 3B) MES SA DX, and (FIG. 3C) 293T.
Figure 3B:
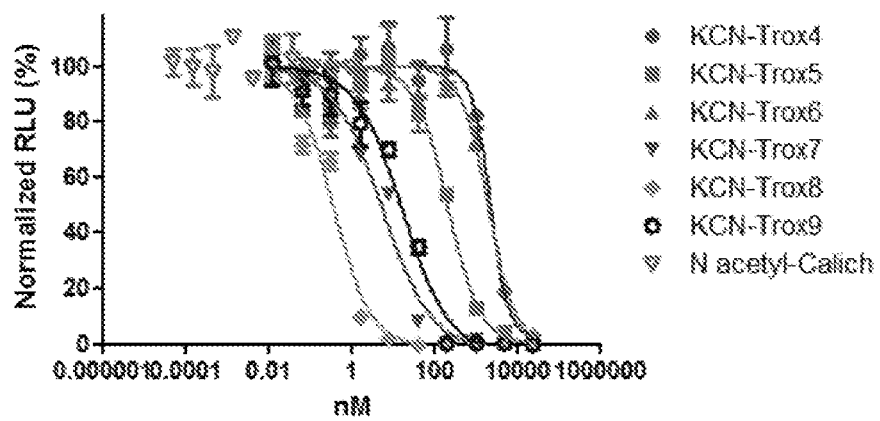
Figure 3C:
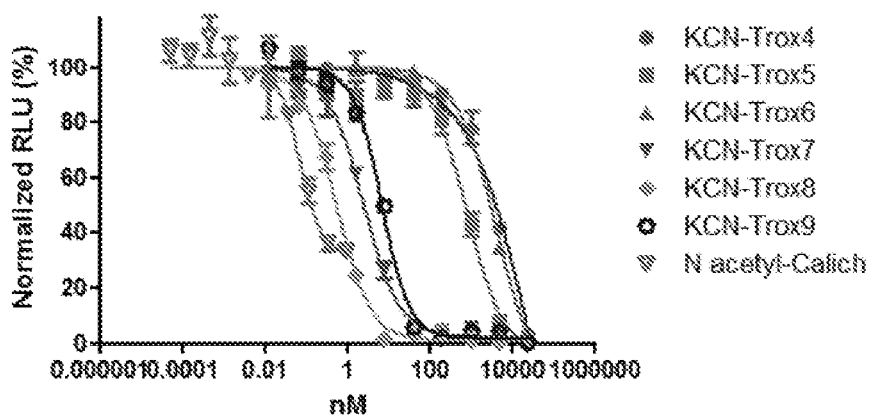
Figure 4A:
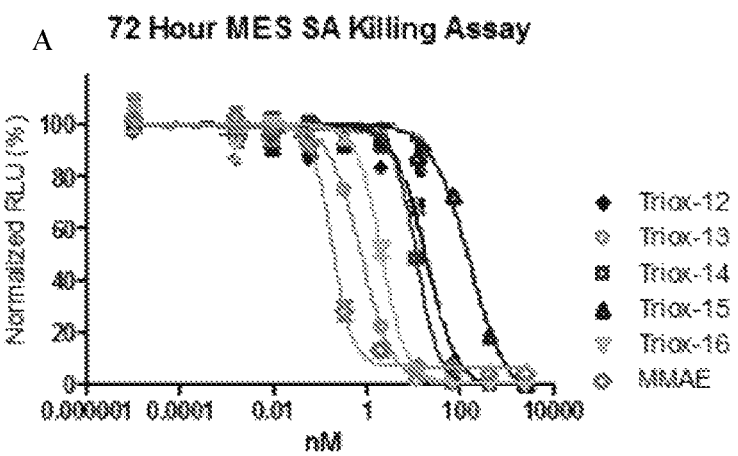
FIGS. 4A-4C—Graph of luminescence as a function of compound concentration for Trox12-Trox16 in cytotoxicity assay for (FIG. 4A) MES SA, (FIG. 4B) MES SA DX, and (FIG. 4C) 293T.
Figure 4B:
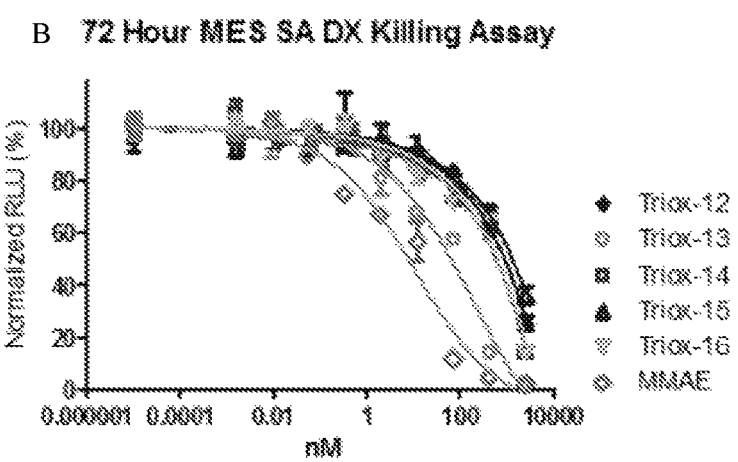
Figure 4C:
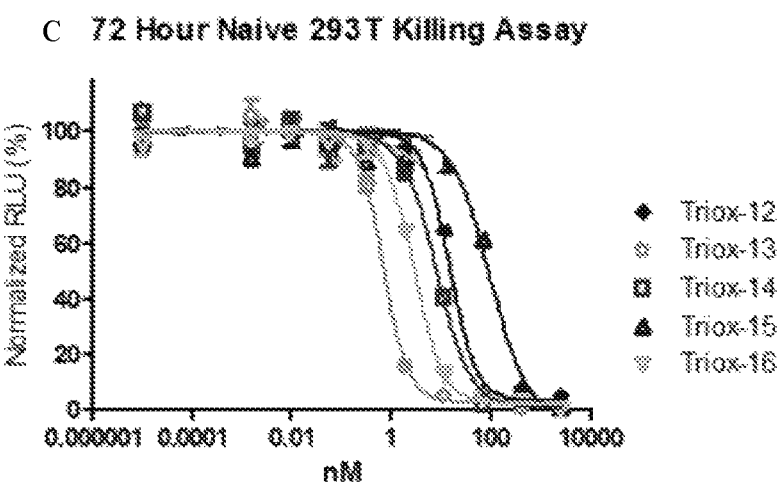

The polyoxygenated 2,7-dioxabicyclo[2.2.1]heptane system of the trioxacarcins is a most intriguing structural motif requiring special attention with regard to strategy and experimentation for its construction. FIG. 2 presents, in one embodiment, a designed strategy toward DC-45-A2 (1) in retrosynthetic format. Thus, disconnection of the hemiacetal moiety of 1 followed by functional group transformations led to advanced precursor 5, whose conversion to the target molecule could be envisioned through sequential and selective deprotection/oxidations. Dismantling of the bicyclo [2.2.1]heptane system within 5 through an epoxyketone rearrangement (Gaoni, 1968; Waserman et al., 1969; Wasserman et al., 1986a; Wasserman et al., 1986b; Wasserman et al., 1988a; Wasserman et al., 1988b; Naruse et al., 1988a; Naruse et al., 1988b; Evans et al., 1991) revealed epoxyketone 6 as a precursor, whose origin could be traced back to key building blocks 7-10 through the disconnections indicated in FIG. 2 [e.g. a) Hauser-Kraus annulation; b) Stille reaction; c) asymmetric Jorgensen epoxidation; and d) Baylis-Hillman reaction]. The key epoxyketone rearrangement (6→5, FIG. 2) was presumed to be inducible in a stereo- and regioselective manner through the action of a suitable monodentate Lewis acid that would involve inversion of configuration at C6, as indicated in FIG. 2 (see arrows on structure 6).

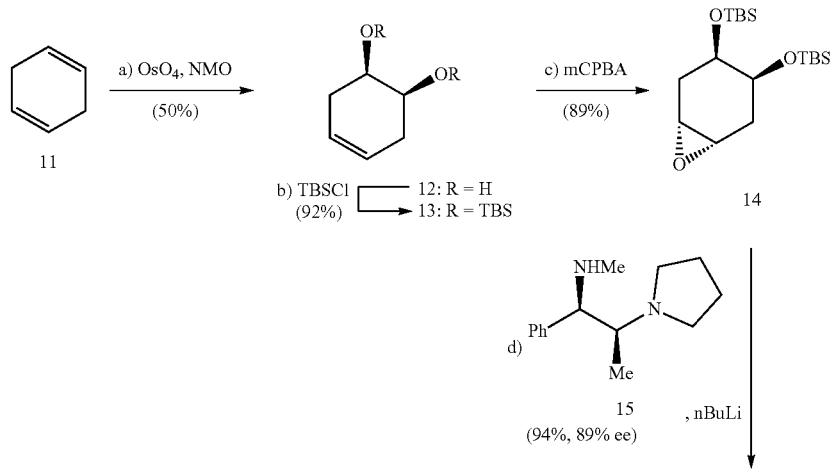

Scheme 1. Synthesis of key building block 10.

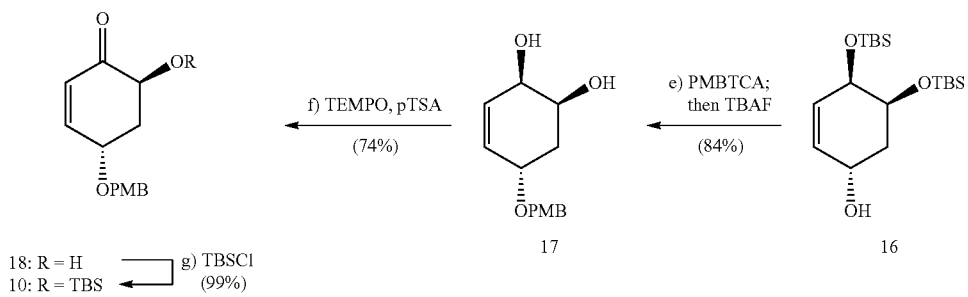

Reagents and conditions: a) OsO$_4$ (4% w/v aq. solution, 0.02 equiv), NMO (1.0 equiv), acetone, 25° C., 72 h, 50%; b) TBSCl (2.4 equiv), imidazole (5.0 equiv), CH$_2$Cl$_2$, 25° C., 48 h, 92%; c) mCPBA (1.4 equiv), NaHCO$_3$ (2.0 equiv), cyclohexane, 25° C., 17 h, 89%; d) 15 (2.0 equiv), nBuLi (2.0 equiv), THF, 0→25° C., 18 h, 94%, 89% ee; e) PMBTCA (2.5 equiv), TrBF$_4$ (0.05 equiv), THF, 25° C., 1 h; then TBAF (7.0 equiv), THF, 66° C., 4 h, 84%; f) TEMPO (3.0 equiv), pTSA (3.0 equiv), CH$_2$Cl$_2$, 0° C., 45 min, 74%; g) TBSCl (1.8 equiv), imidazole (3.0 equiv), CH$_2$Cl$_2$, 25° C., 1.5 h, 99%. NMO = N-methylmorpholine-N-oxide, TBSCl = t-butyldimethylsilyl chloride, mCPBA = meta-chloroperoxybenzoic acid, PMBTCA = 4-methoxybenzyl-2,2,2-trichloroacetimidate, TrBF$_4$ = trityltetrafluoroborate, TBAF = tetra-n-butylammonium fluoride, TEMPO = 2,2,6,6-tetramethyl-1-piperidinyloxy, pTSA = para-toluenesulfonic acid, THF = tetrahydrofuran.

The required cyclohexenone 10 was prepared enantioselectively from cyclohexadiene 11, as summarized in Scheme 1. Thus, 11 was subjected to Upjohn dihydroxylation (OsO$_4$ cat., NMO, 50% yield) and the resulting diol 12 was silylated to afford bis-TBS ether 13 (TBSCl, 92% yield). Epoxidation of the latter (mCPBA, 89% yield) led selectively to epoxide 14, whose regioselective opening with (−)-norephedrine-derived amine 15 in the presence of nBuLi furnished allylic alcohol 16 in 94% yield and 89% ee (Maras et al., 1998; O'Brien et al., 1998; Coleman et al., 1999; deSousa et al., 2002). Protection of this alcohol with 4-methoxybenzyl-2,2,2-trichloroacetimidate (PMBTCA) followed by TBAF-induced desilylation led to PMB-ether diol 17 in 84% yield. Selective oxidation of the allylic alcohol of the latter (TEMPO, pTSA, 74% yield) (Banwell et al., 1994) furnished hydroxyenone 18, whose silylation (TBSCl, 99% yield) led to the targeted key building block enone 10.

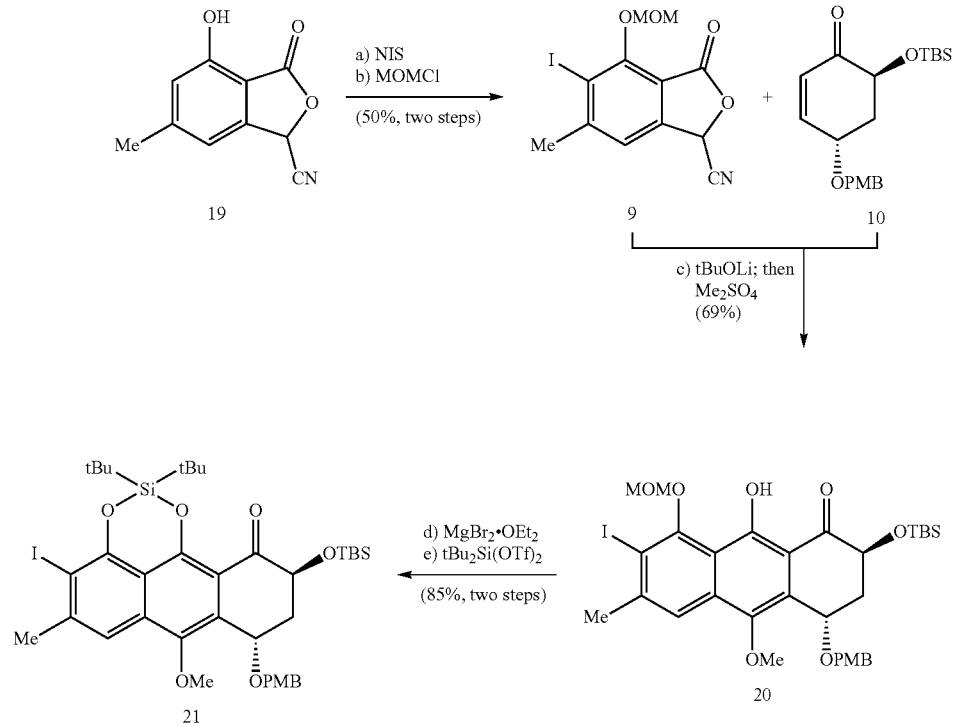

Reagents and conditions: a) NIS (1.4 equiv), DCE, -10° C., 6 h; b) MOMCl (1.3 equiv), DIPEA (3.0 equiv), CH$_2$Cl$_2$, 25° C., 6 h, 50% over two steps; c) 9 (1.0 equiv), 10 (1.0 equiv) tBuOLi (3.0 equiv), THF, -78° C., 0.5 h; then Me$_2$SO$_4$ (10 equiv), 0° C., 5 h, 69%; d) MgBr$_2$•OEt$_2$ (3.0 equiv), THF, 0° C., 15 min; e) tBu$_2$Si(OTf)$_2$ (1.2 equiv), 2,6-lutidine (2.5 equiv), DMF, 0° C., 0.5 h, 85% over two steps. NIS = N-iodosuccinimide, DCE = 1,2-dichloroethane, DIPEA = N,N-diisopropylethylamine, DMF = N,N-dimethylformamide.

Enone 10 was coupled with the easily accessible iodocyanophthalide derivative 9 through a Hauser-Kraus annulation, (Hauser et al., 1978; Kraus et al., 1978) and the product was elaborated to intermediate 21 as shown in Scheme 2. Thus, iodocyanophthalide 9 [prepared from the known cyanophthalide 19 (Nicolaou et al., 2009) by sequential iodination (NIS) and MOM protection (MOMCl, DIPEA, 50% overall yield)] was reacted with enone 10 in the presence of tBuOLi (−78° C.) (Švenda et al., 2011; Magauer et al., 2013; Nicolaou et al., 2009) and the resulting p-dihydroquinone derivative was selectively methylated with $Me_2SO_4$ to afford tricyclic system 20 in 69% overall yield. Removal of the MOM group from the latter intermediate with $MgBr_2 \cdot OEt_2$, (Yang et al., 2009) followed by treatment with $tBu_2Si(OTf)_2$ and 2,6-lutidine then gave silylated product 21 in 85% overall yield.

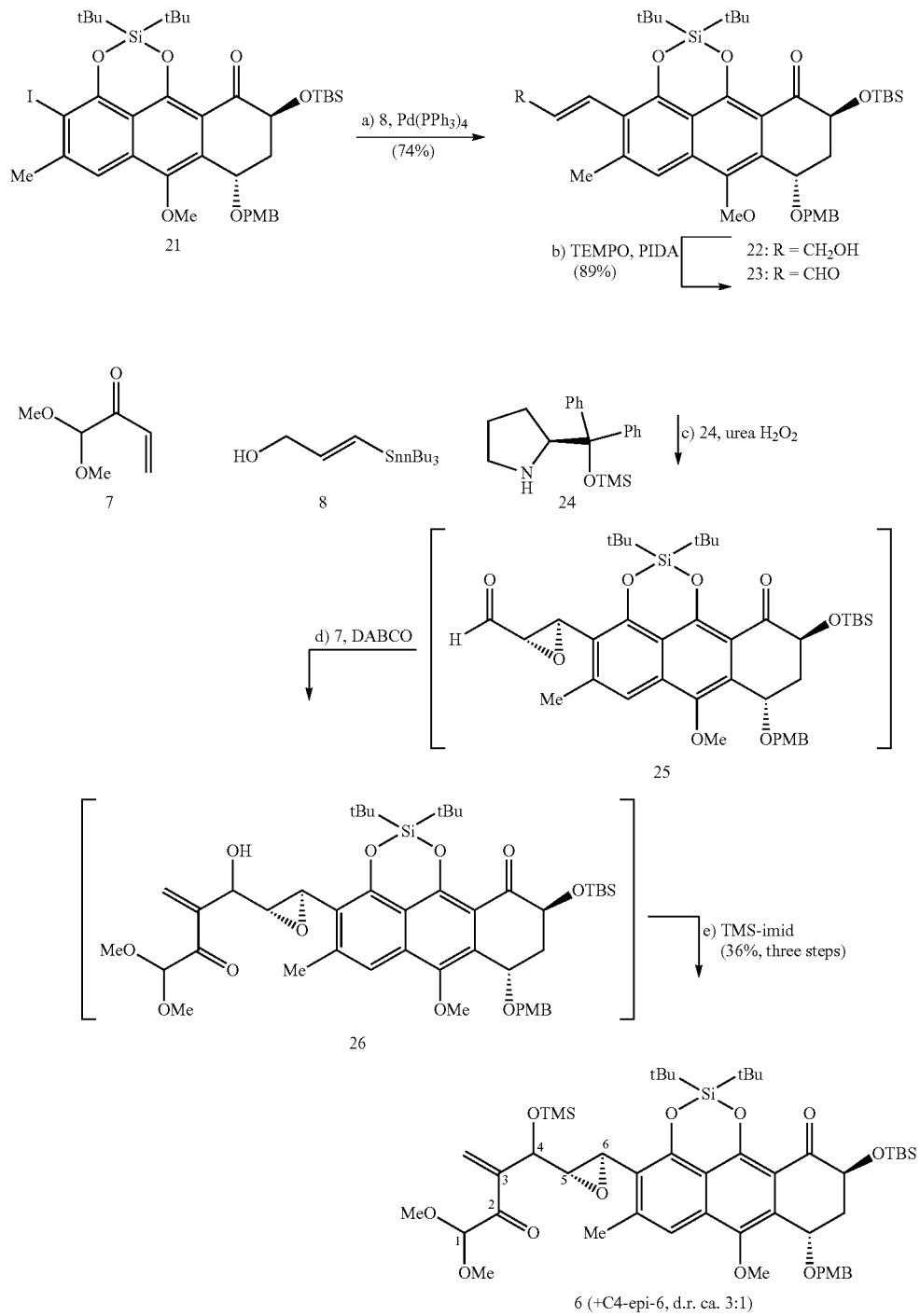

Scheme 3. Synthesis of bis-cyclization precursor epoxyketone 6.

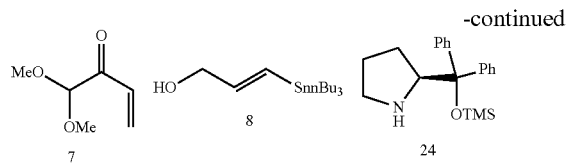

Reagents and conditions:
a) Pd(PPh₃)₄ (0.2 equiv), 8 (3.0 equiv), CuTC (1.2 equiv), DMF:THF 1:1, 85° C., 12 h, 74%;
b) TEMPO (0.1 equiv), PIDA (1.3 equiv), CH₂Cl₂, 25° C., 4 h, 89%;
c) 24 (0.2 equiv), urea•H₂O₂ (7.0 equiv), CHCl₃:H₂O 20:1, 25° C., 7 h;
d) 7 (10 equiv), DABCO (0.5 equiv), 4-nitrophenol (0.5 equiv), THF, 25° C., 12 h;
e) TMS-imid (1.0 equiv), CH₂Cl₂, 25° C., 0.5 h, 36% over three steps, d.r. ca. 3:1 at C4.
CuTC = copper(I)-thiophene-2-carboxylate, PIDA = iodobenzene diacetate,
DABCO = 1,4-diazabicyclo[2.2.2]octane, TMS-imid = N-trimethylsilylimidazole.

Intermediate 21 was advanced to the key cyclization precursor 6, as summarized in Scheme 3. Thus, Stille coupling of aryl iodide 21 with stannane 8 (Pilli et al., 1998) proceeded in the presence of CuTC and catalytic amounts of Pd(PPh₃)₄ (Pulukuri et al., 2012) to afford allylic alcohol 22 (74% yield), whose oxidation with TEMPO and PIDA gave aldehyde 23 (89% yield). Jorgensen asymmetric epoxidation of α,β-unsaturated aldehyde 23 (24 cat., urea.H₂O₂) (Marigo et al., 2005) led to epoxyaldehyde 25, which was subjected without purification to Baylis-Hillman reaction with enone 7 (Edwards et al., 2003) (DABCO, 4-nitrophenol) to give labile hydroxyepoxide 26. The latter was immediately protected with N-trimethylsilylimidazole (TMS-imid) to furnish the targeted precursor 6 (+C4-epi-6, d.r. ca. 3:1) in 36% yield over the three steps.

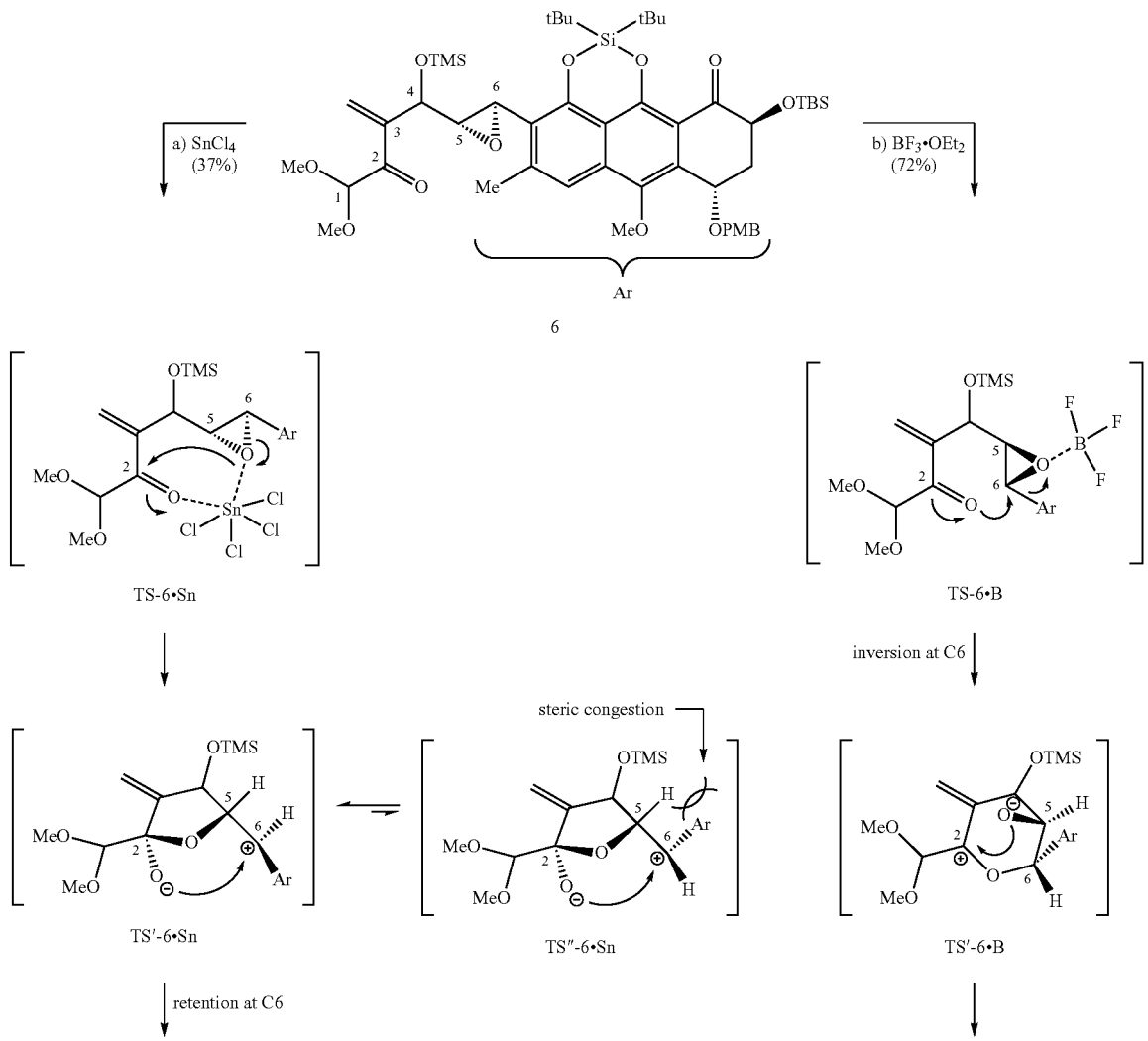

Scheme 4. Bis-cyclization of precursor epoxyketone 6.

-continued

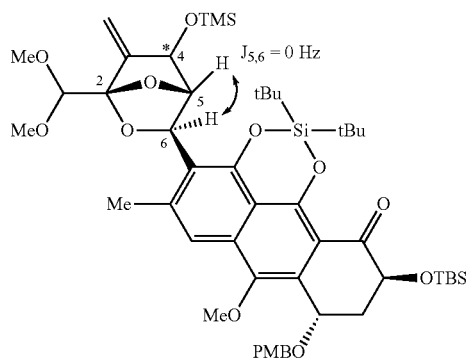
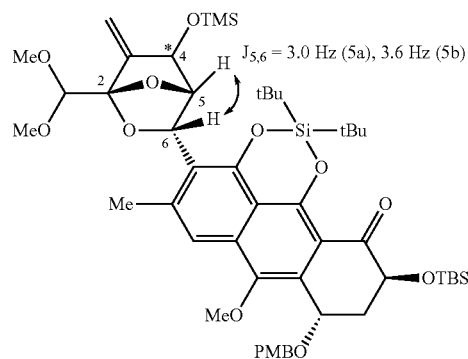

27 (+C4-epi-27: d.r. ca. 13:1, 37%)        5a (54%), 5b (C4-epi-5a, 18%)

Reagents and conditions: a) SnCl$_4$ (0.05 equiv), CH$_2$Cl$_2$, -78° C., 1 h, d.r. ca. 13:1 at C4, 37%; b) BF$_3$·OEt$_2$ (0.3 equiv), CH$_2$Cl$_2$, -78° C., 3 h, 54% (5a), 18% (5b).

With the penultimate bis-cyclization precursor 6 in hand, the stage was now set for the coveted cascade ring closures to forge the targeted 2,7-dioxabicyclo[2.2.1]heptane system of the growing molecule. To this end, and as shown in Scheme 4, epoxyketone 6 (ca. 3:1 mixture of C4-diastereoisomers) was reacted with catalytic amounts of BF$_3$.OEt$_2$ (monodentate Lewis acid) in CH$_2$Cl$_2$ at −78° C., furnishing the desired product as a mixture of C4-diastereoisomers (d.r. ca. 3:1) (5a, C4-α-diastereoisomer, 54% yield; 5b, C4-β-diastereoisomer, 18% yield). The assignments of the C4 and C6 configurations of diastereoisomers 5a and 5b were based on their H4, H5, H6 coupling constants (5a: $J_{4,5}$=4.8 Hz, $J_{5,6}$=3.0 Hz; 5b: $J_{4,5}$=0 Hz, $J_{5,6}$=3.6 Hz). (Padwa et al., 1991; Kraehenbuehl et al., 1995; Kraehenbuehl et al., 1998; Muthusamy et al., 2002). Both compounds were obtained as single diastereoisomers at C6 (inverted configuration). The reaction is presumed to proceed through transition states TS-6•B and TS'-6•B as shown in Scheme 4. In contrast, reaction of substrate 6 with catalytic amounts of bidentate Lewis acid SnCl$_4$ in CH$_2$Cl$_2$ at −78° C. led to the opposite diastereoisomers at C6 ($J_{5,6}$=0 Hz), 27 (+C4-epi-27) (37% yield, d.r. ca. 13:1). This reaction is presumed to proceed through transition states TS-6•Sn and TS'-6•Sn, the latter being favored over its more sterically congested alternative conformer TS"-6•Sn that would have led to inversion of configuration at C6 (see Scheme 4). These results support the proposed monodentate Lewis acid-catalyzed epoxyketone rearrangement upon which the strategy for the construction of the dioxabicyclo[2.2.1]heptane structural motif possessing the desired configurations was based.

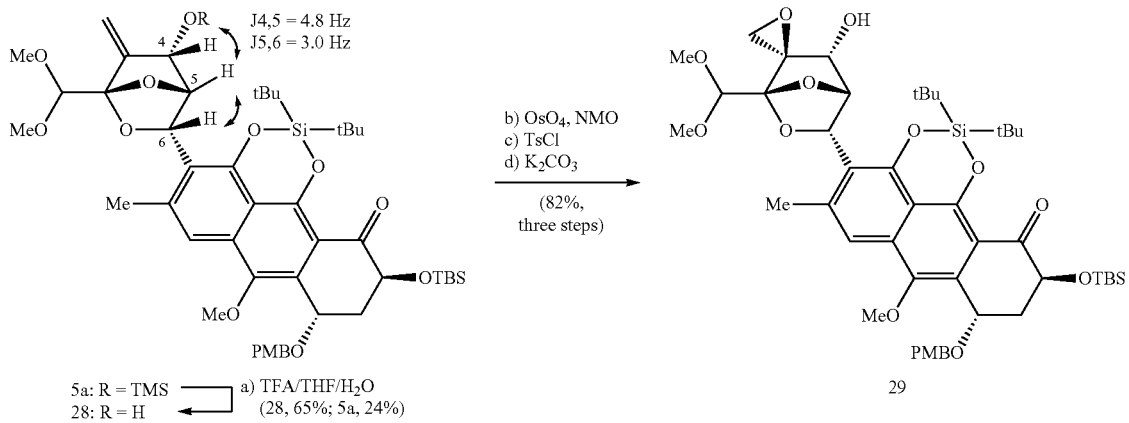

Scheme 5. Completion of the total synthesis of trioxacarcin DC-45-A2 (1).

-continued

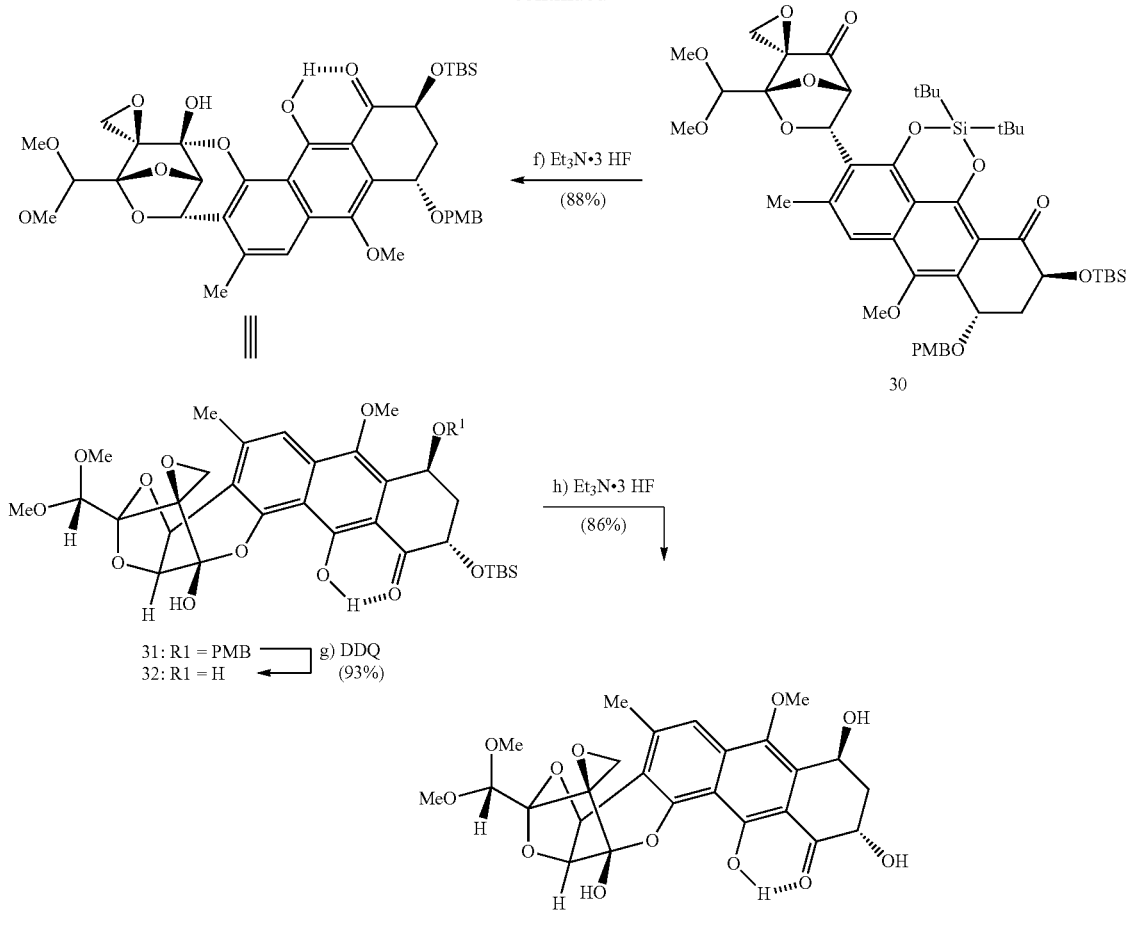

Reagents and conditions: a) TFA (0.1M, 10 equiv), THF:H₂O 5:1, 25° C., 6 h, 65% and recovered 5a, 24%; b) OsO₄ (4% w/v/ aq. solution, 0.2 equiv), NMO (0.48M aq. solution, 4.0 equiv), acetone, 25° C., 12 h; c) TsCl (5.0 equiv), Et₃N (10 equiv), DMAP (0.2 equiv), CH₂Cl₂, 0→25° C., 5 h; d) K₂CO₃, (2.0 equiv), MeOH, 0° C., 3 h, 82% over three steps; e) TPAP (0.2 equiv), NMO•H₂O (3.0 equiv), CH₂Cl₂, 0° C., 2 h, 93%; f) Et₃N•3 HF (3.0 equiv), CH₃CN, 25° C., 15 min, 88%; g) DDQ (2.0 equiv), CH₂Cl₂:H₂O 10:1, 25° C., 1 h, 93%; h) Et₃N•3HF (20 equiv), CH₃CN, 25° C., 13 h, 86%. TFA = trifluoroacetic acid, TsCl = 4-toluenesulfonyl chloride, DMAP = 4-dimethyl-aminopyridine, TPAP = tetrapropylammonium perruthenate, DDQ = 2,3-dichloro-5,6-dicyano-1,4-benzoquinone.

Having succeeded in building the most challenging structural domain of the targeted molecule, the remaining tasks of the synthesis were completed including installation of the epoxide moiety, oxidation at C4, and deprotection. Thus, advanced intermediate 5a (major diastereoisomer) was converted to the targeted natural product (1) as shown in Scheme 5. Thus, selective cleavage of the TMS-ether of 5a gave allylic alcohol 28 (TFA, 65%) and recovered 5a (24% yield). Due to difficulties in obtaining the desired epoxide 29 from 28 through mCPBA or tBuOOH/VO(acac)₂ epoxidations, a three-step process involving diastereoselective Upjohn dihydroxylation of the olefinic bond within 28 (OsO₄ cat., NMO) was used followed by selective monotosylation of the resulting triol (TsCl, Et₃N, DMAP cat.) and epoxide formation (K₂CO₃, MeOH, 82% overall yield). TPAP-catalyzed oxidation of hydroxyepoxide 29 led to ketoepoxide 30 (93% yield), which could be sequentially and selectively deprotected to afford trioxacarcin derivatives 31 (Et₃N.3HF, 3.0 equiv, 15 min, 88% yield) and 32 (DDQ, 93% yield). Finally, trioxacarcin DC-45-A2 (1) was liberated from its TBS-ether 32 by exposure to Et₃N.3HF (excess, 13 h, 86% yield). Synthetic 1 exhibited identical physical properties (i.e., $^1$H and $^{13}$C NMR and mass spectra) to those reported in the literature (Shirahata et al., 1984; Švenda et al., 2011).

Example 2—General Methods and Materials

All reactions were carried out under an argon atmosphere with dry solvent under anhydrous conditions, unless otherwise noted. Dry acetonitrile (CH₃CN), N,N-dimethylformamide (DMF), methanol, dichloromethane (CH₂Cl₂), triethylamine (Et₃N) and tetrahydrofuran (THF) were obtained by passing commercially available pre-dried, oxygen-free formulations through activated alumina columns. Anhydrous acetone, cyclohexane, chloroform (CHCl₃) and 1,2-dichloroethane (DCE) were purchased from commercial suppliers and stored under argon. Yields refer to chromatographically and spectroscopically ($^1$H NMR) homogenous material, unless otherwise stated. Reagents were purchased at the highest commercial quality and used without further purification, unless otherwise noted. Reactions were monitored by thin-layer chromatography (TLC) carried out on 0.25 mm E. Merck silica gel plates (60F₂₅₄) using UV light as visualizing agent or an aqueous solution of phosphomolybdic acid and cerium sulfate or a basic aqueous solution of potassium permanganate and heat as developing agents. Acros Organics silica gel (60, particle size 0.035-0.070 mm) was used for flash column chromatography.

NMR spectra were recorded on a Bruker Avance III HD 600 MHz instrument equipped with a 5 mm DCH cryoprobe and calibrated using residual undeuterated solvent (CDCl$_3$, $\delta_H$=7.26 ppm, $\delta_C$=77.00 ppm) as an internal reference at 298 K. The following abbreviations were used to designate multiplicities: s=singlet, d=doublet, t=triplet, q=quartet, m=multiplet, br=broad. Infrared (IR) spectra were recorded on a Perkin-Elmer 100 FT-IR spectrometer. High-resolution mass spectra (HRMS) were recorded on an Ion Trap-Time of Flight Mass Spectrometer (Shimadzu, Columbia, Md.) operated with an ESI source interface and a VG ZAB-ZSE mass spectrometer using MALDI (matrix-assisted laser-desorption ionization) or ESI (electrospray ionization). Optical rotations were recorded on a Schmidt+Haensch Polartronic M100 polarimeter at 589.44 nm using 100 mm cells and the solvent and concentration indicated.

Example 3—Compound Characterization

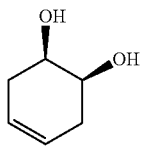

Diol 12:

To a stirred solution of N-methylmorpholine-N-oxide (42.2 g, 312 mmol) in acetone (780 mL) at 25° C. were added 1,4-cyclohexadiene (25.0 g, 312 mmol, 1.0 equiv) and OsO$_4$ (4% w/v aq. solution, 39.7 mL, 6.24 mmol, 0.02 equiv), and the resulting black suspension was stirred at this temperature for 72 h. Na$_2$SO$_3$ (25.0 g) was then added and the resulting mixture was stirred at 25° C. for another 1 h. The mixture was dried over anhydrous MgSO$_4$ and concentrated under reduced pressure. The residue was filtered through a short pad of silica gel, rinsed with EtOAc and concentrated to give the title compound (12, 17.9 g, 157 mmol, 50%) as a colorless solid. 12: R$_f$=0.23 (silica gel, EtOAc); m.p. 71-72° C. (EtOAc); FT-IR (neat): $\nu_{max}$=3292, 3022, 2906, 1649, 1433, 1371, 1331, 1079, 1057, 1049, 975, 895, 755, 662 cm$^{-1}$; $^1$H NMR (CDCl$_3$, 600 MHz) $\delta$=5.58 (t, J=1.8 Hz, 2H), 3.94 (t, J=6.0 Hz, 2H), 2.36 (dd, J=6.0, 16.2 Hz, 2H), 2.25 (dd, J=16.2, 6.0 Hz, 2H), 2.20 (br s, 1H), 2.17 (br s, 1H) ppm; $^{13}$C NMR (CDCl$_3$, 150 MHz) $\delta$=123.7, 68.9, 31.0 ppm; HRMS (ESI-TOF) calcd for C$_6$H$_{10}$NaO$_2^+$ [M+Na]$^+$ 137.0573, found 137.0572. All spectroscopic data were consistent with those in the literature. (Mara et al., 1998)

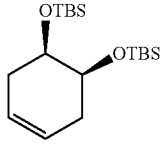

Bis-TBS Ether 13:

To a stirred solution of diol 12 (6.27 g, 54.9 mmol) in CH$_2$Cl$_2$ at 25° C. were added imidazole (18.7 g, 274 mmol, 5.0 equiv) and TBSCl (19.9 g, 132 mmol, 2.4 equiv). After stirring at this temperature for 48 h, the reaction mixture was washed with water (2×100 mL), whereupon the combined aqueous layers were extracted with CH$_2$Cl$_2$ (5×100 mL). The combined organic phases were dried over anhydrous MgSO$_4$ and concentrated under reduced pressure. The crude mixture was purified by flash column chromatography (silica gel, EtOAc:hexanes 1:200) to give the title compound (13, 17.4 g, 50.7 mmol, 92%) as a colorless oil. 13: R$_f$=0.37 (silica gel, EtOAc:hexanes 1:100); FT-IR (neat): $\nu_{max}$=2954, 2927, 2894, 2857, 1472, 1373, 1250, 1215, 1121, 1094, 1074, 1006, 827, 772 cm$^{-1}$; $^1$H NMR (CDCl$_3$, 600 MHz) $\delta$=5.50 (t, J=1.8 Hz, 2H), 3.84 (t, J=5.4 Hz, 2H), 2.21 (dd, J=16.2, 6.6 Hz, 2H), 2.13 (dd, J=16.2, 5.4 Hz, 2H), 0.88 (s, 18H), 0.06 (s, 6H), 0.05 (s, 6H) ppm; NMR (CDCl$_3$, 150 MHz) $\delta$=124.1, 70.7, 32.6, 25.9, 18.2, −4.4, −4.9 ppm; HRMS (ESI-TOF) calcd for C$_{18}$H$_{39}$O$_2$Si$_2^+$ [M+H]$^+$ 343.2483, found 343.2474. All spectroscopic data were consistent with those in the literature. (O'Brien et al., 1998)

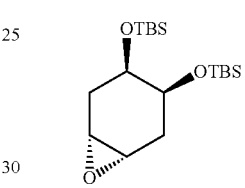

Epoxide 14:

To a stirred solution of bis-TBS ether 13 (16.7 g, 48.8 mmol) in cyclohexane (500 mL) at 25° C. were sequentially added NaHCO$_3$ (8.19 g, 97.5 mmol, 2.0 equiv) and mCPBA (11.8 g, ca. 30% water content, 68.3 mmol, 1.4 equiv) in portions. The reaction mixture was stirred at this temperature for 17 h. After quenching the reaction with Na$_2$SO$_3$ (10% aq., 300 mL), the aqueous layer was extracted with CH$_2$Cl$_2$ (2×400 mL), and the combined organic phases were dried over anhydrous Na$_2$SO$_4$ and concentrated under reduced pressure. The residue was purified by flash column chromatography (silica gel, EtOAc:hexanes 1:30) to give the title compound (14, 15.5 g, 43.2 mmol, 89%) as a colorless oil. 14: R$_f$=0.32 (silica gel, EtOAc:hexanes 1:30); FT-IR (neat): $\nu_{max}$=2952, 2928, 2894, 2856, 1472, 1371, 1250, 1135, 1101, 1076, 998, 956, 879, 827, 805, 773 cm$^{-1}$; $^1$H NMR (CDCl$_3$, 600 MHz) $\delta$=3.67 (t, J=4.8 Hz, 2H), 3.15 (s, 2H), 2.08-2.00 (m, 4H), 0.88 (s, 18H), 0.05 (s, 6H), 0.04 (s, 6H) ppm; $^{13}$C NMR (CDCl$_3$, 150 MHz) $\delta$=68.8, 52.1, 31.3, 25.9, 18.2, −4.5, −4.8 ppm; HRMS (ESI-TOF) calcd for C$_{18}$H$_{39}$O$_3$Si$_2^+$ [M+H]$^+$ 359.2427, found 359.2432. All spectroscopic data were consistent with those in the literature. (O'Brien et al., 1998)

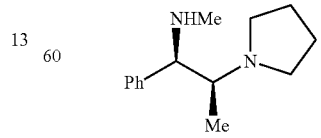

(−)-Norephedrine-Derived Amine 15:

Amine 15 was prepared according to the original procedure. (Colman et al., 1999) 15: R$_f$=0.10 (silica gel, 10%

MeOH in CH$_2$Cl$_2$); [α]$^{25}_D$=−22.8 (c=1.0, CHCl$_3$); $^1$H NMR (CDCl$_3$, 600 MHz) δ=7.36-7.32 (m, 4H), 7.25-7.21 (m, 1H), 3.85 (d, J=3.0 Hz, 1H), 2.64-2.62 (m, 4H), 2.34 (s, 3H), 2.27 (qd, J=6.6, 3.6 Hz, 1H), 1.82-1.80 (m, 4H), 1.70 (br s, 1H), 0.85 (d, J=6.6 Hz, 3H) ppm; $^{13}$C NMR (CDCl$_3$, 150 MHz) δ=141.9, 128.0, 127.9, 126.5, 67.0, 66.3, 52.4, 35.5, 23.5, 13.0 ppm. All spectroscopic data were consistent with those in the literature. (Colman et al., 1999)

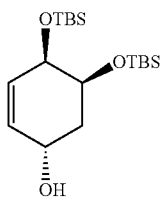

16

Allylic Alcohol 16:

To a stirred solution of (−)-norephedrine-derived amine 15 (4.4 g, 20.2 mmol, 2.0 equiv) in THF (14 mL) at −78° C. was added nBuLi (2.1 M in hexanes, 9.6 mL, 20.2 mmol, 2.0 equiv) dropwise over 20 min. After warming the reaction mixture to 0° C. and stirring at this temperature for 30 min, the reaction was cooled to −78° C. again, and a solution of epoxide 14 (3.6 g, 10.1 mmol) in THF (14 mL) was added dropwise at −78° C. over 20 min. The reaction mixture was allowed to warm to 25° C., stirred at this temperature for 18 h, and then quenched with NH$_4$Cl (sat. aq., 25 mL). The resulting mixture was extracted with Et$_2$O (2×40 mL) and the combined organic phases were washed sequentially with HCl (2% aq., 3×40 mL), NaHCO$_3$ (sat. aq., 2×40 mL) and brine (25 mL), and then dried over anhydrous Na$_2$SO$_4$ and concentrated under reduced pressure. The residue was purified by flash column chromatography (silica gel, EtOAc:hexanes 1:5) to give the title compound (16, 3.4 g, 9.5 mmol, 94%, 19:1 e.r. by Mosher ester analysis—Hoye et al., 2007) as a white solid. 16: R$_f$=0.34 (silica gel, EtOAc:hexanes 1:4); m.p. 56-57° C. (EtOAc, hexanes); [α]$^{25}_D$=−96.3=1.0, CHCl$_3$); FT-IR (neat): ν$_{max}$=3302, 2953, 2929, 2886, 2856, 1472, 1389, 1251, 1118, 1091, 1030, 953, 871, 829, 772, 672 cm$^{-1}$; $^1$H NMR (CDCl$_3$, 600 MHz) δ=5.74 (dd, J=10.1, 2.6 Hz, 1H), 5.64 (dd, J=10.1, 3.1 Hz, 1H), 4.45-4.43 (m, 1H), 4.08-4.06 (m, 1H), 2.27 (ddd, J=13.3, 8.1, 5.3 Hz, 1H), 1.57 (ddd, J=13.2, 6.3, 2.2 Hz, 1H), 1.46 (d, J=3.8 Hz, 1H), 0.90 (s, 9H), 0.89 (s, 9H), 0.08 (s, 3H), 0.08 (s, 3 H), 0.08 (s, 3H), 0.07 (s, 3H) ppm; $^{13}$C NMR (CDCl$_3$, 150 MHz) δ=131.1, 130.3, 69.7, 68.8, 65.9, 37.4, 26.0, 25.9, 18.4, 18.3, −4.4, −4.6, −4.8 ppm; HRMS (ESI-TOF) calcd for C$_{18}$H$_{38}$NaO$_3$Si$_2^+$ [M+Na]$^+$ 381.2252, found 381.2235. All spectroscopic data were consistent with those in the literature. (de Sousa et al., 2002)

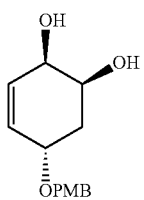

17

PMB-Ether Diol 17:

To a stirred solution of allylic alcohol 16 (17.0 g, 47.4 mmol) in THF (500 mL) 25° C. were added trityltetrafluoroborate (0.782 g, 2.37 mmol, 0.05 equiv) and freshly prepared 4-methoxybenzyl-2,2,2-trichloroacetimidate (PMB-TCA; 33.5 g, 118 mmol, 2.5 equiv). After stirring at this temperature for 1 h, TBAF (1.0 M in THF, 332 mL, 7.0 equiv) was added and the reaction mixture was heated to reflux for 4 h, then cooled to 25° C. and concentrated under reduced pressure. The residue was purified by flash column chromatography (silica gel, acetone:pentane 1:3→3:2) to give the title compound (17, 10.0 g, 40.0 mmol, 84%) as an off-white solid. 17: R$_f$=0.38 (silica gel, acetone:pentane 2:3); m.p. 84-85° C. (acetone, pentane); [α]$^{25}_D$=−135.3 (c=1.0, CHCl$_3$); FT-IR (neat): ν$_{max}$=3373, 3031, 2931, 2837, 1611, 1512, 1388, 1301, 1244, 1172, 1063, 1031, 823 cm$^{-1}$; $^1$H NMR (CDCl$_3$, 600 MHz) δ=7.26 (d, J=8.5 Hz, 2H), 6.87 (d, J=8.5 Hz, 2H), 5.96 (dd, J=10.1, 2.3 Hz, 1H), 5.76 (dd, J=10.1, 2.7 Hz, 1H), 4.52 (d, J=11.3 Hz, 1H), 4.48 (d, J=11.3 Hz, 1H), 4.17-4.13 (m, 3H), 3.79 (s, 3H), 2.50 (s, 1H), 2.18 (ddd, J=13.1, 8.1, 4.9 Hz, 1H), 1.81 (ddd, J=13.4, 6.2, 2.4 Hz, 1H) ppm; $^{13}$C NMR (CDCl$_3$, 150 MHz) δ=159.2, 130.6, 130.4, 129.4, 129.3, 113.8, 70.9, 70.4, 67.4, 66.7, 55.3, 32.7 ppm; HRMS (ESI-TOF) calcd for C$_{14}$H$_{18}$NaO$_4^+$ [M+Na]$^+$ 273.1097, found 273.1086.

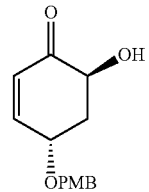

18

Hydroxyenone 18:

To a stirred solution of PMB-ether diol 17 (6.09 g, 24.3 mmol) in CH$_2$Cl$_2$ (290 mL) at 25° C. was added p-toluene sulfonic acid monohydrate (13.9 g, 72.9 mmol, 3.0 equiv). Then a solution of TEMPO (11.4 g, 72.9 mmol, 3.0 equiv) in CH$_2$Cl$_2$ (30 mL) was added via syringe pump over 30 min at 0° C. After stirring at this temperature for another 15 min, the reaction was quenched with NaHCO$_3$ (sat. aq., 150 mL). The resulting mixture was extracted with CH$_2$Cl$_2$ (2×100 mL), and the combined organic phases were washed with brine (200 mL), dried over anhydrous Na$_2$SO$_4$ and concentrated under reduced pressure. The residue was purified by flash column chromatography (silica gel, EtOAc:hexanes 1:3→4:1) to give the title compound (18, 4.47 g, 18.0 mmol, 74%) as an orange oil. 18: R$_f$=0.40 (silica gel, EtOAc: hexanes 1:1); [α]$^{25}_D$=−158.8 (c=1.0, CHCl$_3$); FT-IR (neat): ν$_{max}$=3449, 2934, 2865, 2838, 1691, 1612, 1513, 1247, 1173, 1106, 1060, 1033, 832 cm$^{-1}$; $^1$H NMR (CDCl$_3$, 600 MHz) δ=7.27 (d, J=8.4 Hz, 2H), 6.89-6.86 (m, 3H), 6.07 (d, J=10.0 Hz, 1H), 4.64-4.59 (m, 2H), 4.51 (d, J=11.3 Hz, 1H), 4.23-4.21 (m, 1H), 3.79 (s, 3H), 3.53 (s, 1H), 2.64 (dt, J=13.2, 2.4 Hz, 1H), 1.95 (dt, J=13.2, 4.2 Hz, 1H) ppm; $^{13}$C NMR (CDCl$_3$, 150 MHz) δ=200.3, 159.4, 146.6, 129.6, 129.3, 127.7, 113.9, 71.5, 69.7, 68.9, 55.2, 35.0 ppm; HRMS (ESI-TOF) calcd for C$_{14}$H$_{17}$O$_4^+$ [M+H]$^+$ 249.1121, found 249.1114. All spectroscopic data were consistent with those in the literature. (Kato et al., 2006; Myers et al., 2011)

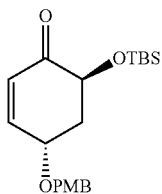

Enone 10:

To a stirred solution of hydroxyenone 18 (4.47 g, 18.0 mmol) in $CH_2Cl_2$ (90 mL) at 25° C. were added imidazole (3.67 g, 54.0 mmol, 3.0 equiv) and TBSCl (4.88 g, 32.4 mmol, 1.8 equiv). After stirring at this temperature for 1.5 h, the reaction was quenched with $NH_4Cl$ (sat. aq., 100 mL). The resulting mixture was extracted with $CH_2Cl_2$ (2×50 mL), and the combined organic phases were washed with brine (200 mL), dried over anhydrous $Na_2SO_4$ and concentrated under reduced pressure. The residue was purified by flash column chromatography (silica gel, EtOAc:hexanes 1:3) to give the title compound (10, 6.45 g, 17.8 mmol, 99%) as a colorless oil. 10: $R_f$=0.54 (silica gel, EtOAc:hexanes 1:4); $[\alpha]^{25}_D$=−119.5 (c=1.0, $CHCl_3$); FT-IR (neat): $v_{max}$=2953, 2929, 2885, 2856, 1696, 1612, 1513, 1249, 1172, 1147, 1077, 1036, 835, 779 $cm^{-1}$; $^1$H NMR ($CDCl_3$, 600 MHz) δ=7.28 (d, J=8.5 Hz, 2H), 6.90 (d, J=8.6 Hz, 2H), 6.87 (dd, J=10.3, 3.6 Hz, 1H), 5.95 (d, J=10.2 Hz, 1H), 4.60 (d, J=11.4 Hz, 1H), 4.55 (d, J=11.4 Hz, 1H), 4.39-4.35 (m, 2H), 3.81 (s, 3H), 2.30-2.20 (m, 2H), 0.88 (s, 9H), 0.10 (s, 3H), 0.09 (s, 3H) ppm; $^{13}$C NMR ($CDCl_3$, 150 MHz) δ=197.4, 159.5, 147.8, 129.8, 129.5, 128.2, 114.0, 71.2, 71.1, 70.3, 55.3, 37.7, 25.7, 18.3, 4.7, −5.4 ppm; HRMS (ESI-TOF) calcd for $C_{20}H_{30}NaO_4Si^+$ [M+Na]$^+$ 385.1806, found 385.1798. All spectroscopic data were consistent with those in the literature. (Kato et al., 2006; Myers et al., 2011)

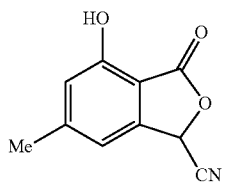

Cyanophthalide 19:

The cyanophthalide 19 was prepared according to the reported procedure. (Nicolaou et al., 2009) 19: $R_f$=0.52 (silica gel, EtOAc:hexanes 1:1); $^1$H NMR ($CDCl_3$, 600 MHz) δ=7.40 (s, 1H), 6.99 (s, 1H), 6.91 (s, 1H), 6.00 (s, 7H), 2.49 (s, 4H) ppm; $^{13}$C NMR ($CDCl_3$, 150 MHz) δ=168.9, 156.5, 150.9, 141.9, 118.6, 115.0, 113.6, 107.0, 66.0, 22.5 ppm. All spectroscopic data were consistent with those reported in the literature. (Nicolaou et al., 2009)

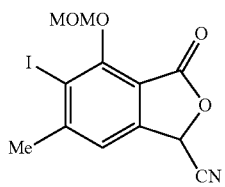

Iodocyanophthalide 9:

To a stirred solution of cyanophthalide 19 (1.04 g, 5.46 mmol) in DCE (100 mL) at −10° C. was added NIS (1.61 g, 7.11 mmol, 1.3 equiv). The reaction flask was covered with aluminum foil to exclude light. After stirring at this temperature for 6 h, the reaction was quenched with $Na_2SO_3$ (10% aq., 100 mL). The resulting mixture was extracted with $CH_2Cl_2$ (2×50 mL), and the combined organic phases were dried over anhydrous $Na_2SO_4$ and concentrated under reduced pressure. The residue was subjected to flash column chromatography (silica gel, EtOAc:hexanes 1:1) to give the unprotected iodocyanophthalide intermediate as a mixture with some starting material 19 (ratio of 10:1).

To a solution of the above mixture in $CH_2Cl_2$ (50 mL) at 25° C. were added chloromethyl methyl ether (376 mg, 4.64 mmol, 0.85 equiv) and N,N-diisopropylethylamine (478 mg, 3.71 mmol, 0.68 equiv). After stirring at this temperature for 6 h, the reaction was quenched with $NaHCO_3$ (5% aq., 100 mL). The resulting mixture was extracted with $CH_2Cl_2$ (2×50 mL), and the combined organic phases were dried over anhydrous $Na_2SO_4$ and concentrated under reduced pressure. The residue was purified by flash column chromatography (silica gel, EtOAc: hexanes 1:6) to give the title compound (9, 984 mg, 2.73 mmol, 50%, two steps) as a yellow solid. 9: $R_f$=0.33 (silica gel, EtOAc:hexanes 1:4); m.p. 117-118° C. (EtOAc: hexanes); FT-IR (neat): $v_{max}$=2930, 1780, 1599, 1452, 1379, 1262, 1206, 1156, 1034, 983, 890, 770 $cm^{-1}$; $^1$H NMR ($CDCl_3$, 600 MHz) δ=7.29 (s, 1H), 5.93 (s, 1H), 5.54 (d, J=6.2 Hz, 1H), 5.50 (d, J=6.2 Hz, 1H), 3.68 (s, 3H), 2.67 (s, 3H) ppm; $^{13}$C NMR ($CDCl_3$, 150 MHz) δ 164.3, 156.4, 153.3, 143.4, 118.1, 113.5, 112.2, 102.5, 101.6, 64.7, 59.0, 30.5 ppm; HRMS (ESI-TOF) calcd for $C_{12}H_9IO_4Si^-$ [M−H]$^-$ 357.9582, found 357.9575.

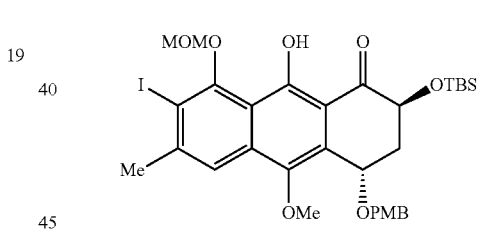

Aryl Iodide 20:

To a stirred solution of iodocyanophthalide 9 (889 mg, 2.46 mmol) in THF (27 mL) at −78° C. was added tBuOLi (1.0 M in THF, 7.40 mL, 0.740 mmol, 3.0 equiv). After stirring at this temperature for 10 min, a solution of enone 10 (889 mg, 2.46 mmol, 1.0 equiv) in THF (27 mL) was added dropwise. The resulting reaction mixture was stirred at −78° C. for 30 min before $Me_2SO_4$ (3.05 g, 24.6 mmol, 10 equiv) was added dropwise. The resulting mixture was warmed to −5° C. and stirred at this temperature for 5 h before it was quenched with $NH_4Cl$ (sat. aq., 150 mL). The resulting mixture was extracted with EtOAc (3×80 mL), and the combined organic phases were washed with brine (150 mL), dried over anhydrous $Na_2SO_4$ and concentrated under reduced pressure. The residue was purified by flash column chromatography (silica gel, EtOAc:hexanes 1:50) to give the title compound 20 (1.24 g, 1.70 mmol, 69%) as an orange oil. 20: $R_f$=0.62 (silica gel, EtOAc:hexanes 1:8); $[\alpha]^{25}_D$=+37.0 (c=1.0, $CHCl_3$); FT-IR (neat): $v_{max}$=2952, 2929, 2855, 1635, 1611, 1514, 1441, 1361, 1250, 1158, 1043, 1003, 924, 872, 837, 780 $cm^{-1}$; $^1$H NMR ($CDCl_3$, 600 MHz) δ=14.87

(s, 1H), 7.73 (s, 1H), 7.28 (d, J=8.6 Hz, 2H), 6.87 (d, J=8.6 Hz, 2H), 5.21 (d, J=5.6 Hz, 1H), 5.18 (t, J=2.6 Hz, 1H), 5.15 (d, J=5.6 Hz, 1H), 4.99 (dd, J=12.4, 5.2 Hz, 1H), 4.68 (d, J=11.1 Hz, 1H), 4.58 (d, J=11.0 Hz, 1H), 3.85 (s, 3H), 3.79 (s, 3H), 3.78 (s, 3H), 2.72 (ddd, J=13.4, 5.1, 3.4 Hz, 1H), 2.67 (s, 3H), 2.18 (ddd, J=13.3, 2.3 Hz, 1H), 1.55 (s, 3H), 0.98 (s, 9H), 0.25 (s, 3H), 0.18 (s, 3H) ppm; $^{13}$C NMR (CDCl$_3$, 150 MHz) δ 204.0, 160.1, 159.3, 156.0, 145.3, 144.8, 134.3, 130.1, 129.5, 126.6, 118.5, 118.4, 113.9, 108.9, 101.7, 100.3, 70.9, 69.4, 68.7, 62.9, 59.1, 55.3, 36.5, 30.3, 25.9, 18.5, −4.4, −5.3 ppm; HRMS (ESI-TOF) calcd for C$_{32}$H$_{41}$INaO$_8$Si$^+$ [M+Na]$^+$ 731.1508, found 731.1485.

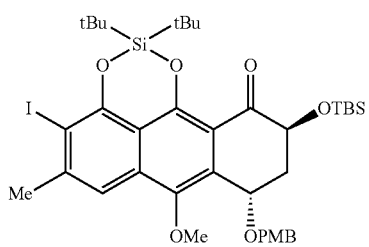

21

Aryl Iodide 21:

To a stirred solution of aryl iodide 20 (1.24 g, 1.70 mmol) in THF (35 mL) at 0° C. was added MgBr$_2$·OEt$_2$ (1.32 g, 5.10 mmol, 3.0 equiv) in one portion. After stirring at this temperature for 10 min, the reaction was quenched with H$_2$O (50 mL). The resulting mixture was extracted with EtOAc (3×50 mL), and the combined organic phases were dried over anhydrous Na$_2$SO$_4$ and concentrated under reduced pressure. The crude residue was taken to the next step without further purification. To a stirred solution of the above crude in DMF (17 mL) at 0° C. was added 2,6-lutidine (546 mg, 5.10 mmol, 3.0 equiv), and then tBu$_2$Si(OTf)$_2$ (896 mg, 2.04 mmol, 1.2 equiv) was added dropwise over a period of 10 min. After stirring at this temperature for another 10 min, the reaction was quenched with NH$_4$Cl (sat. aq., 50 mL) and diluted with EtOAc (100 mL). The resulting mixture was washed with brine (3×100 mL), dried over anhydrous Na$_2$SO$_4$ and concentrated under reduced pressure. The residue was purified by flash column chromatography (silica gel, EtOAc: hexanes 1:50) to give the title compound (21, 1.16 g, 1.45 mmol, 85%, two steps) as an orange oil. 21: R$_f$=0.54 (silica gel, EtOAc:hexanes 1:4); [α]$^{25}_D$=+31.7 (c=1.0, CHCl$_3$); FT-IR (neat): ν$_{max}$=2933, 2896, 2859, 1701, 1600, 1560, 1514, 1471, 1399, 1359, 1249, 1157, 1064, 1007, 828, 780 cm$^{-1}$; $^1$H NMR (CDCl$_3$, 600 MHz) δ=7.50 (s, 1H), 7.31 (d, J=8.6 Hz, 2H), 6.87 (d, J=8.6 Hz, 2H), 5.19 (t, J=2.8 Hz, 1H), 4.87 (dd, J=12.4, 5.0 Hz, 1H), 4.72 (d, J=10.8 Hz, 1H), 4.62 (d, J=10.8 Hz, 1H), 3.89 (s, 3H), 3.79 (s, 3H), 2.73 (ddd, J=13.6, 5.0, 3.1 Hz, 1H), 2.62 (s, 3H), 2.15 (dt, J=13.2, 2.4 Hz, 1H), 1.55 (s, 3H), 1.14 (s, 9H), 1.11 (s, 9H), 0.96 (s, 9H), 0.24 (s, 3H), 0.14 (s, 3H) ppm; $^{13}$C NMR (CDCl$_3$, 150 MHz) δ=194.4, 159.3, 152.3, 148.9, 146.3, 143.1, 131.2, 130.2, 129.8, 129.6, 115.3, 114.7, 114.6, 113.9, 90.7, 71.3, 71.2, 69.9, 62.7, 55.3, 36.4, 29.6, 26.1, 26.0, 26.0, 21.3, 20.9, 18.7, −4.3, −5.4 ppm; HRMS (ESI-TOF) calcd for C$_{38}$H$_{54}$IO$_7$Si$_2^+$ [M+H]$^+$ 805.2447, found 805.2470.

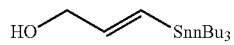

8

Stannane 8:

The stannane 8 was prepared according to the original procedure. (Philli et al., 1998) 8: R$_f$=0.51 (silica gel, EtOAc: hexanes 1:8); $^1$H NMR (CDCl$_3$, 600 MHz) δ 6.29-6.21 (m, 1H), 4.17 (s, 1H), 1.52-1.47 (m, 6H), 1.34-1.27 (m, 6H), 0.94-0.84 (m, 15H) ppm; $^{13}$C NMR (CDCl$_3$, 150 MHz) δ=147.0, 128.3, 66.4, 29.0, 27.3, 13.7, 9.4 ppm. All spectroscopic data were consistent with those reported in the literature. (Pilli et al., 1998)

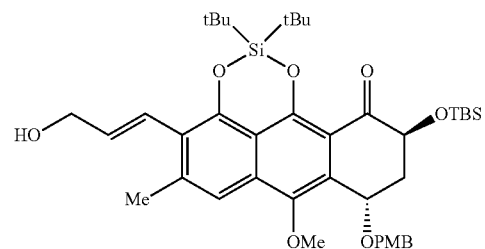

22

Allylic Alcohol 22:

To a stirred mixture of aryl iodide 21 (1.06 g, 1.32 mmol), CuTC (302 mg, 1.58 mmol, 1.2 equiv) and Pd(PPh$_3$)$_4$ (305 mg, 0.264 mmol, 0.2 equiv) in DMF (26 mL) was added stannane 8 (642 mg, 1.85 mmol, 1.4 equiv). After stirring at 110° C. for 12 h, the reaction was cooled to 25° C., then quenched with water (40 mL) and diluted with EtOAc (50 mL). The resulting mixture was washed with brine (3×50 mL), dried over anhydrous Na$_2$SO$_4$ and concentrated under reduced pressure. The residue was purified by flash column chromatography (silica gel, EtOAc:hexanes 1:4) to give the title compound (22, 718 mg, 0.977 mmol, 74%) as a yellow foam. 22: R$_f$=0.23 (silica gel, EtOAc:hexanes 1:4); [α]$^{25}_D$=+26.8 (c=0.85, CH$_2$Cl$_2$); FT-IR (neat): ν$_{max}$=3474, 2896, 2934, 2859, 1697, 1608, 1514, 1445, 1371, 1250, 1158, 1124, 1058, 1034, 1010, 938, 880, 829, 781, 662 cm$^{-1}$; $^1$H NMR (CDCl$_3$, 600 MHz) δ=7.40 (s, 1H), 7.32 (d, J=8.6 Hz, 2H), 6.87 (d, J=8.6 Hz, 2H), 6.71 (d, J=16.1 Hz, 1H), 6.59 (dt, J=16.1, 5.7 Hz, 1H), 5.19 (t, J=2.8 Hz, 1H), 4.88 (dd, J=12.4, 5.0 Hz, 1H), 4.73 (d, J=10.8 Hz, 1H), 4.62 (d, J=10.8 Hz, 1H), 4.39 (dd, J=5.7, 1.3 Hz, 2H), 3.90 (s, 3H), 3.79 (s, 3H), 2.73 (ddd, J=13.5, 5.0, 3.1 Hz, 1H), 2.52 (s, 3H), 2.15 (dt, J=13.4, 2.9 Hz, 1H), 1.13 (s, 9H), 1.10 (s, 9H), 0.96 (s, 9H), 0.25 (s, 3H), 0.14 (s, 3H) ppm; $^{13}$C NMR (CDCl$_3$, 150 MHz) δ=194.5, 159.3, 150.9, 149.9, 146.2, 134.1, 130.5, 130.3, 129.7, 129.0, 124.4, 120.9, 116.1, 115.3, 114.3, 113.9, 71.4, 71.2, 69.9, 64.9, 62.6, 55.3, 36.5, 26.2, 26.1, 26.0, 22.2, 21.3, 20.9, 18.7, −4.3, −5.4 ppm; HRMS (ESI-TOF) calcd for C$_{41}$H$_{59}$O$_8$Si$_2^+$ [M+H]$^+$ 735.3743, found 735.3765.

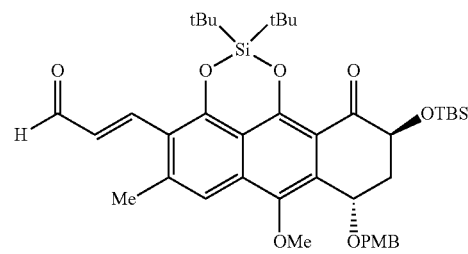

23

Aldehyde 23:

To a stirred solution of allylic alcohol 22 (600 mg, 0.799 mmol) in $CH_2Cl_2$ (8 mL) at 25° C. were added TEMPO (12.5 mg, 0.08 mmol, 0.1 equiv) and $PhI(OAc)_2$ (334 mg, 1.04 mmol, 1.3 equiv). After stirring at this temperature for 4 h, the reaction was quenched with $Na_2SO_3$ (10% aq., 20 mL). The resulting mixture was extracted with $CH_2Cl_2$ (3×10 mL), and the combined organic phases were dried over anhydrous $Na_2SO_4$ and concentrated under reduced pressure. The residue was purified by flash column chromatography (silica gel, EtOAc:hexanes 1:11) to give the title compound (23, 539 mg, 0.720 mmol, 89%) as a yellow foam. 23: $R_f$=0.55 (silica gel, EtOAc:hexanes 1:4); $[α]^{25}_D$=+18.4 (c=1.0, $CH_2Cl_2$); FT-IR (neat): $v_{max}$=2934, 2898, 2859, 1685, 1595, 1514, 1471, 1446, 1372, 1249, 1158, 1125, 1060, 1034, 1010, 939, 879, 828, 781, 663 cm$^{-1}$; $^1$H NMR (CDCl$_3$, 600 MHz) δ=9.72 (d, J=7.7 Hz, 1H), 7.75 (d, J=16.1 Hz, 1H), 7.45 (s, 1H), 7.31 (d, J=8.6 Hz, 2H), 7.06 (dd, J=16.1, 7.7 Hz, 1H), 6.87 (d, J=8.6 Hz, 2H), 5.20 (t, J=2.7 Hz, 1H), 4.88 (dd, J=12.4, 5.0 Hz, 1H), 4.73 (d, J=10.8 Hz, 1H), 4.63 (d, J=10.8 Hz, 1H), 3.90 (s, 3H), 3.79 (s, 3H), 2.74 (ddd, J=13.8, 4.8, 3.0 Hz, 1H), 2.62 (s, 3H), 2.18-2.13 (m, 1H), 1.14 (s, 9H), 1.11 (s, 9H), 0.96 (s, 9H), 0.24 (s, 3H), 0.14 (s, 3H) ppm; $^{13}$C NMR (CDCl$_3$, 150 MHz) δ=195.3, 194.3, 159.4, 154.2, 150.1, 146.6, 146.3, 139.4, 132.8, 132.3, 131.5, 130.0, 129.8, 118.1, 116.1, 116.0, 115.2, 71.3, 71.3, 69.8, 62.7, 55.3, 36.3, 26.2, 26.1, 26.0, 22.3, 21.3, 20.9, 18.7, -4.3, -5.4 ppm; HRMS (ESI-TOF) calcd for $C_{41}H_{57}O_8Si_2^+$ [M+H]$^+$ 733.3585, found 733.3605.

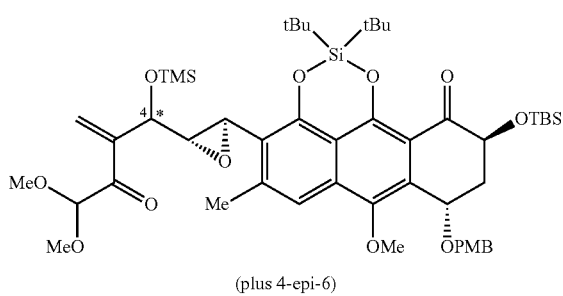

6

(plus 4-epi-6)

Epoxy Ketone 6 (Plus 4-Epi-6):

To a stirred solution of aldehyde 23 (800 mg, 1.07 mmol) in CHCl$_3$ (21 mL) and H$_2$O (1.1 mL) at 25° C. were added urea.H$_2$O$_2$ (706 mg, 7.49 mmol, 7.0 equiv) and (S)-(−)-α,α-diphenyl-2-pyrrolidine methanol trimethylsilyl ether (24, 70.2 mg, 0.218 mmol, 0.2 equiv). After stirring at this temperature for 7 h, the reaction mixture was diluted with EtOAc (100 mL). The resulting mixture was washed with H$_2$O (2×50 mL), dried over anhydrous Na$_2$SO$_4$ and concentrated under reduced pressure to give the crude epoxide 25, which was taken to the next step without further purification.

To a solution of the above crude epoxide 25 in THF (21 mL) at 25° C. was added DABCO (60.0 mg, 0.535 mmol, 0.5 equiv), 4-nitrophenol (74.8 mg, 0.535 mmol, 0.5 equiv) and enone 7 (Edwards et al., 2003) (1.39 g, 10.7 mmol, 10 equiv). After stirring at this temperature for 12 h, the reaction was diluted with EtOAc (100 mL). The resulting mixture was washed with brine (2×50 mL) and concentrated under reduced pressure. The residue was purified by flash column chromatography (silica gel, EtOAc:hexanes 1:4-4:2) to give crude alcohol 26 containing a number of unidentified side products.

The crude alcohol 26 obtained above was dissolved in CH$_2$Cl$_2$ (10 mL), and N-trimethylsilylimidazole (120 mg, 0.856 mmol, 0.8 equiv) was added under stirring at 0° C. The resulting reaction mixture was stirred at this temperature for 30 min, and then concentrated to 2 mL under reduced pressure. The residue was purified by flash column chromatography (silica gel, EtOAc:CH$_2$Cl$_2$:hexanes 1:1:12) to give the title compound 6 (plus C4-epi-6) (355 mg, 0.373 mmol, d.r. ca. 3:1, 36%, three steps) as a yellow foam. 6 (plus C4-epi-6): $R_f$=0.56 (silica gel, EtOAc:hexanes 1:4); $[α]^{25}_D$=+16.8 (c=1.0, CH$_2$Cl$_2$); FT-IR (neat): $v_{max}$=2934, 2898, 2859, 1696, 1614, 1560, 1514, 1471, 1445, 1371, 1250, 1158, 1055, 1010, 938, 879, 829, 780, 662 cm$^{-1}$; $^1$H NMR (CDCl$_3$, 600 MHz) δ=7.36 (s, 1H, major), 7.32-7.30 (m, 5H, major+minor), 6.87-6.84 (m, 4H, major+minor), 6.66 (s, 1H, major), 6.63 (s, 1H, minor), 6.48 (s, 1H, major), 6.45 (s, 1H, minor), 5.17-5.16 (m, 2H, major+minor), 5.11 (d, J=2.0 Hz, 1H, major), 5.08 (d, J=2.4 Hz, 1H, minor), 5.06 (s, 1H, major), 5.01 (s, 1H, minor), 4.86 (dd, J=12.4, 5.0 Hz, 2H, major+minor), 4.71 (d, J=10.9 Hz, 2H, major+minor), 4.61 (d, J=10.8 Hz, 2H, major+minor), 4.11 (d, J=2.2 Hz, 1H, major), 3.89 (d, J=2.2 Hz, 1H, minor), 3.86 (s, 6H, major+minor), 3.79 (s, 6H, major+minor), 3.54 (t, J=2.5 Hz, 1H, minor), 3.50 (t, J=2.4 Hz, 1H, major), 3.42 (s, 6H, minor), 3.40 (s, 3H, major), 3.39 (s, 3H, major), 2.71 (ddd, J=13.5, 4.9, 3.1 Hz, 2H, major+minor), 2.58 (s, 3H, major), 2.48 (s, 3H, minor), 2.17-2.12 (m, 2H, major+minor), 1.18 (s, 9H, major), 1.15 (s, 9H, minor), 1.10 (s, 9H, minor), 1.10 (s, 9H, major), 0.95 (s, 18H, major+minor), 0.24 (s, 6H, major+minor), 0.15 (s, 9H, major), 0.14 (s, 9H, minor), 0.14 (s, 6H, major+minor) ppm; $^{13}$C NMR (CDCl$_3$, 150 MHz) δ=194.4 (major+minor), 193.8 (minor), 193.8 (major), 159.3 (major+minor), 152.1 (minor), 151.4 (major), 149.8 (major+minor), 146.1 (major), 146.1 (minor), 144.2 (major), 144.0 (minor), 141.4 (major), 140.5 (minor), 131.4 (major), 131.3 (minor), 130.4 (minor), 130.3 (major), 130.3 (minor), 130.1 (major), 129.7 (major+minor), 129.3 (major), 129.3 (minor), 119.7 (major), 119.6 (minor), 115.7 (minor), 115.7 (major), 115.4 (major), 115.4 (minor), 114.3 (major), 114.2 (minor), 113.8 (major+minor), 102.7 (minor), 102.1 (major), 71.3 (major+minor), 71.2 (major+minor), 69.9 (minor), 69.8 (major), 67.8 (minor), 67.1 (major), 62.6 (major+minor), 61.6 (major), 61.0 (minor), 55.3 (major+minor), 54.6 (minor), 54.4 (minor), 54.3 (major), 54.1 (major), 52.4 (major), 51.5 (minor), 36.5 (major), 36.5 (minor), 26.4 (major+minor), 26.2 (minor), 26.2 (major), 26.0 (major+minor), 21.2 (major), 21.2 (minor), 21.1 (minor), 21.1 (major), 21.0 (major), 20.9 (minor), 18.7 (major+minor), 0.1 (major), 0.0 (minor), -4.3 (major+minor), -5.4 (major+minor) ppm; HRMS (ESI-TOF) calcd for $C_{50}H_{75}O_{12}Si_3^+$ [M+H]$^+$ 951.4561, found 951.4581.

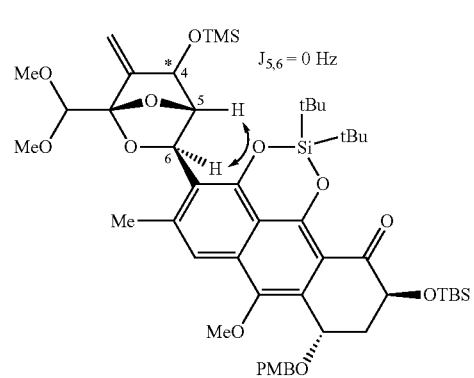

27

Acetal 27 (Stereochemistry Assigned by Coupling Constant Studies[111]):

To a stirred solution of epoxy ketone 6 (plus C4-epi-6) (20.1 mg, 0.021 mmol) in $CH_2Cl_2$ (0.8 mL) at −78° C. was added $SnCl_4$ (0.01 M in $CH_2Cl_2$, 21 μL, 0.021 mmol, 0.1 equiv) dropwise. After stirring at this temperature for 2 h, the reaction was quenched with $NaHCO_3$ (sat. aq., 2 mL). The resulting mixture was extracted with $CH_2Cl_2$ (3×2 mL), and the combined organic phases were dried over anhydrous $Na_2SO_4$ and concentrated under reduced pressure. The residue was purified by flash column chromatography (silica gel, EtOAc:hexanes 1:13) to give the title compound (27, plus C4-epi-27) (7.3 mg, 0.0076 mmol, d.r. ca. 13:1, 37%) as yellow oil. $R_f$=0.58 (silica gel, EtOAc:hexanes 1:4); 27 (+C4-epi-27): $R_f$=0.63 (silica gel, EtOAc:hexanes 1:4); $[\alpha]^{25}_D$=+30.4 (c=0.45, $CH_2Cl_2$); FT-IR (neat): $\nu_{max}$=2952, 2934, 2898, 2859, 1697, 1613, 1562, 1514, 1471, 1445, 1370, 1252, 1159, 1088, 1059, 1011, 954, 890, 830, 661 $cm^{-1}$; $^1$H NMR ($CDCl_3$, 600 MHz, major isomer) δ=7.40 (s, 1H), 7.30 (d, J=8.6 Hz, 2H), 6.86 (d, J=8.6 Hz, 2H), 5.69 (s, 1H), 5.60 (d, J=2.2 Hz, 1H), 5.18 (t, J=2.6 Hz, 1H), 5.17-5.15 (m, 2H), 4.86 (dd, J=12.3, 5.1 Hz, 1H), 4.71-4.68 (m, 2H), 4.64 (s, 1H), 4.60 (d, J=10.8 Hz, 1H), 3.88 (s, 3H), 3.79 (s, 3H), 3.53 (s, 3H), 3.50 (s, 3H), 2.75-2.70 (m, 1H), 2.65 (s, 3H), 2.17-2.12 (m, 1H), 1.17 (s, 9H), 1.11 (s, 9H), 0.95 (s, 9H), 0.24 (s, 3H), 0.16 (s, 9H), 0.14 (s, 3H) ppm; $^{13}$C NMR ($CDCl_3$, 150 MHz, major isomer) δ=194.5, 159.3, 151.7, 150.2, 147.3, 146.0, 142.1, 131.6, 130.3, 129.7, 129.5, 120.3, 116.3, 116.0, 114.3, 113.8, 108.6, 107.6, 104.5, 79.7, 72.9, 71.3, 71.1, 71.1, 69.8, 62.6, 57.1, 56.9, 55.3, 36.6, 26.3, 26.2, 26.0, 22.3, 21.5, 20.9, 18.7, 0.1, −4.3, −5.4 ppm; HRMS (ESI-TOF) calcd for $C_{50}H_{75}O_{12}Si_3^+$ $[M+H]^+$ 951.4561, found 951.4576.

Acetal 5a and 5b:

To a stirred solution of epoxy ketone 6 (plus 4-epi-6) (140 mg, 0.147 mmol) in $CH_2Cl_2$ (4.4 mL) at −78° C. was added $BF_3·OEt_2$ (0.1 M in $CH_2Cl_2$, 440 μL, 0.044 mmol, 0.3 equiv) drop wise. After stirring at this temperature for 6 h, the reaction was quenched sequentially with $Et_3N$ (40 μL) and $NaHCO_3$ (sat. aq., 10 mL). The resulting mixture was extracted with $CH_2Cl_2$ (3×10 mL), and the combined organic phases were dried over anhydrous $Na_2SO_4$ and concentrated under reduced pressure. The residue was purified by flash column chromatography (silica gel, EtOAc:hexanes 1:20) to give the title compound (5a, 75.0 mg, 0.079 mmol, 54%; 5b, 25.0 mg, 0.026 mmol, 18%) as a yellow foam. 5a (stereochemistry assigned by coupling constant studies [Padwa et al., 1991; Kraehenbuehl et al., 1995; Kraehenbuehl et al., 1998; Muthusamy et al., 2002]): $R_f$=0.68 (silica gel, EtOAc:hexanes 1:4); $[\alpha]^{25}_D$=+168.8 (c=1.0, $CH_2Cl_2$); FT-IR (neat): $\nu_{max}$=2934, 2897, 2859, 1697, 1609, 1559, 1514, 1471, 1445, 1398, 1369, 1250, 1161, 1110, 1052, 1032, 999, 892, 878, 827, 731, 661 $cm^{-1}$; $^1$H NMR ($CDCl_3$, 600 MHz) δ=7.31 (s, 1H), 7.29 (d, J=9.1 Hz, 2H), 6.87 (d, J=8.6 Hz, 2H), 5.70 (d, J=3.1 Hz, 1H), 5.47 (d, J=2.3 Hz, 1H), 5.23 (t, J=2.7 Hz, 1H), 5.06 (d, J=2.0 Hz, 1H), 4.96 (dd, J=4.2, 3.0 Hz, 1H), 4.87-4.84 (m, 2H), 4.71-4.69 (m, 2H), 4.60 (d, J=10.7 Hz, 1H), 3.89 (s, 3H), 3.79 (s, 3H), 3.62 (s, 3H), 3.61 (s, 3H), 2.73 (ddd, J=13.5, 4.9, 3.1 Hz, 1H), 2.66 (s, 3H), 2.14 (dt, J=13.4, 2.7 Hz, 1H), 1.14 (s, 9H), 1.06 (s, 9H), 0.96 (s, 9H), 0.24 (s, 3H), 0.14 (s, 3H), −0.33 (s, 9H) ppm; $^{13}$C NMR ($CDCl_3$, 150 MHz) δ=194.4, 159.3, 149.3, 148.8, 146.7, 146.2, 141.6, 130.2, 130.1, 129.8, 120.8, 116.8, 115.0, 113.9, 108.8, 106.6, 102.2, 79.9, 79.8, 73.2, 71.4, 71.1, 70.1, 62.7, 56.2, 55.7, 55.3, 36.4, 26.5, 26.3, 26.0, 24.1, 21.7, 20.5, 18.7, −0.4, −4.3, −5.4 ppm; HRMS (ESI-TOF) calcd for $C_{50}H_{74}NaO_{12}Si_3^+$ $[M+Na]^+$ 973.4370, found 973.4380. 5b (stereochemistry assigned by coupling constant studies [Padwa et al., 1991; Kraehenbuehl et al., 1995; Kraehenbuehl et al., 1998; Muthusamy et al., 2002]): $R_f$=0.65 (silica gel, EtOAc:hexanes 1:4); $[\alpha]^{25}_D$=+165.8 (c=1.0, $CH_2Cl_2$); FT-IR (neat): $\nu_{max}$=2935, 2860, 1698, 1610, 1560, 1514, 1471, 1445, 1399, 1371, 1250, 1162, 1059, 1033, 1012, 938, 885, 840, 828, 781, 662 $cm^{-1}$; $^1$H NMR ($CDCl_3$, 600 MHz) δ=7.34 (s, 1H), 7.32 (d, J=8.5 Hz, 2H), 6.88 (d, J=8.5 Hz, 2H), 5.60 (s, 1H), 5.46 (d, J=3.6 Hz, 1H), 5.20 (t, J=2.6 Hz, 1H), 5.16 (s, 1H), 5.04 (d, J=3.7 Hz, 1H), 4.96 (s, 1H), 4.87 (dd, J=12.6, 4.8 Hz, 1H), 4.74 (d, J=10.7 Hz, 1H), 4.64 (d, J=10.7 Hz, 1H), 4.17 (s, 1H), 3.90 (s, 3H), 3.79 (s, 3H), 3.62 (s, 3H), 3.61 (s, 3H), 2.73 (ddd, J=13.5, 4.7, 3.2 Hz, 1H), 2.59 (s, 3H), 2.15 (dt, J=13.4, 2.6 Hz, 1H), 1.14 (s, 9H), 1.06 (s, 9H), 0.96 (s, 9H), 0.24 (s, 3H), 0.14 (s, 3H), −0.06 (s, 9H) ppm; $^{13}$C NMR ($CDCl_3$, 150 MHz) δ=194.5, 159.4, 150.2, 149.8, 149.2, 146.2, 139.9, 130.5, 130.1, 129.9, 129.0, 119.2, 117.6, 115.3, 114.4, 113.9, 109.5, 107.0, 101.4, 85.4, 77.4, 71.3, 71.2, 70.0, 62.7, 56.2, 55.3, 55.0, 36.3, 26.4, 26.3, 26.0, 23.9, 21.7, 20.6, 18.7, 0.5, −4.3, −5.4 ppm; HRMS (ESI-TOF) calcd for $C_{50}H_{75}O_{12}Si_2^+$ $[M+H]^+$ 951.4561, found 951.4586.

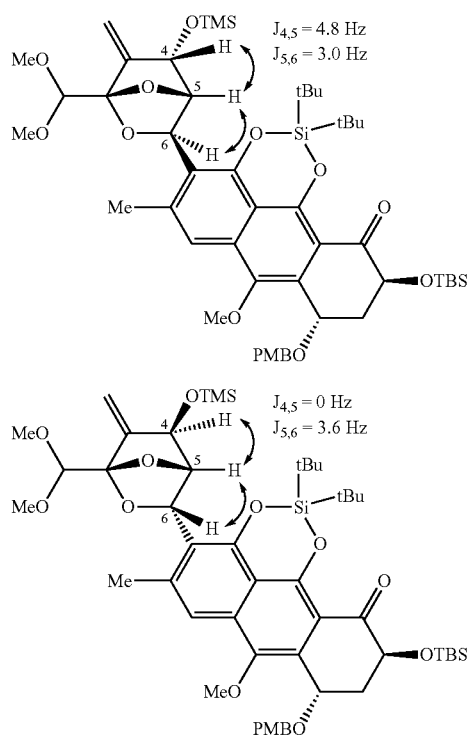

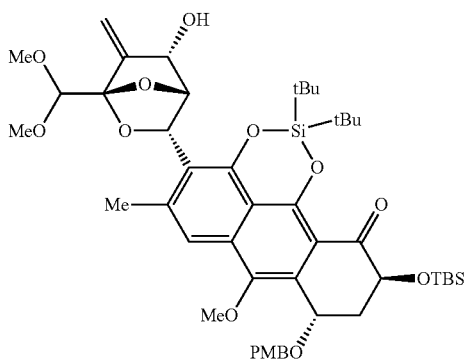

28

Allylic Alcohol 28:

Acetal 5a (52.2 mg, 0.548 mmol) was dissolved in a solution of TFA (0.1 M in THF:H$_2$O 5:1, 5.5 mL). After stirring at 25° C. for 5 h, the reaction was quenched with NaHCO$_3$ (sat. aq., 10 mL). The resulting mixture was extracted with CH$_2$Cl$_2$ (3×5 mL), and the combined organic phases were dried over anhydrous Na$_2$SO$_4$ and concentrated under reduced pressure. The residue was purified by flash column chromatography (silica gel, EtOAc:hexanes 1:10-4:4) to give the title compound (28, 31.0 mg, 0.035 mmol, 65%) as a yellow foam and recovered starting material (5a, 12.5 mg, 0.013 mmol, 24%). 28: R$_f$=0.61 (silica gel, EtOAc:hexanes 1:2); $[\alpha]^{25}_u$=+134.5 (c=1.0, CH$_2$Cl$_2$); FT-IR (neat): $\nu_{max}$=3497, 2934, 2898, 2859, 1697, 1610, 1559, 1514, 1471, 1445, 1398, 1372, 1249, 1162, 1087, 1053, 1033, 937, 827, 781, 661 cm$^{-1}$; $^1$H NMR (CDCl$_3$, 600 MHz) δ=7.37 (s, 1H), 7.30 (d, J=8.6 Hz, 2H), 6.86 (d, J=8.6 Hz, 3H), 5.66 (d, J=3.0 Hz, 1H), 5.53 (d, J=2.4 Hz, 1H), 5.30 (d, J=2.4 Hz, 1H), 5.21-5.19 (m, 2H), 4.88 (dd, J=12.4, 5.0 Hz, 2H), 4.84 (s, 1H), 4.72 (d, J=10.9 Hz, 1H), 4.65-4.64 (m, 2H), 4.61 (d, J=10.9 Hz, 1H), 3.89 (s, 3H), 3.78 (s, 3H), 3.62 (s, 3H), 3.61 (s, 3H), 2.74-2.68 (m, 1H), 2.68 (s, 3H), 2.14 (dt, J=13.6, 2.6 Hz, 1H), 1.15 (s, 9H), 1.09 (s, 9H), 0.95 (s, 9H), 0.23 (s, 3H), 0.13 (s, 3H) ppm; $^{13}$C NMR (CDCl$_3$, 150 MHz) δ=194.5, 159.3, 150.1, 149.1, 147.3, 146.1, 138.6, 130.8, 130.2, 129.7, 129.3, 119.3, 118.3, 115.3, 114.5, 113.8, 108.7, 107.5, 102.2, 79.5, 79.2, 75.2, 71.3, 71.2, 69.8, 62.7, 56.3, 55.8, 55.3, 36.4, 26.2, 26.0, 24.7, 21.5, 20.9, 18.7, −4.3, −5.4 ppm; HRMS (ESI-TOF) calcd for C$_{47}$H$_{67}$O$_{12}$Si$_2$$^+$ [M+H]$^+$ 879.4166, found 879.4177.

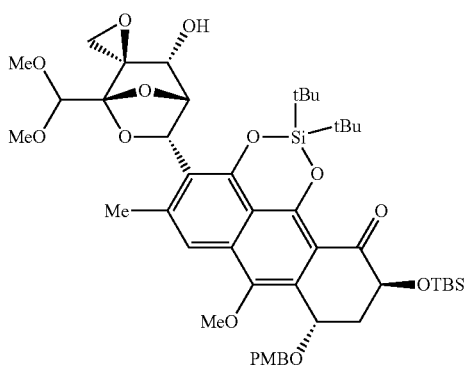

29

Epoxy Alcohol 29:

To a stirred solution of the allylic alcohol 28 (30.1 mg, 0.034 mmol) in acetone (1.0 mL) at 25° C. were sequentially added OsO$_4$ (0.08 M aq., 85 μL, 0.068 mmol, 0.2 equiv) and NMO (0.48 M aq., 283 μL, 0.136 mmol, 4.0 equiv). After stirring at this temperature for 12 h, the reaction was quenched with Na$_2$SO$_3$ (10% aq., 10 mL). The resulting mixture was stirred for another 30 min, then extracted with CH$_2$Cl$_2$ (3×5 mL), and the combined organic phases were dried over anhydrous Na$_2$SO$_4$ and concentrated under reduced pressure. The residue was purified by flash column chromatography (silica gel, EtOAc:hexanes 1:2) to give the triol intermediate (26.3 mg, 0.029 mmol) as a yellow foam. To a stirred solution of the above triol intermediate (26.3 mg, 0.029 mmol) in CH$_2$Cl$_2$ (1.0 mL) at 25° C. were added Et$_3$N (14.6 mg, 0.144 mmol, 5.0 equiv), DMAP (2.0 mg, 0.0144 mmol, 0.5 equiv) and TsCl (16.4 mg, 0.144 mmol, 5.0 equiv), sequentially. After stirring at this temperature for 5 h, the reaction was quenched with NH$_4$Cl (sat. aq., 5 mL). The resulting mixture was extracted with CH$_2$Cl$_2$ (3×5 mL), and the combined organic phases were dried over anhydrous Na$_2$SO$_4$ and concentrated under reduced pressure. The residue was purified by flash column chromatography (silica gel, EtOAc:hexanes 1:2) to give the corresponding primary tosylate intermediate (31.0 mg, 0.029 mmol) as a yellow foam.

To a stirred solution of the above tosylate intermediate (31.0 mg, 0.029 mmol) in MeOH (1.0 mL) at 25° C. was added K$_2$CO$_3$ (8.0 mg, 0.058 mmol, 2.0 equiv). The resulting reaction mixture was stirred at this temperature for 1 h and was then directly subjected to flash column chromatography (silica gel, EtOAc:hexanes 4:1) to give the title compound (29, 25.0 mg, 0.028 mmol, 82%, three steps) as a yellow foam. 29: R$_f$=0.52 (silica gel, EtOAc:hexanes 1:2); $[\alpha]^{25}_D$=+106.5 (c=1.0, CH$_2$Cl$_2$); FT-IR (neat): $\nu_{max}$=3487, 2934, 2859, 1696, 1610, 1560, 1514, 1471, 1445, 1399, 1371, 1249, 1162, 1079, 1055, 1003, 978, 828, 662 cm$^{-1}$; $^1$H NMR (CDCl$_3$, 600 MHz) δ=7.39 (s, 1H), 7.29 (d, J=8.6 Hz, 2H), 6.85 (d, J=8.6 Hz, 2H), 5.66 (d, J=2.8 Hz, 1H), 5.40 (dd, J=4.8, 3.3 Hz, 1H), 5.19 (t, J=2.5 Hz, 1H), 4.86 (dd, J=12.3, 5.1 Hz, 1H), 4.73 (s, 1H), 4.71 (d, J=10.9 Hz, 1H), 4.60 (d, J=10.9 Hz, 1H), 4.31 (dd, J=9.1, 5.1 Hz, 1H), 3.89 (s, 3H), 3.78 (s, 3H), 3.63 (s, 3H), 3.55 (s, 3H), 3.29 (d, J=5.5 Hz, 1H), 3.07 (d, J=5.4 Hz, 1H), 2.73-2.71 (m, 4H), 2.14 (dt, J=13.6, 2.5 Hz, 1H), 1.15 (s, 9H), 1.09 (s, 9H), 0.95 (s, 9H), 0.23 (s, 3H), 0.13 (s, 3H) ppm; $^{13}$C NMR (CDCl$_3$, 150 MHz) δ=194.5, 159.2, 150.0, 149.1, 146.1, 138.9, 130.7, 130.2, 129.6, 129.4, 118.7, 118.1, 115.3, 114.6, 113.8, 108.0, 100.1, 79.3, 78.0, 76.2, 71.3, 71.1, 69.7, 67.9, 62.7, 56.7, 56.1, 55.3, 47.6, 36.5, 26.3, 26.3, 26.0, 24.0, 21.5, 20.8, 18.7, −4.3, −5.4 ppm; HRMS (ESI-TOF) calcd for C$_{47}$H$_{67}$O$_{13}$Si$_2$$^+$ [M+H]$^+$ 895.4136, found 895.4115.

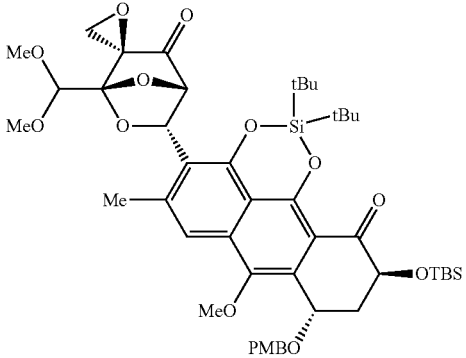

30

Keto Epoxide 30:

To a stirred solution of the epoxy alcohol 29 (30.0 mg, 0.034 mmol) in CH$_2$Cl$_2$ at 25° C. were added NMO.H$_2$O (13.6 mg, 0.101 mmol, 3.0 equiv) and TPAP (2.4 mg, 0.007 mmol, 0.2 equiv). The resulting reaction mixture was stirred at this temperature for 1 h, and then directly subjected to flash column chromatography (silica gel, EtOAc:hexanes 1:4) to give the title compound (30, 27.8 mg, 0.031 mmol, 93%) as a yellow foam. 30: R$_f$=0.51 (silica gel, EtOAc:hexanes 1:4); $[\alpha]^{25}_D$=+192.9 (c=1.0, CH$_2$Cl$_2$); FT-IR (neat): $\nu_{max}$=2934, 2859, 1788, 1702, 1611, 1514, 1471, 1445, 1373, 1250, 1162, 1082, 1045, 1010, 827, 662 cm$^{-1}$; $^1$H NMR (CDCl$_3$, 600 MHz) δ=7.33 (s, 1H), 7.29 (d, J=8.5 Hz, 2H), 6.86 (d, J=8.5 Hz, 2H), 5.62 (d, J=3.8 Hz, 1H), 5.45 (d, J=3.8 Hz, 1H), 5.19 (br s, 1H), 4.88-4.85 (m, 2H), 4.70 (d, J=10.9 Hz, 1H), 4.60 (d, J=10.9 Hz, 1H), 3.87 (s, 3H), 3.79 (s, 3H), 3.69 (s, 3H), 3.58 (s, 3H), 3.39 (d, J=6.4 Hz, 1H), 3.10 (d, J=6.4 Hz, 1H), 2.74-2.70 (m, 1H), 2.59 (s, 3H), 2.15-2.11 (m, 1H), 1.17 (s, 9H), 1.09 (s, 9H), 0.95 (s, 9H), 0.23 (s, 3H), 0.13 (s, 3H) ppm; $^{13}$C NMR (CDCl$_3$, 150 MHz) δ=202.1, 194.5, 159.2, 150.3, 149.1, 146.1, 138.8, 131.0, 130.2, 129.7, 129.6, 118.0, 117.1, 115.3, 114.6, 113.8, 107.5, 99.9, 82.0, 78.0, 71.3, 71.1, 69.7, 62.7, 61.8, 57.1, 56.2, 55.3, 50.1, 36.4, 26.3, 26.2, 26.0, 23.8, 21.5, 20.8, 18.7, −4.3, −5.4 ppm; HRMS (ESI-TOF) calcd for C$_{47}$H$_{65}$O$_{13}$Si$_2^+$ [M+H]$^+$ 893.3958, found 893.3934. All spectroscopic data were consistent with those reported in the literature. (Švenda et al., 2011)

31

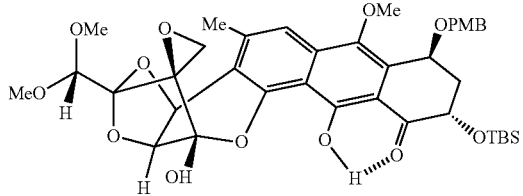

Hemiacetal 31:

To a stirred solution of keto epoxide 30 (20.1 mg, 0.0225 mmol) in CH$_3$CN (1.0 mL) at 25° C. was added Et$_3$N.3HF (10.0 mg, 0.061 mmol, 3.0 equiv). After stirring at this temperature for 15 min, the reaction was quenched with NaHCO$_3$ (5% aq., 5 mL) and diluted with EtOAc (10 mL). The resulting mixture was washed sequentially with H$_2$O (5 mL) and brine (5 mL), dried over anhydrous Na$_2$SO$_4$ and concentrated under reduced pressure. The residue was purified by flash column chromatography (silica gel, EtOAc:hexanes 2:1) to give the title compound (31, 15.0 mg, 0.0199 mmol, 88%) as an orange foam. 31: R$_f$=0.42 (silica gel, EtOAc:hexanes 2:1); $[\alpha]^{25}_D$=+200.3 (c=1.0, CH$_2$Cl$_2$); FT-IR (neat): $\nu_{max}$=3412, 2952, 2930, 2855, 1620, 1570, 1514, 1390, 1124, 1067, 1033, 983, 945, 870, 836, 778 cm$^{-1}$; $^1$H NMR (CDCl$_3$, 600 MHz) δ=14.78 (s, 1H), 7.41 (s, 1H), 7.27 (d, J=8.6 Hz, 2H), 6.86 (d, J=8.6 Hz, 2H), 5.25 (d, J=4.0 Hz, 1H), 5.16 (t, J=2.5 Hz, 1H), 4.94 (dd, J=12.4, 5.1 Hz, 1H), 4.88 (d, J=4.0 Hz, 1H), 4.69 (s, 1H), 4.69 (d, J=11.0 Hz, 1H), 4.58 (d, J=11.0 Hz, 1H), 4.48 (br s, 1H), 3.81 (s, 3H), 3.79 (s, 3H), 3.61 (s, 3H), 3.46 (s, 3H), 3.09 (d, J=5.3 Hz, 1H), 2.95 (d, J=5.3 Hz, 1H), 2.71 (ddd, J=13.4, 5.0, 3.4 Hz, 1H), 2.57 (s, 3H), 2.18 (td, J=13.4, 2.3 Hz, 1H), 0.96 (s, 9H), 0.23 (s, 3H), 0.16 (s, 3H) ppm; $^{13}$C NMR (CDCl$_3$, 150 MHz) δ=203.3, 162.6, 159.3, 151.4, 144.1, 141.8, 135.1, 130.1, 129.5, 127.6, 116.4, 114.9, 114.6, 113.9, 108.6, 103.8, 100.1, 98.5, 73.2, 70.9, 69.7, 69.3, 69.2, 68.9, 62.7, 57.0, 56.7, 55.3, 50.4, 36.2, 25.9, 20.4, 18.6, −4.4, −5.3 ppm; HRMS (ESI-TOF) calcd for C$_{39}$H$_{49}$O$_{13}$Si$^+$ [M+H]$^+$ 753.2937, found 753.2952. All spectroscopic data were consistent with those reported in the literature. (Švenda et al., 2011)

32

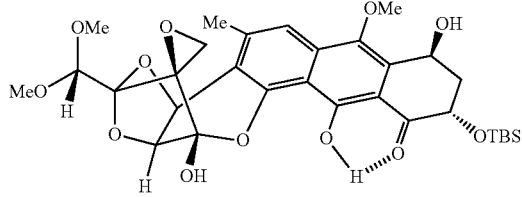

Hydroxy Hemiacetal 32:

To a stirred solution of hemiacetal 31 (15.2 mg, 0.0202 mmol) in CH$_2$Cl$_2$ (1.0 mL) and H$_2$O (0.1 mL) at 25° C. in a reaction flask shielded from light using aluminum foil was added DDQ (6.9 mg, 0.0303 mmol, 1.5 equiv). After stirring at this temperature for 3 h, the reaction was quenched with brine (5 mL). The resulting mixture was extracted with CH$_2$Cl$_2$ (3×5 mL), dried over anhydrous Na$_2$SO$_4$, and concentrated under reduced pressure. The residue was purified by flash column chromatography (silica gel, EtOAc:hexanes 3:1) to give the title compound (31, 11.9 mg, 0.0187 mmol, 93%) as an orange foam. 32: R$_f$=0.70 (silica gel, EtOAc); $[\alpha]^{25}_D$=+131.5 (c=0.2, CH$_2$Cl$_2$); FT-IR (neat): $\nu_{max}$=2930, 2854, 1620, 1570, 1514, 1444, 1390, 1250, 1157, 1124, 1067, 983, 871, 837, 779 cm$^{-1}$; $^1$H NMR (CDCl$_3$, 600 MHz) δ=14.63 (s, 1H), 7.43 (s, 1H), 5.42 (t, J=3.0 Hz, 1H), 5.25 (d, J=4.0 Hz, 1H), 4.88 (dd, J=11.7, 4.9 Hz, 1H), 4.83 (d, J=4.0 Hz, 1H), 4.70 (s, 1H), 4.42 (br s, 1H), 3.91 (s, 3H), 3.62 (s, 3H), 3.47 (s, 3H), 3.13 (d, J=5.3 Hz, 1H), 3.03 (d, J=5.3 Hz, 1H), 2.60 (s, 3H), 2.53 (br s, 1H), 2.49 (dt, J=13.5, 4.5 Hz, 1H), 2.34 (dt, J=13.6, 3.4 Hz, 1H), 0.94 (s, 9H), 0.21 (s, 3H), 0.16 (s, 3H) ppm; $^{13}$C NMR (CDCl$_3$, 150 MHz) δ=202.8, 162.4, 151.5, 143.8, 142.0, 135.2, 129.6, 116.1, 114.8, 114.6, 107.9, 103.9, 100.1, 98.5, 73.2, 69.6, 69.4, 69.3, 62.6, 57.0, 56.6, 50.5, 38.6, 25.8, 20.4, 18.5, 4.5, −5.3 ppm; HRMS (ESI-TOF) calcd for C$_{31}$H$_{41}$O$_{12}$Si$^+$ [M+H]$^+$ 633.2362, found 633.2344.

1

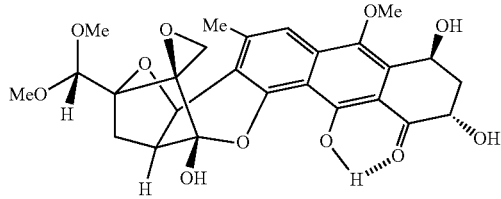

DC-45-A2

DC-45-A2 (1):

To a stirred solution of ketone 31 (10.2 mg, 0.0161 mmol) in CH$_3$CN (1.0 mL) at 25° C. in a reaction flask shielded from light using aluminum foil was added Et$_3$N.3HF (49.0 mg, 0.30 mmol, 20 equiv). After stirring at this temperature for 12 h, the reaction was quenched with NaHCO$_3$ (5% aq., 5 mL) and diluted with EtOAc (10 mL). The resulting mixture was washed sequentially with water (5 mL) and brine (5 mL), dried over anhydrous Na$_2$SO$_4$, and concentrated under reduced pressure. The residue was purified by preparatory HPLC (Atlantis Prep T3 OBD column, 5 μm, 19×150 mm, UV detection at 271 nm, isocratic elution with 20% MeCN in H$_2$O, flow rate: 10 mL/min, 32→34 min) to give DC-45-A2 (1, 7.2 mg, 0.0138 mmol, 86%) as an orange solid. 1: R$_f$=0.21-0.62 (tailing, silica gel, EtOAc); [α]$^{25}$$_D$=+182 (c=0.3, CH$_2$Cl$_2$); FT-IR (neat): ν$_{max}$=3364, 2961, 2926, 2853, 1621, 1571, 1446, 1387, 1099, 1067, 1014, 940, 801 cm$^{-1}$; $^1$H NMR (CDCl$_3$, 600 MHz) δ=14.00 (s, 1H), 7.46 (s, 1H), 5.45 (s, 1H), 5.26 (d, J=3.9 Hz, 1H), 4.92 (dd, J=12.6, 5.2 Hz, 1H), 4.84 (d, J=3.8 Hz, 1H), 4.71 (s, 1H), 3.92 (s, 3H), 3.62 (s, 3H), 3.47 (s, 3H), 3.15 (d, J=5.4 Hz, 1H), 3.03 (d, J=5.3 Hz, 1H), 2.74-2.70 (m, 1H), 2.62 (s, 3H), 2.21-2.16 (m, 1H) ppm; $^{13}$C NMR (CDCl$_3$, 150 MHz) δ=203.2, 162.3, 151.7, 144.4, 142.7, 135.7, 129.4, 116.4, 115.0, 114.7, 107.1, 103.9, 100.1, 98.6, 73.2, 69.6, 69.3, 67.7, 62.8, 61.9, 57.0, 56.7, 50.5, 36.9, 20.5 ppm; HRMS (ESI-TOF) calcd for C$_{25}$H$_{27}$O$_{12}$$^+$ [M+H]$^+$ 519.1497, found 519.1482. All spectroscopic data were consistent with those reported in the literature. (Švenda et al., 2011)

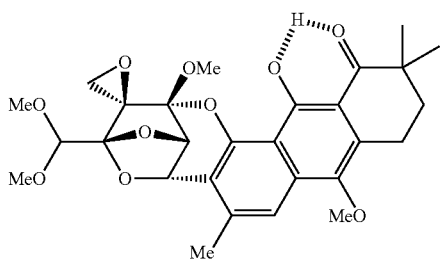

KCN-Trox5:

[α]$^{25}$$_D$=+190.9 (c=0.23, CH$_2$Cl$_2$); FT-IR (neat): ν$_{max}$=2926, 2852, 1622, 1570, 1446, 1390, 1225, 1193, 1113, 1078, 1043, 1006, 974, 801 cm$^{-1}$; $^1$H NMR (CDCl$_3$, 600 MHz) δ=15.04 (s, 1H), 7.42 (s, 1H), 5.22 (d, J=4.1 Hz, 1H), 4.81 (d, J=4.1 Hz, 1H), 4.75 (s, 1H), 3.79 (s, 3H), 3.74 (s, 3H), 3.63 (s, 3H), 3.45 (s, 3H), 3.05 (dd, J=5.0, 7.2 Hz, 2H), 2.90 (d, J=5.7 Hz, 1H), 2.88 (d, J=5.7 Hz, 1H), 2.59 (s, 3H), 1.95 (dd, J=6.4, 6.4 Hz, 2H), 1.30 (s, 3H), 1.29 (s, 3H) ppm; $^{13}$C NMR (CDCl$_3$, 150 MHz) δ=209.5, 163.5, 151.4, 142.2, 141.6, 135.1, 129.9, 115.5, 113.4, 113.1, 109.5, 104.5, 102.0, 99.9, 71.4, 69.2, 60.8, 57.1, 56.7, 52.8, 41.6, 35.6, 25.1, 25.0, 20.4, 19.6 ppm.

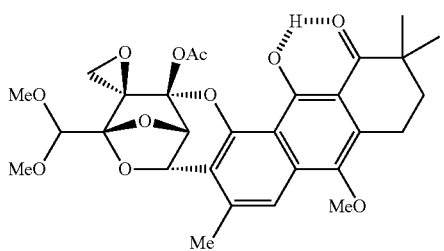

KCN-Trox6:

[α]$^{25}$$_D$=+201.7 (c=0.18, CH$_2$Cl$_2$); FT-IR (neat): ν$_{max}$=2926, 1767, 1622, 1569, 1446, 1391, 1211, 1089, 1044, 990, 868, 803 cm$^{-1}$; $^1$H NMR (CDCl$_3$, 600 MHz) δ=14.88 (s, 1H), 7.43 (s, 1H), 5.60 (d, J=4.1 Hz, 1H), 5.26 (d, J=4.2 Hz, 1H), 4.75 (s, 1H), 3.78 (s, 3H), 3.63 (s, 3H), 3.47 (s, 3H), 3.05-3.01 (m, 3H), 2.96 (d, J=5.8 Hz, 1H), 2.58 (s, 3H), 2.26 (s, 3H), 1.96-1.89 (m, 1H), 1.28 (s, 3H), 1.26 (s, 3H) ppm; $^{13}$C NMR (CDCl$_3$, 150 MHz) δ=209.3, 169.0, 163.5, 150.9, 142.1, 141.3, 135.1, 130.0, 115.8, 113.1, 112.6, 109.6, 103.9, 100.9, 99.7, 71.1, 69.3, 69.1, 60.8, 56.8, 56.2, 48.0, 41.5, 35.6, 25.1, 25.0, 21.8, 20.3, 19.6 ppm.

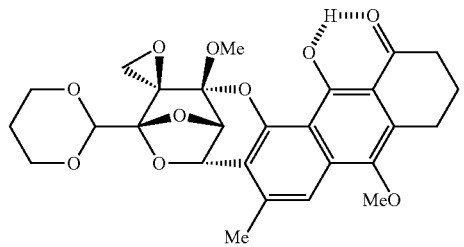

KCN-Trox8:

R$_f$=0.77 (silica gel, EtOAc:hexanes 1:1); [α]$^{25}$$_D$=+268.8 (c=0.08, CH$_2$Cl$_2$); FT-IR (neat): ν$_{max}$=2920, 1620, 1570, 1445, 1389, 1236, 1180, 1094, 1074, 1014, 918 cm$^{-1}$; $^1$H NMR (CDCl$_3$, 600 MHz) δ=14.80 (s, 1H), 7.43 (s, 1H), 5.26 (d, J=4.1 Hz, 1H), 5.08 (s, 1H), 4.84 (d, J=4.2 Hz, 1H), 4.29 (dd, J=4.8, 11.4 Hz, 1H), 4.12 (dd, J=4.8, 11.4 Hz, 1H), 3.89 (dt, J=3.0, 12.6 Hz, 1H), 3.80-3.76 (m, 4H), 3.74 (s, 3H), 3.08-2.99 (m, 1H), 2.96 (d, J=6.0 Hz, 1H), 2.87 (d, J=5.4 Hz, 1H), 2.73 (t, J=6.6 Hz, 2H), 2.61 (s, 3H), 2.26-2.17 (m, J=1H), 2.11-2.07 (m, J=2H), 1.37 (d, J=13.7 Hz, 1H) ppm; $^{13}$C NMR (CDCl$_3$, 150 MHz) δ=204.4, 163.01, 151.5, 142.4, 142.0, 135.2, 130.2, 115.6, 113.2, 113.2, 111.0, 103.1, 102.0, 96.3, 71.5, 69.2, 69.0, 67.5, 67.4, 60.9, 52.8, 38.8, 25.6, 23.6, 22.1, 20.7 ppm.

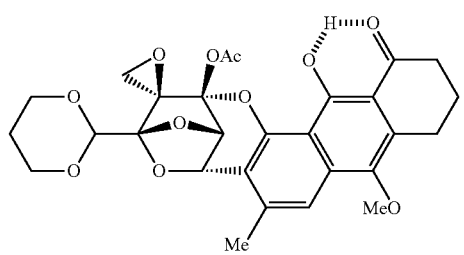

KCN-Trox9:

[α]$^{25}$$_D$=+181.8 (c=0.11, CH$_2$Cl$_2$); FT-IR (neat): ν$_{max}$=2923, 1767, 1621, 1571, 1445, 1389, 1347, 1234, 1212, 1180, 1097, 1010, 984, 923, 876 cm$^{-1}$; $^1$H NMR (CDCl$_3$, 600 MHz) δ=14.80 (s, 1H), 7.44 (s, 1H), 5.62 (d, J=4.1 Hz, 1H), 5.30 (d, J=4.1 Hz, 1H), 5.08 (s, 1H), 4.30 (dd, J=2.4, 11.8 Hz, 1H), 4.15 (dd, J=4.9, 11.5 Hz, 1H), 3.90 (dt, J=2.5, 12.2 Hz, 1H), 3.79 (dt, J=2.5, 12.1 Hz, 1H), 3.76 (s, 3H), 3.74 (s, 3H), 3.03-2.98 (m, 4H), 2.70 (t, J=6.4 Hz, 2H), 2.60 (s, 3H), 2.26 (s, 3H), 2.25-2.19 (m, J=1H), 2.09-2.05 (m, J=2H), 1.39 (d, J=13.6 Hz, 1H) ppm; $^{13}$C NMR (CDCl$_3$, 150 MHz) δ=204.3, 168.9, 163.0, 151.0, 142.3, 141.7, 135.3, 130.3, 116.0, 113.0, 112.7, 111.1, 102.6, 110.8, 96.3, 71.2, 69.5, 69.0, 67.5, 67.4, 60.9, 48.0, 38.8, 25.5, 23.6, 22.1, 21.8, 20.6 ppm.

Example 4—¹H and ¹³C NMR Structural Comparison to Švenda, et al

Comparison of ¹H and ¹³C NMR Spectroscopic Data of Keto Epoxide 30 (Švenda, et al. and Herein)

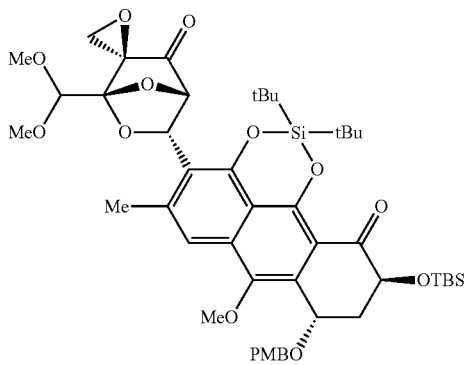

30

TABLE 1a

Comparison of ¹H NMR spectroscopic data

| Data from Švenda, et al. (CDCl₃, 500 MHz) | Data from this work (CDCl₃, 600 MHz) | Δδ (ppm) |
|---|---|---|
| 7.33 (s, 1 H) | 7.33 (s, 1 H) | 0.00 |
| 7.29 (d, J = 8.5 Hz, 2 H) | 7.29 (d, J = 8.5 Hz, 2 H) | 0.00 |
| 6.86 (d, J = 9.0 Hz, 2 H) | 6.86 (d, J = 8.5 Hz, 2 H) | 0.00 |
| 5.62 (d, J = 4.0 Hz, 1 H) | 5.62 (d, J = 3.8 Hz, 1 H) | 0.00 |
| 5.44 (d, J = 4.0 Hz, 1 H) | 5.45 (d, J = 3.8 Hz, 1 H) | −0.01 |
| 5.19 (dd, J = 3.0, 2.5 Hz, 1 H) | 5.19 (brs, 1 H) | 0.00 |
| 4.86 (dd, J = 12.0, 5.0 Hz, 1 H) | 4.88-4.85 (m, 2H) | — |
| 4.85 (s, 1 H) | | |
| 4.70 (d, J = 10.5 Hz, 1 H) | 4.70 (d, J = 10.9 Hz, 1 H) | 0.00 |
| 4.60 (d, J = 11.0 Hz, 1 H) | 4.60 (d, J = 10.9 Hz, 1 H) | 0.00 |
| 3.87 (s, 3 H) | 3.87 (s, 3H) | 0.00 |
| 3.79 (s, 3 H) | 3.79 (s, 3 H) | 0.00 |
| 3.69 (s, 3 H) | 3.69 (s, 3 H) | 0.00 |
| 3.58 (s, 3 H) | 3.58 (s, 3 H) | 0.00 |
| 3.39 (d, J = 7.0 Hz, 1 H) | 3.39 (d, J = 6.4 Hz, 1 H) | 0.00 |
| 3.10 (d, J = 6.0 Hz, 1 H) | 3.10 (d, J = 6.4 Hz, 1 H) | 0.00 |
| 2.74-2.70 (m, 1 H) | 2.74-2.70 (m, 1 H) | 0.00 |
| 2.59 (s, 3 H) | 2.59 (s, 3 H) | 0.00 |
| 2.16-2.10 (m, 1 H) | 2.15-2.11 (m, 1 H) | — |
| 1.17 (s, 9 H) | 1.17 (s, 9 H) | 0.00 |
| 1.09 (s, 9 H) | 1.09 (s, 9 H) | 0.00 |
| 0.95 (s, 9 H) | 0.95 (s, 9 H) | 0.00 |
| 0.23 (s, 3 H) | 0.23 (s, 3 H) | 0.00 |
| 0.13 (s, 3 H) | 0.13 (s, 3 H) | 0.00 |

TABLE 1b

Comparison of ¹³C NMR spectroscopic data

| Data from Švenda, et al. (CDCl₃, 125 MHz) | Data from this work (CDCl₃, 150 MHz) | Δδ (ppm) |
|---|---|---|
| 202.1 | 202.1 | 0.0 |
| 194.5 | 194.5 | 0.0 |
| 159.3 | 159.2 | 0.1 |
| 150.3 | 150.3 | 0.0 |
| 149.1 | 149.1 | 0.0 |
| 146.1 | 146.1 | 0.0 |
| 138.8 | 138.8 | 0.0 |
| 131.0 | 131.0 | 0.0 |
| 130.3 | 130.2 | 0.1 |
| 129.7 | 129.7 | 0.0 |
| 129.6 | 129.6 | 0.0 |
| 118.0 | 118.0 | 0.0 |
| 117.1 | 117.1 | 0.0 |
| 115.3 | 115.3 | 0.0 |
| 114.6 | 114.6 | 0.0 |
| 113.8 | 113.8 | 0.0 |
| 107.5 | 107.5 | 0.0 |
| 99.9 | 99.9 | 0.0 |
| 82.0 | 82.0 | 0.0 |
| 78.0 | 78.0 | 0.0 |
| 71.3 | 71.3 | 0.0 |
| 71.1 | 71.1 | 0.0 |
| 69.7 | 69.7 | 0.0 |
| 62.8 | 62.7 | 0.1 |
| 61.8 | 61.8 | 0.0 |
| 57.1 | 57.1 | 0.0 |
| 56.2 | 56.2 | 0.0 |
| 55.3 | 55.3 | 0.0 |
| 50.1 | 50.1 | 0.0 |
| 36.4 | 36.4 | 0.0 |
| 26.3 | 26.2 | 0.1 |
| 26.2 | 26.2 | 0.0 |
| 26.0 | 26.0 | 0.0 |
| 23.8 | 23.8 | 0.0 |
| 21.5 | 21.5 | 0.0 |
| 20.9 | 20.8 | 0.1 |
| 18.7 | 18.7 | 0.0 |
| −4.3 | −4.3 | 0.0 |
| −5.4 | −5.4 | 0.0 |

Comparison of ¹H and ¹³C NMR Spectroscopic Data of Hemiacetal 31 (Švenda, et al. and Herein)

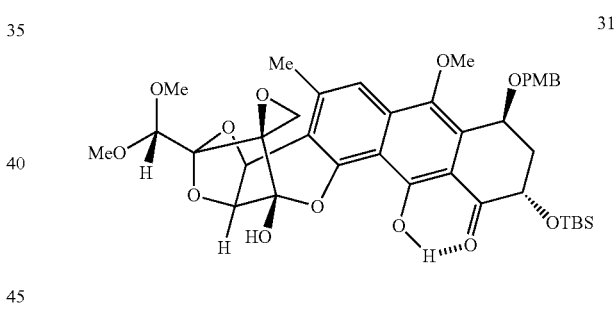

31

TABLE 2a

Comparison of ¹H NMR spectroscopic data

| Data from Švenda, et al. (CDCl₃, 500 MHz) | Data from this work (CDCl₃, 600 MHz) | Δδ (ppm) |
|---|---|---|
| 14.81 (s, 1 H) | 14.78 (s, 1 H) | 0.03 |
| 7.47 (s, 1 H) | 7.41 (s, 1 H) | 0.06 |
| 7.28 (d, J = 8.5 Hz, 2 H) | 7.27 (d, J = 8.6 Hz, 2 H) | 0.01 |
| 6.87 (d, J = 9.0 Hz, 2 H) | 6.86 (d, J = 8.6 Hz, 2 H) | 0.01 |
| 5.26 (d, J = 4.0 Hz, 1 H) | 5.25 (d, J = 4.0 Hz, 1 H) | 0.01 |
| 5.18 (dd, J = 3.0, 2.0 Hz, 1 H) | 5.16 (t, J = 2.5 Hz, 1 H) | 0.02 |
| 4.95 (dd, J = 12.5, 5.0 Hz, 1 H) | 4.94 (dd, J = 12.4, 5.1 Hz, 1 H) | 0.01 |
| 4.84 (d, J = 4.0 Hz, 1 H) | 4.88 (d, J = 4.0 Hz, 1 H) | −0.04 |
| 4.69 (d, J = 10.5 Hz, 1 H) | 4.69 (d, J = 11.0 Hz, 1 H) | 0.00 |
| 4.70 (s, 1 H) | 4.69 (s, 1 H) | 0.01 |
| 4.58 (d, J = 11.5 Hz, 1 H) | 4.58 (d, J = 11.0 Hz, 1 H) | 0.00 |
| 4.31 (s, 1 H) | 4.48 (s, 1 H) | −0.17 |
| 3.83 (s, 3 H) | 3.81 (s, 3 H) | 0.02 |
| 3.80 (s, 3 H) | 3.79 (s, 3 H) | 0.01 |
| 3.62 (s, 3 H) | 3.61 (s, 3 H) | 0.01 |
| 3.46 (s, 3 H) | 3.46 (s, 3 H) | 0.00 |
| 2.98 (d, J = 5.5 Hz, 1 H) | 2.95 (d, J = 5.3 Hz, 1 H) | 0.03 |

TABLE 2a-continued

Comparison of $^1$H NMR spectroscopic data

| Data from Švenda, et al. (CDCl$_3$, 500 MHz) | Data from this work (CDCl$_3$, 600 MHz) | Δδ (ppm) |
|---|---|---|
| 2.74-2.69 (m, 1 H) | 2.71 (ddd, J = 13.4, 5.0, 3.4 Hz, 1 H) | — |
| 2.60 (s, 3 H) | 2.57 (s, 3 H) | 0.03 |
| 2.20-2.15 (m, 1 H) | 2.18 (dt, J = 13.4, 2.3 Hz, 1 H) | — |
| 0.96 (s, 9 H) | 0.96 (s, 9 H) | 0.00 |
| 0.23 (s, 3 H) | 0.23 (s, 3 H) | 0.00 |
| 0.16 (s, 3 H) | 0.16 (s, 3 H) | 0.00 |

TABLE 2b

Comparison of $^{13}$C NMR spectroscopic data

| Data from Švenda, et al. (CDCl$_3$, 125 MHz) | Data from this work (CDCl$_3$, 150 MHz) | Δδ (ppm) |
|---|---|---|
| 203.2 | 203.3 | −0.1 |
| 162.6 | 162.6 | 0.0 |
| 159.3 | 159.3 | 0.0 |
| 151.3 | 151.4 | −0.1 |
| 144.0 | 144.1 | −0.1 |
| 141.8 | 141.8 | 0.0 |
| 135.0 | 135.1 | −0.1 |
| 130.1 | 130.0 | 0.1 |
| 129.5 | 129.5 | 0.0 |
| 127.5 | 127.6 | −0.1 |
| 116.3 | 116.4 | −0.1 |
| 114.8 | 114.9 | −0.1 |
| 114.7 | 114.6 | 0.1 |
| 113.8 | 113.9 | −0.1 |
| 108.5 | 108.6 | −0.1 |
| 103.8 | 103.8 | 0.0 |
| 100.1 | 100.1 | 0.0 |
| 98.5 | 98.5 | 0.0 |
| 73.2 | 73.2 | 0.0 |
| 70.9 | 70.9 | 0.0 |
| 69.7 | 69.7 | 0.0 |
| 69.2 | 69.3 | −0.1 |
| 69.2 | 69.2 | 0.0 |
| 68.9 | 68.9 | 0.0 |
| 62.7 | 62.7 | 0.0 |
| 56.9 | 57.0 | −0.1 |
| 56.6 | 56.7 | −0.1 |
| 55.2 | 55.3 | −0.1 |
| 50.3 | 50.4 | −0.1 |
| 36.1 | 36.2 | −0.1 |
| 25.9 | 25.9 | 0.0 |
| 20.4 | 20.4 | 0.0 |
| 18.6 | 18.6 | 0.0 |
| −4.4 | −4.4 | 0.0 |
| −5.4 | −5.4 | 0.0 |

Comparison of $^1$H and $^{13}$C NMR Spectroscopic Data of DC-45-A2 (Švenda, et al. and Herein)

TABLE 3a

Comparison of $^1$H NMR spectroscopic data

| Data from Švenda, et al. (CDCl$_3$, 500 MHz) | Data from this work (CDCl$_3$, 600 MHz) | Δδ (ppm) |
|---|---|---|
| 13.99 (s, 1 H) | 14.00 (s, 1 H) | −0.01 |
| 7.43 (s, 1 H) | 7.46 (s, 1 H) | −0.03 |
| 5.45 (s, 1 H) | 5.45 (s, 1 H) | 0.00 |
| 5.25 (d, J = 3.6 Hz, 1 H) | 5.26 (d, J = 3.9 Hz, 1 H) | −0.01 |
| 4.91 (dd, J = 12.6, 4.8 Hz, 1 H) | 4.92 (dd, J = 12.6, 5.2 Hz, 1 H) | −0.01 |
| 4.85 (d, J = 3.6 Hz, 1 H) | 4.84 (d, J = 3.8 Hz, 1 H) | 0.01 |
| 4.71 (s, 1 H) | 4.71 (s, 1 H) | 0.00 |
| 4.58 (br s, 1 H) | — | — |
| 3.92 (s, 3 H) | 3.92 (s, 3 H) | 0.00 |
| 3.62 (s, 3 H) | 3.62 (s, 3 H) | 0.00 |
| 3.47 (s, 3 H) | 3.47 (s, 3 H) | 0.00 |
| 3.13 (d, J = 4.8 Hz, 1 H) | 3.15 (d, J = 5.4 Hz, 1 H) | −0.02 |
| 3.02 (d, J = 5.4 Hz, 1 H) | 3.03 (d, J = 5.4 Hz, 1 H) | −0.01 |
| 2.74-2.70 (m, 1 H) | 2.74-2.70 (m, 1 H) | — |
| 2.61 (s, 3 H) | 2.62 (s, 3 H) | −0.01 |
| 2.33 (br s, 1 H) | — | — |
| 2.21-2.17 (m, 1 H) | 2.21-2.16 (m, 1 H) | — |

TABLE 3b

Comparison of $^{13}$C NMR spectroscopic data

| Data from Švenda, et al. (CDCl$_3$, 125 MHz) | Data from this work (CDCl$_3$, 150 MHz) | Δδ (ppm) |
|---|---|---|
| 203.3 | 203.2 | 0.1 |
| 162.2 | 162.3 | −0.1 |
| 151.6 | 151.7 | −0.1 |
| 144.4 | 144.4 | 0.0 |
| 142.6 | 142.7 | −0.1 |
| 135.6 | 135.7 | −0.1 |
| 129.3 | 129.4 | −0.1 |
| 116.3 | 116.4 | −0.1 |
| 115.0 | 115.0 | 0.0 |
| 114.5 | 114.7 | −0.2 |
| 107.2 | 107.1 | 0.1 |
| 103.9 | 103.9 | 0.0 |
| 100.1 | 100.1 | 0.1 |
| 98.7 | 98.6 | 0.0 |
| 73.3 | 73.2 | 0.1 |
| 69.5 | 69.6 | −0.1 |
| 69.2 | 69.3 | −0.1 |
| 67.7 | 67.7 | 0.0 |
| 62.9 | 62.8 | 0.1 |
| 61.8 | 61.9 | −0.1 |
| 57.0 | 57.0 | 0.0 |
| 56.6 | 56.7 | −0.1 |
| 50.3 | 50.5 | −0.2 |
| 37.0 | 36.9 | 0.1 |
| 20.5 | 20.5 | 0.0 |

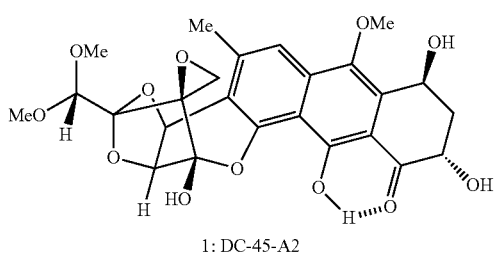

1: DC-45-A2

Example 5—Biological Activity

A. Cytotoxicity Assay

Cells were cultured in a T75 flask to ~50-80% confluency and harvested with trypsin into a single cell suspension. Five hundred (500) cells per well were seeded in tissue culture plates in 50 µL/well culture media and incubated at 37° C. for 18-24 hours. Compounds were diluted as 400× final desired concentrations in DMSO. Serial dilutions in DMSO were then diluted in culture media for a final DMSO concentration of 0.25% and 50 µL/well of the final dilution was added to the cells (Vf=100 µL). Upon plating and treatment, cells were returned to the incubator for an additional 72 hours. CellTiter-Glo reagent was prepared per manufacturer's instructions and added at 100 µL/well to the cultures. CellTiter-Glo allows for relative enumeration of metabolically active cells by quantifying intracellular ATP concentrations. After 5 minutes of incubation with CellTiter-Glo at ambient room temperature, 125 μL/well of the Cell Titer Glo/cell lysate solution was transferred into black assay plates, which were then read in a luminometer within 30 minutes. Luminescence readings obtained from cultures that did not receive any treatment (cell culture media only) were set as 100% control and all other luminescence values were normalized to these controls (e.g., Normalized RLU, relative luminescence unit).

B. Cell Lines Used in the Assay

MES SA and MES SA/Dx cells are uterine sarcoma. MES SA Dx cell line was generated from MES SA to achieve upregulation of MDR1. MES-SA/Dx cells exhibit marked cross-resistance to a number of chemotherapeutic agents (including daunorubicin, dactinomycin, vincristine, taxol, colchicine) and moderate cross-resistance to mitomycin C and melphalan. 293T cells are a human embryonic kidney cell line.

C. Activity Results

The results of the assay are shown in FIGS. 3A-3C and 4A-4C and Table 4 below. In these assays, Trox8 showed 530 pM activity in the MES SA assay, 380 pM in the MES SA DX assay, and 550 pM activity in the 293T assay. Additionally, Trox5, Trox7, and Trox9 also showed good nanomolar cytotoxicity.

TABLE 4

Biological Activity of Trox4-Trox9

| Compound ID | MES SA IC$_{50}$ nM | MES SA DX IC$_{50}$ nM | 293T IC$_{50}$ nM |
|---|---|---|---|
| 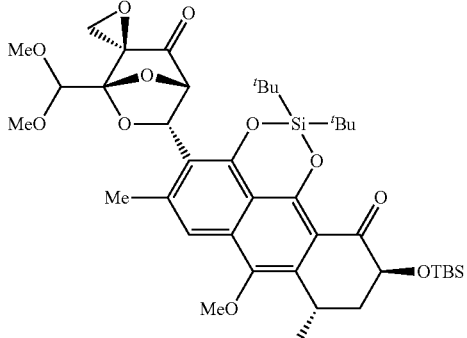 KCN-Triox1 | n/a | | |
| 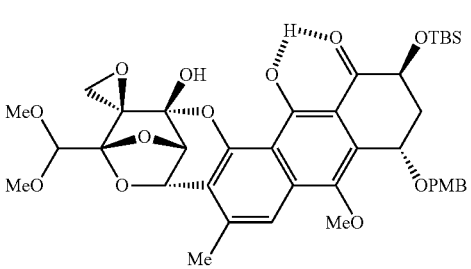 KCN-Triox2 | n/a | | |
| 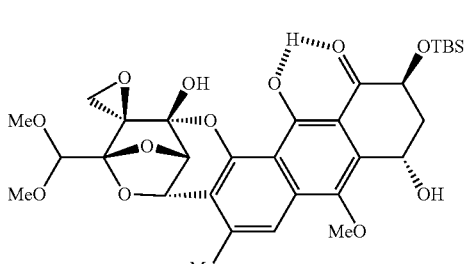 KCN-Triox3 | n/a | | |

TABLE 4-continued
Biological Activity of Trox4-Trox9
| Compound ID | MES SA IC$_{50}$ nM | MES SA DX IC$_{50}$ nM | 293T IC$_{50}$ nM |
|---|---|---|---|
| 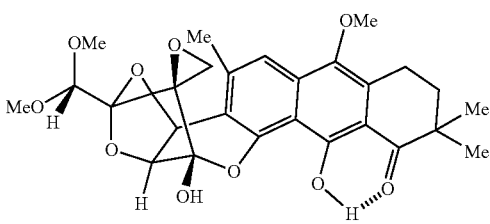 KCN-Triox4 | >1000 | >1000 | >1000 |
| 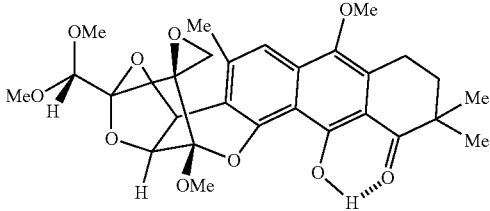 KCN-Triox5 | 562.4 | 213 | 786.2 |
| 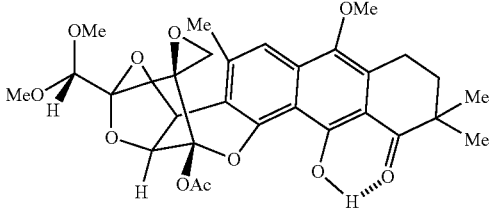 KCN-Triox6 | >1000 | >1000 | >1000 |
| 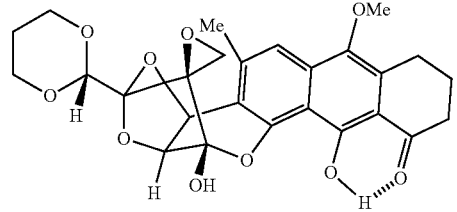 KCN-Triox7 | 3.72 | 5.72 | 2.46 |
| 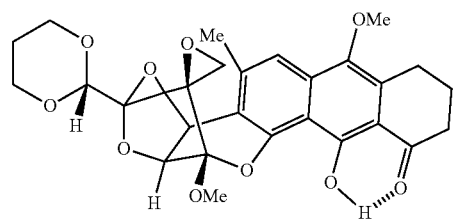 KCN-Triox8 | 0.53 | 0.38 | 0.55 |

TABLE 4-continued
| | Biological Activity of Trox4-Trox9 | | |
|---|---|---|---|
| Compound ID | MES SA IC$_{50}$ nM | MES SA DX IC$_{50}$ nM | 293T IC$_{50}$ nM |
| KCN-Triox9 | 6.109 | 17.42 | 6.89 |
| KCN-Triox10 | | | |
| KCN-Triox11 | | | |
| KCN-triox12 | 18.08 | >1000 | 14.89 |
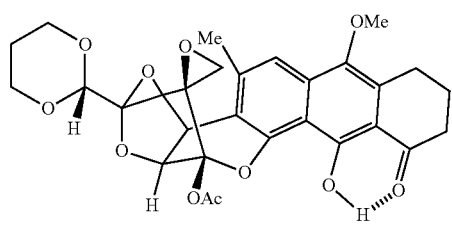
KCN-Triox9
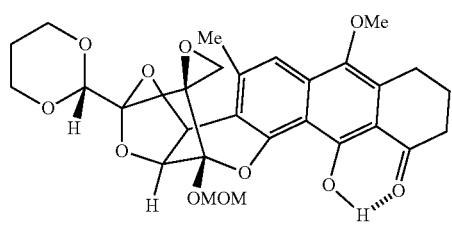
KCN-Triox10
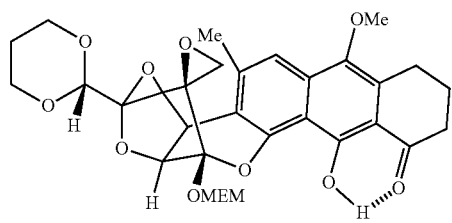
KCN-Triox11
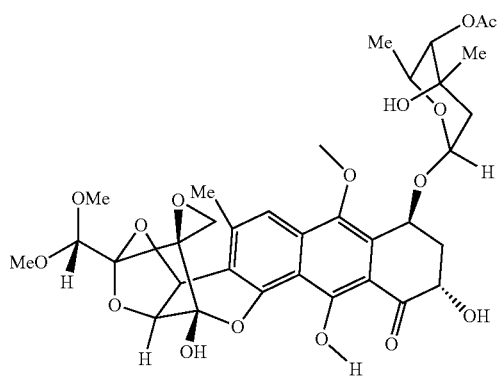
KCN-triox12

TABLE 4-continued
Biological Activity of Trox4-Trox9
| Compound ID | MES SA IC$_{50}$ nM | MES SA DX IC$_{50}$ nM | 293T IC$_{50}$ nM |
|---|---|---|---|
| 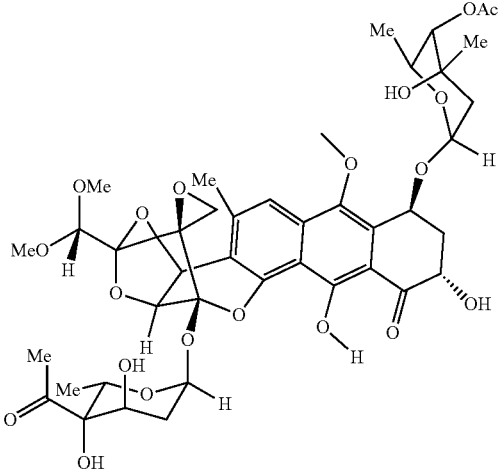<br>KCN-triox13 | 0.74 | 203.5 | 0.702 |
| 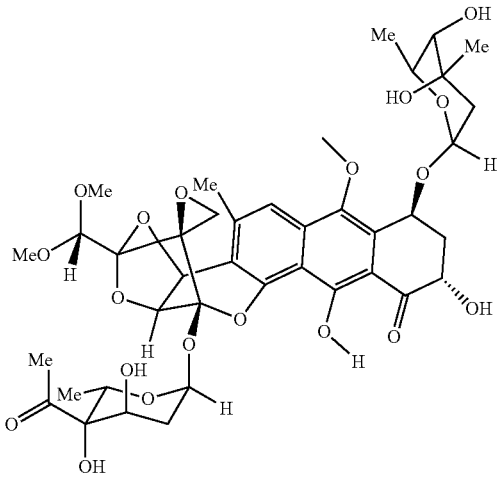<br>KCN-triox14 | 11.06 | >1000 | 8.016 |
| 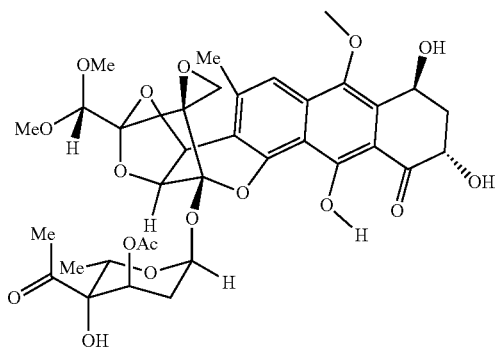<br>KCN-triox15 | 157.4 | >1000 | 95.44 |

TABLE 4-continued
Biological Activity of Trox4-Trox9
| Compound ID | MES SA IC$_{50}$ nM | MES SA DX IC$_{50}$ nM | 293T IC$_{50}$ nM |
|---|---|---|---|
| KCN-triox16 | 2.02 | >1000 | 2.815 |
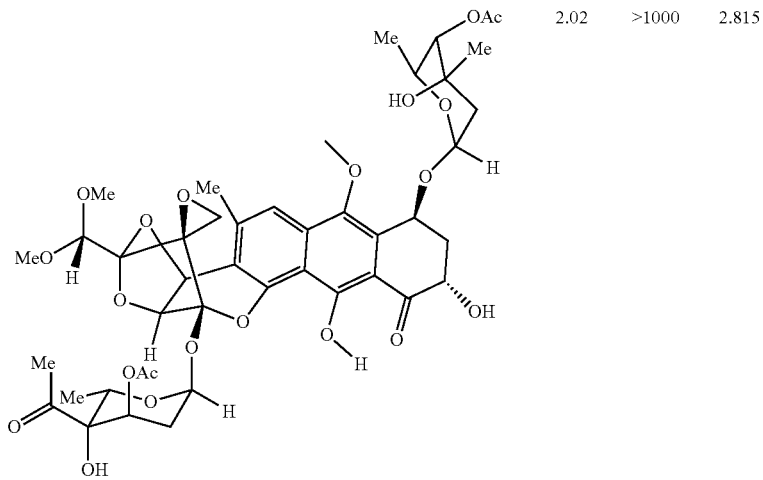
KCN-triox16
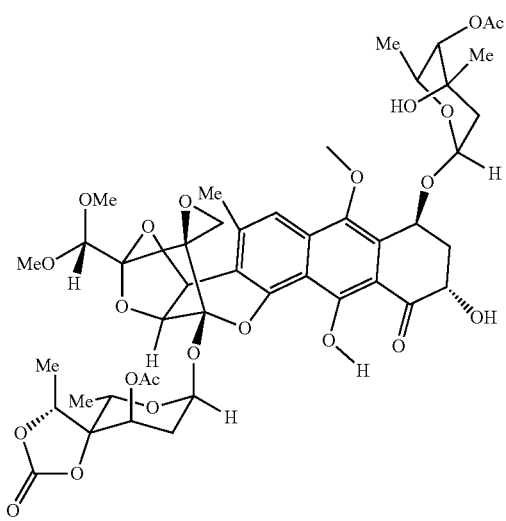
KCN-Triox17

TABLE 4-continued
Biological Activity of Trox4-Trox9
| Compound ID | MES SA IC$_{50}$ nM | MES SA DX IC$_{50}$ nM | 293T IC$_{50}$ nM |
|---|---|---|---|
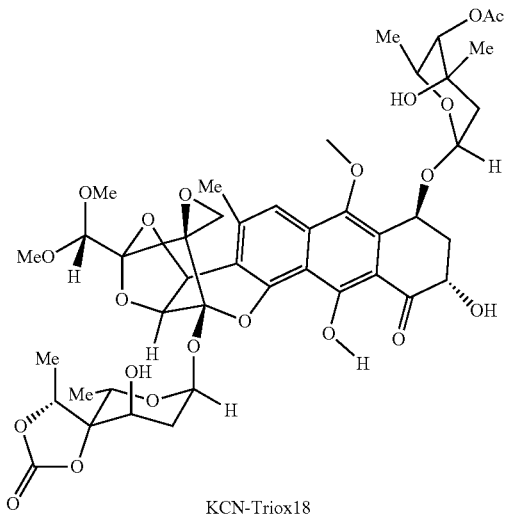
KCN-Triox18
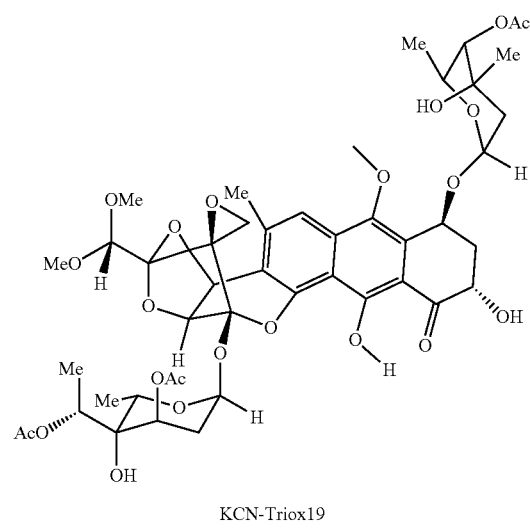
KCN-Triox19

TABLE 4-continued
| | Biological Activity of Trox4-Trox9 | | |
|---|---|---|---|
| Compound ID | MES SA IC$_{50}$ nM | MES SA DX IC$_{50}$ nM | 293T IC$_{50}$ nM |
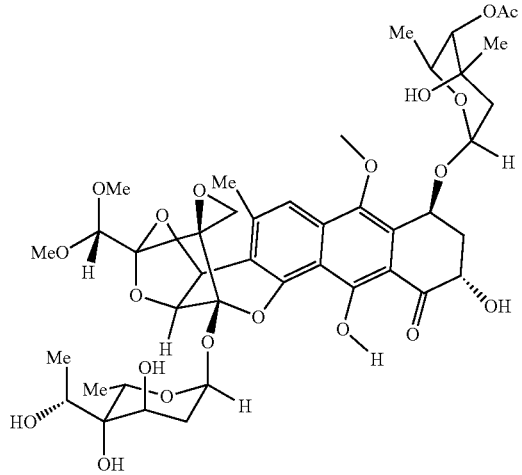
KCN-Triox20
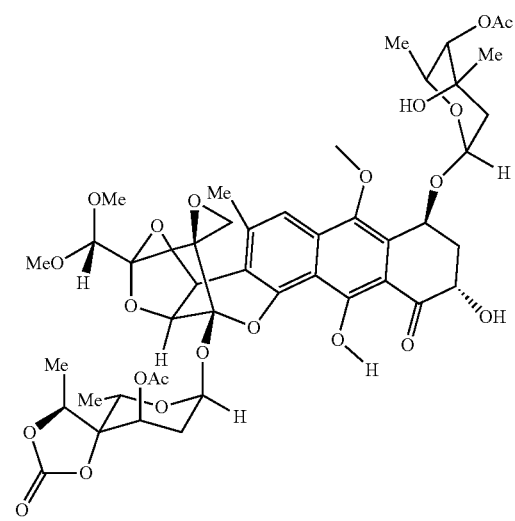
KCN-Triox21

TABLE 4-continued

Biological Activity of Trox4-Trox9

| Compound ID | MES SA IC$_{50}$ nM | MES SA DX IC$_{50}$ nM | 293T IC$_{50}$ nM |
|---|---|---|---|

KCN-Triox22

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference:

Anderson, N. G., *Practical Process Research & Development—A Guide For Organic Chemists*, 2$^{nd}$ ed., Academic Press, New York, 2012.
*March's Advanced Organic Chemistry: Reactions, Mechanisms, and Structure*, 2007.
*Greene's Protective Groups in Organic Chemistry*, Wuts and Greene, Ed., 1973
*Remington's Pharmaceutical Sciences*, 15$^{th}$ Ed., 1035-1038 and 1570-1580, 1990.
*Remington's Pharmaceutical Sciences*, 15$^{th}$ Ed., 3:624-652, 1990.
U.S. Pat. No. 4,459,291
U.S. Pat. No. 5,739,169
U.S. Pat. No. 5,801,005
U.S. Pat. No. 5,824,311
U.S. Pat. No. 5,830,880
U.S. Pat. No. 5,846,945
WO 2003/035065
WO 2011/119549
Banwell et al., *J. Org. Chem.* 1994, 59, 6338-6343.
J. Cassidy et al., *Cancer Chemother. Pharmacol.* 1993, 31, 395-400.
Colman et al., *Tetrahedron: Asymmetry* 1999, 10, 4175-4182.
Davidson et al., *J. Immunotherapy*, 1998, 21(5):389.
de Sousa et al., *Tetrahedron* 2002, 58, 4643-4654.
Evans et al., *J. Am. Chem. Soc.* 1991, 113, 7613-7630.
Fitzner et al., *Anal. Bioanal. Chem.* 2008, 390, 1139-1147.
Gaoni, *J. Chem. Soc.* (C) 1968, 2925-2934.
Hauser et al. *Org. Chem.* 1978, 43, 178-180.
Hoye et al., *Nat. Protoc.* 2007, 10, 2451-2457.
Kato et al., *Tetrahedron* 62, 7307-7318, 2006.
Kraehenbuehl et al., *Tetrahedron Lett.* 1995, 36, 8595-8598;
Kraehenbuehl et al., *Helv. Chim. Acta* 1998, 81, 1439-1479;
Kraus et al., *Tetrahedron Lett.* 1978, 19, 2263-2266.
Pfoh et al., *Nucleic Acids Res.* 2008, 36, 3508-3514.
Magauer et al., *Nat. Chem.* 2013, 5, 886-893.
Maiese et al., *J. Antibiot.* 1990, 43, 253-258.
Maras et al., *J. Org. Chem.* 1998, 63, 2039-2041.
Mango et al., *J. Am. Chem. Soc.* 2005, 127, 6964-6965.
Maskey et al., *J. Antibiot.* 2004, 57, 771-779.
Maskey et al., *Angew. Chem. Int. Ed.* 2004, 43, 1281-1283; *Angew. Chem.* 2004, 116, 1301-1303.
Muthusamy et al., *J. Org. Chem.* 2002, 67, 8019-8033.
Naruse et al., *Tetrahedron* 1988a, 44, 4747-4756.
Naruse et al., *Tetrahedron Lett.* 1988b, 29, 1417-1420.
Nicolaou et al., *J. Am. Chem. Soc.* 2009, 131, 14812-14826.
O'Brien et al., *J. Chem. Soc., Perkin Trans.* 1 1998, 2435-2441.
Padwa et al., *J. Org. Chem.* 1991, 56, 3271-3278.
Pilli et al., *J. Org. Chem.* 1998, 63, 7811-7819.
Pulukuri et al., *Org. Lett.* 2012, 14, 2858-2861.
Smith, et al., *Biochemistry* 1995, 34, 415-425.

Sousa, et al., *Tetrahedron* 2002, 58, 4643-4654.
Sun, et al., *Biochemistry* 1994, 34, 8068-8074.
Švenda, et al., *Proc. Natl. Acad. Sci. U.S.A.* 2011, 108, 6709-6714.
Tomita, et al., *J. Antibiot.* 1981a, 34, 1519-1524.
Tomita, et al., *J. Antibiot.* 1981b, 34, 1525-1530.
Wasserman, et al., *J. Am. Chem. Soc.* 1969, 91, 3674-3675.
Wasserman, et al., *Tetrahedron Lett.* 1986a, 27, 4909-4912.
Wasserman, et al., *Tetrahedron Lett.* 1986b, 27, 4913-4916.
Wasserman, et al., *Tetrahedron Lett.* 1988a, 29, 4973-4976.
Wasserman, et al., *Tetrahedron Lett.* 1988b, 29, 4977-4980.
Yang, et al., *J. Am. Chem. Soc.* 2009, 133, 12433-12435.

What is claimed is:

1. A compound of the formula:

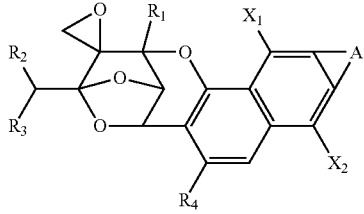

(I)

wherein:
R$_1$ is amino, hydroxy, or mercapto;
alkoxy$_{(C \leq 12)}$, cycloalkoxy$_{(C \leq 12)}$, alkenyloxy$_{(C \leq 12)}$, alkynyloxy$_{(C \leq 12)}$, acyloxy$_{(C \leq 12)}$, alkylthio$_{(C \leq 12)}$, cycloalkylthio$_{(C \leq 12)}$, alkenylthio$_{(C \leq 12)}$, alkynylthio$_{(C \leq 12)}$, acylthio$_{(C \leq 12)}$, alkylamino$_{(C \leq 12)}$, cycloalkylamino$_{(C \leq 12)}$, alkenylamino$_{(C \leq 12)}$, alkynylamino$_{(C \leq 12)}$, dialkylamino$_{(C \leq 12)}$, dicycloalkylamino$_{(C \leq 12)}$, dialkenylamino$_{(C \leq 12)}$, dialkynylamino$_{(C \leq 12)}$, amido$_{(C \leq 12)}$, or a substituted version of any of these groups; or
R$_1$ is a group of the formula: —O-alkanediyl$_{(C \leq 8)}$-alkoxy$_{(C \leq 12)}$, —O-alkanediyl$_{(C \leq 8)}$-alkenyloxy$_{(C \leq 12)}$, —O-alkanediyl$_{(C \leq 8)}$-alkynyloxy$_{(C \leq 12)}$, or a substituted version thereof; or
R$_1$ is a group of the formula:

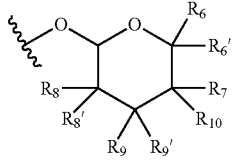

wherein:
R$_6$, R$_6'$, R$_7$, R$_8$, R$_8'$, R$_9$, and R$_9'$ are each independently hydrogen, hydroxy, alkyl$_{(C \leq 8)}$, alkoxy$_{(C \leq 8)}$, acyloxy$_{(C \leq 8)}$, substituted alkyl$_{(C \leq 8)}$, substituted alkoxy$_{(C \leq 8)}$, or substituted acyloxy$_{(C \leq 8)}$; and
R$_{10}$ is hydrogen, hydroxy, alkyl$_{(C \leq 12)}$, alkoxy$_{(C \leq 12)}$, acyl$_{(C \leq 12)}$, substituted alkyl$_{(C \leq 12)}$, substituted alkoxy$_{(C \leq 12)}$, substituted acyl$_{(C \leq 12)}$, or a group of the formula:

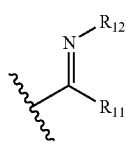

wherein:
R$_{11}$ is hydrogen, alkyl$_{(C \leq 8)}$, or substituted alkyl$_{(C \leq 8)}$; and
R$_{12}$ is hydrogen, hydroxy, alkoxy$_{(C \leq 12)}$, substituted alkoxy$_{(C \leq 12)}$, —O-alkanediyl$_{(C \leq 12)}$-a thiol reactive group, or a substituted version of —O-alkanediyl$_{(C \leq 12)}$-a thiol reactive group; or
R$_7$ and R$_{10}$ are taken together to form a heterocyclic compound of the formula:

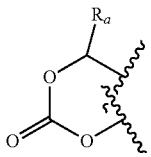

wherein:
R$_a$ is hydrogen, alkyl$_{(C \leq 6)}$, or substituted alkyl$_{(C \leq 6)}$;
R$_2$ and R$_3$ are independently hydrogen, amino, hydroxy, mercapto;
alkyl$_{(C \leq 12)}$, cycloalkyl$_{(C \leq 12)}$, alkenyl$_{(C \leq 12)}$, alkynyl$_{(C \leq 12)}$, or a substituted version of any of these groups;
R$_2$ and R$_3$ are taken together and are alkoxydiyl$_{(C \leq 8)}$, alkylaminodiyl$_{(C \leq 12)}$, alkylthiodiyl$_{(C \leq 12)}$, or a substituted version of any of these groups;
R$_4$ is hydrogen, amino, halo, hydroxy, mercapto, alkyl$_{(C \leq 12)}$ or substituted alkyl$_{(C \leq 12)}$;
X$_1$ and X$_2$ are each independently hydrogen, hydroxy, or alkoxy$_{(C \leq 12)}$, alkenyloxy$_{(C \leq 12)}$, alkynyloxy$_{(C \leq 12)}$, or a substituted version of any of these groups; and
A is a fused cycloalkanediyl and has the structure:

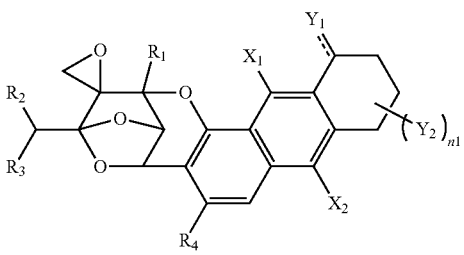

(Ia)

wherein:
Y$_1$ is hydrogen, oxo, alkoxy$_{(C \leq 12)}$, or substituted alkoxy$_{(C \leq 12)}$, provided that when Y$_1$ is oxo, then the atom to which Y$_1$ is bound is part of a double bond, and provided that when the atom to which Y$_1$ is bound is part of a double bond, then Y$_1$ is oxo;
Y$_2$ is hydrogen, hydroxy, alkyl$_{(C \leq 12)}$, substituted alkyl$_{(C \leq 12)}$, alkoxy$_{(C \leq 12)}$, substituted alkoxy$_{(C \leq 12)}$, or —OX$_3$, wherein X$_3$ is a hydroxy protecting group; or a group of the formula:

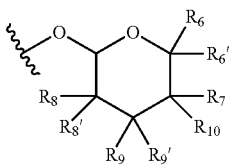

wherein:
R$_6$, R$_6$', R$_7$, R$_8$, R$_8$', R$_9$, and R$_9$' are each independently hydrogen, hydroxy, alkyl$_{(C\leq8)}$, alkoxy$_{(C\leq8)}$, acyloxy$_{(C\leq8)}$, substituted alkyl$_{(C\leq8)}$, substituted alkoxy$_{(C\leq8)}$, or substituted acyloxy$_{(C\leq8)}$; and
R$_{10}$ is hydrogen, hydroxy, alkyl$_{(C\leq12)}$, alkoxy$_{(C\leq12)}$, acyl$_{(C\leq12)}$, substituted alkyl$_{(C\leq12)}$, substituted alkoxy$_{(C\leq12)}$, substituted acyl$_{(C\leq12)}$, or a group of the formula:

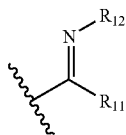

wherein:
R$_{11}$ is hydrogen, alkyl$_{(C\leq8)}$, or substituted alkyl$_{(C\leq8)}$; and
R$_{12}$ is hydrogen, hydroxy, alkoxy$_{(C\leq12)}$, substituted alkoxy$_{(C\leq12)}$, —O-alkanediyl$_{(C\leq12)}$-a thiol reactive group, or a substituted version of —O-alkanediyl$_{(C\leq12)}$-a thiol reactive group; or
R$_7$ and R$_{10}$ are taken together to form a heterocyclic compound of the formula:

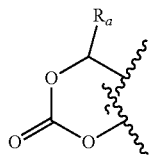

wherein:
R$_a$ is hydrogen, alkyl$_{(C\leq6)}$, or substituted alkyl$_{(C\leq6)}$; and
n$_1$ is 0, 1, 2, 3, 4, 5, or 6; or
or a pharmaceutically acceptable salt thereof.

2. The compound of claim 1 further defined as:

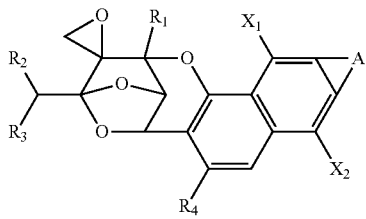

(I)

wherein:
R$_1$ is amino, hydroxy, or mercapto;
alkoxy$_{(C\leq12)}$, cycloalkoxy$_{(C\leq12)}$, alkenyloxy$_{(C\leq12)}$, alkynyloxy$_{(C\leq12)}$, acyloxy$_{(C\leq12)}$, alkylthio$_{(C\leq12)}$, cycloalkylthio$_{(C\leq12)}$, alkenylthio$_{(C\leq12)}$, alkynylthio$_{(C\leq12)}$, acylthio$_{(C\leq12)}$, alkylamino$_{(C\leq12)}$, cycloalkylamino$_{(C\leq12)}$, alkenylamino$_{(C\leq12)}$, alkynylamino$_{(C\leq12)}$, dialkylamino$_{(C\leq12)}$, dicycloalkylamino$_{(C\leq12)}$, dialkenylamino$_{(C\leq12)}$, dialkynylamino$_{(C\leq12)}$, amido$_{(C\leq12)}$, or a substituted version of any of these groups; or
R$_1$ is a group of the formula: —O-alkanediyl$_{(C\leq8)}$-alkoxy$_{(C\leq12)}$, —O-alkanediyl$_{(C\leq8)}$-alkenyloxy$_{(C\leq12)}$, —O-alkanediyl$_{(C\leq8)}$-alkynyloxy$_{(C\leq12)}$, or a substituted version thereof; or R$_1$ is a group of the formula:

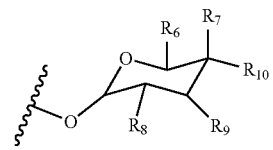

wherein:
R$_6$, R$_7$, R$_8$, and R$_9$ are each independently hydrogen, hydroxy, alkyl$_{(C\leq8)}$, alkoxy$_{(C\leq8)}$, substituted alkyl$_{(C\leq8)}$, or substituted alkoxy$_{(C\leq8)}$; and
R$_{10}$ is hydrogen, hydroxy, alkyl$_{(C\leq12)}$, alkoxy$_{(C\leq12)}$, acyl$_{(C\leq12)}$, substituted alkyl$_{(C\leq12)}$, substituted alkoxy$_{(C\leq12)}$, substituted acyl$_{(C\leq12)}$, or a group of the formula:

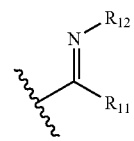

wherein:
R$_{11}$ is hydrogen, alkyl$_{(C\leq8)}$, or substituted alkyl$_{(C\leq8)}$; and
R$_{12}$ is hydrogen, hydroxy, alkoxy$_{(C\leq12)}$, substituted alkoxy$_{(C\leq12)}$, —O-alkanediyl$_{(C\leq12)}$-a thiol reactive group, or a substituted version of —O-alkanediyl$_{(C\leq12)}$-a thiol reactive group;
R$_2$ and R$_3$ are independently hydrogen, amino, hydroxy, mercapto;
alkyl$_{(C\leq12)}$, cycloalkyl$_{(C\leq12)}$, alkenyl$_{(C\leq12)}$, alkynyl$_{(C\leq12)}$, or a substituted version of any of these groups;
R$_2$ and R$_3$ are taken together and are alkoxydiyl$_{(C\leq8)}$, alkylaminodiyl$_{(C\leq12)}$, alkylthiodiyl$_{(C\leq12)}$, or a substituted version of any of these groups;
R$_4$ is hydrogen, amino, halo, hydroxy, mercapto, alkyl$_{(C\leq12)}$ or substituted alkyl$_{(C\leq12)}$;
X$_1$ and X$_2$ are each independently hydrogen, hydroxy, or alkoxy$_{(C\leq12)}$, alkenyloxy$_{(C\leq12)}$, alkynyloxy$_{(C\leq12)}$, or a substituted version of any of these groups; and
A is a fused cycloalkanediyl and has the structure:

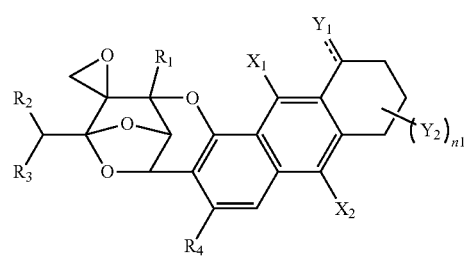

(Ia)

wherein:
Y$_1$ is hydrogen, oxo, alkoxy$_{(C\leq12)}$, or substituted alkoxy$_{(C\leq12)}$, provided that when Y$_1$ is oxo, then the atom to which Y$_1$ is bound is part of a double bond, and provided that when the atom to which Y$_1$ is bound is part of a double bond, then Y$_1$ is oxo;

$Y_2$ is hydrogen, hydroxy, alkyl$_{(C \leq 12)}$, substituted alkyl$_{(C \leq 12)}$, alkoxy$_{(C \leq 12)}$, substituted alkoxy$_{(C \leq 12)}$, or —OX$_3$, wherein X$_3$ is a hydroxy protecting group; and $n_1$ is 0, 1, 2, 3, 4, 5, or 6; or or a pharmaceutically acceptable salt thereof.

3. The compound of claim 1, wherein $R_1$ is:

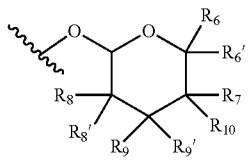

wherein:

$R_6$, $R_6'$, $R_7$, $R_8$, $R_8'$, $R_9$, and $R_9'$ are each independently hydrogen, hydroxy, alkyl$_{(C \leq 8)}$, alkoxy$_{(C \leq 8)}$, acyloxy$_{(C \leq 8)}$, substituted alkyl$_{(C \leq 8)}$, substituted alkoxy$_{(C \leq 8)}$, or substituted acyloxy$_{(C \leq 8)}$; and $R_{10}$ is hydrogen, hydroxy, alkyl$_{(C \leq 12)}$, alkoxy$_{(C \leq 12)}$, acyl$_{(C \leq 12)}$, substituted alkyl$_{(C \leq 12)}$, substituted alkoxy$_{(C \leq 12)}$, substituted acyl$_{(C \leq 12)}$, or a group of the formula:

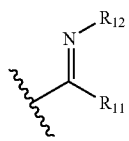

wherein:

$R_{11}$ is hydrogen, alkyl$_{(C \leq 8)}$, or substituted alkyl$_{(C \leq 8)}$; and $R_{12}$ is hydrogen, hydroxy, alkoxy$_{(C \leq 12)}$, substituted alkoxy$_{(C \leq 12)}$, —O-alkanediyl$_{(C \leq 12)}$-a thiol reactive group, or a substituted version of —O-alkanediyl$_{(C \leq 12)}$-a thiol reactive group; or $R_7$ and $R_{10}$ are taken together to form a heterocyclic compound of the formula:

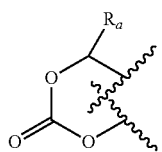

wherein:

$R_a$ is hydrogen, alkyl$_{(C \leq 6)}$, or substituted alkyl$_{(C \leq 6)}$.

4. The compound of claim 1, wherein $R_1$ is alkoxy$_{(C \leq 12)}$ or substituted alkoxy$_{(C \leq 12)}$.

5. The compound of claim 1, wherein $R_2$ and $R_3$ are taken together and is alkoxydiyl$_{(C \leq 12)}$ or substituted alkoxydiyl$_{(C \leq 12)}$.

6. The compound of claim 1, wherein $R_4$ is alkyl$_{(C \leq 12)}$ or substituted alkyl$_{(C \leq 12)}$.

7. The compound of claim 1, wherein $X_1$ or $X_2$ is hydroxy, alkoxy$_{(C \leq 12)}$, or substituted alkoxy$_{(C \leq 12)}$.

8. The compound of claim 1, wherein $Y_1$ is oxo or $Y_2$ is hydroxy or $Y_2$ is:

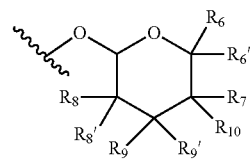

wherein:

$R_6$, $R_6'$, $R_7$, $R_8$, $R_8'$, $R_9$, and $R_9'$ are each independently hydrogen, hydroxy, alkyl$_{(C \leq 8)}$, alkoxy$_{(C \leq 8)}$, acyloxy$_{(C \leq 8)}$, substituted alkyl$_{(C \leq 8)}$, substituted alkoxy$_{(C \leq 8)}$, or substituted acyloxy$_{(C \leq 8)}$; and $R_{10}$ is hydrogen, hydroxy, alkyl$_{(C \leq 12)}$, alkoxy$_{(C \leq 12)}$, acyl$_{(C \leq 12)}$, substituted alkyl$_{(C \leq 12)}$, substituted alkoxy$_{(C \leq 12)}$, substituted acyl$_{(C \leq 12)}$, or a group of the formula:

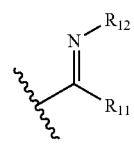

wherein:

$R_{11}$ is hydrogen, alkyl$_{(C \leq 8)}$, or substituted alkyl$_{(C \leq 8)}$; and $R_{12}$ is hydrogen, hydroxy, alkoxy$_{(C \leq 12)}$, substituted alkoxy$_{(C \leq 12)}$, —O-alkanediyl$_{(C \leq 12)}$-a thiol reactive group, or a substituted version of —O-alkanediyl$_{(C \leq 12)}$-a thiol reactive group; or $R_7$ and $R_{10}$ are taken together to form a heterocyclic compound of the formula:

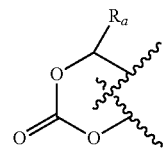

wherein:

$R_a$ is hydrogen, alkyl$_{(C \leq 6)}$, or substituted alkyl$_{(C \leq 6)}$.

9. The compound of claim 1, wherein $n_1$ is 0, 1, 2, or 3, $Y_3$ is hydroxy, alkoxy$_{(C \leq 12)}$, or substituted alkoxy$_{(C \leq 12)}$, $Y_4$ is hydroxy, alkoxy$_{(C \leq 12)}$, or substituted alkoxy$_{(C \leq 12)}$, or $n_2$ is 1, 2, or 3.

10. The compound of claim 1, wherein the compound is further defined as:

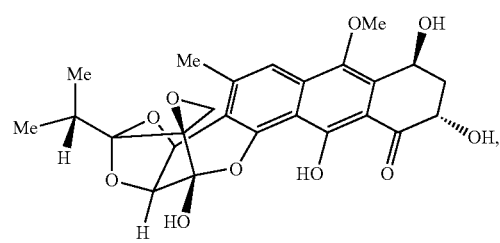

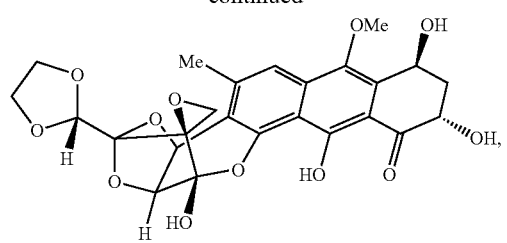
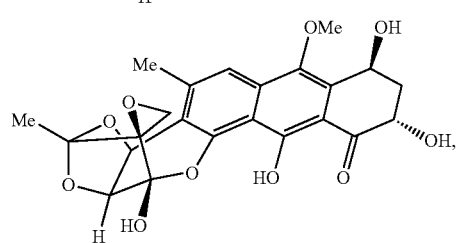
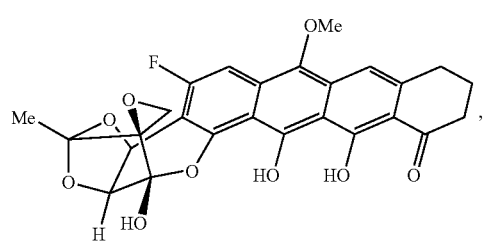
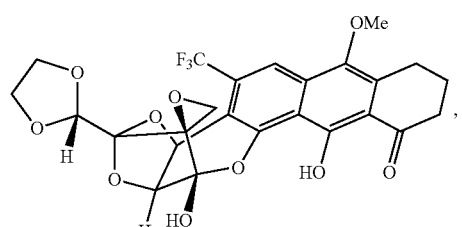
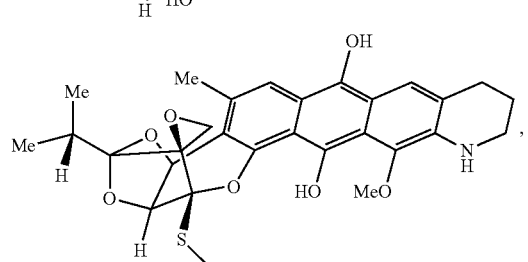
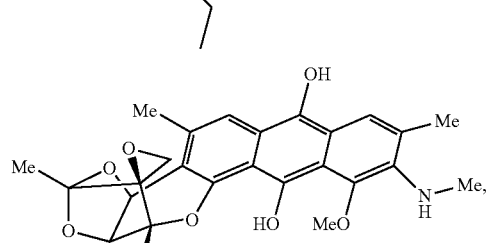
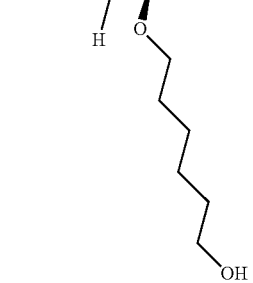
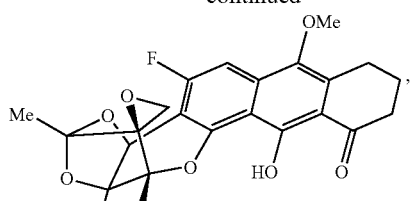
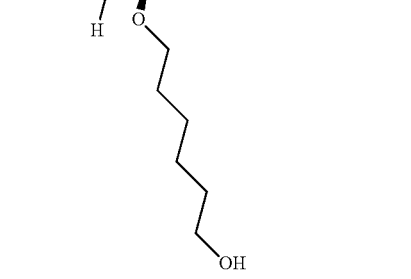
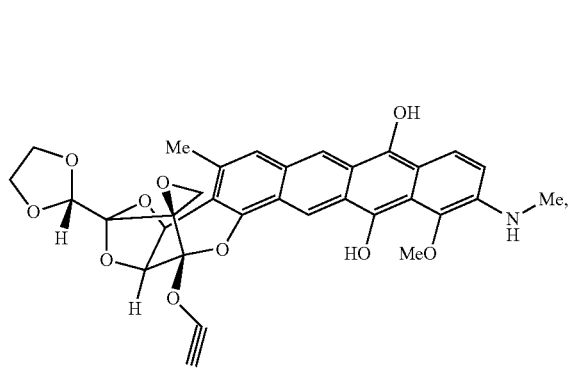
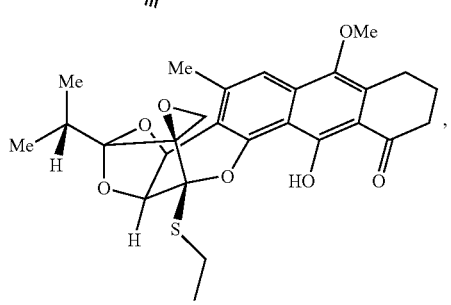
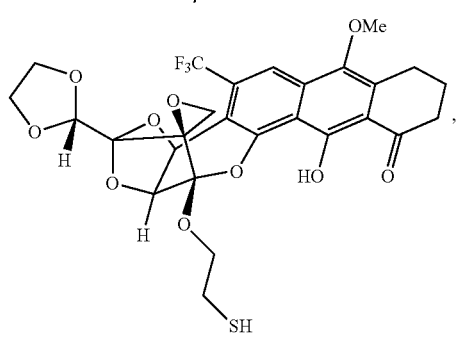
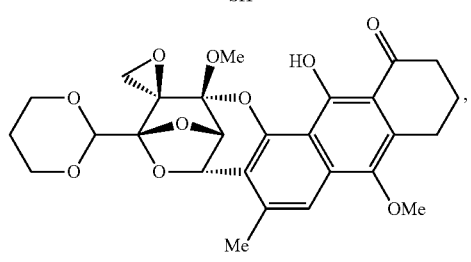

135
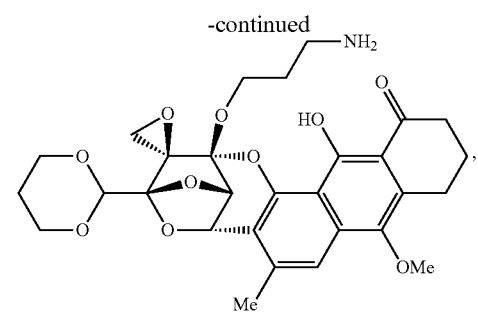
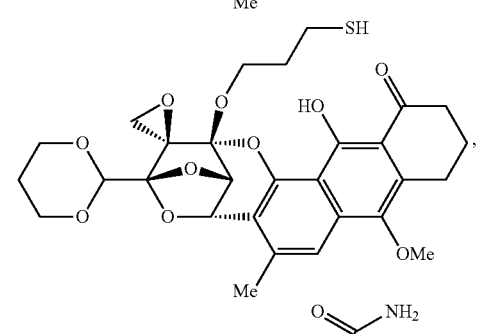
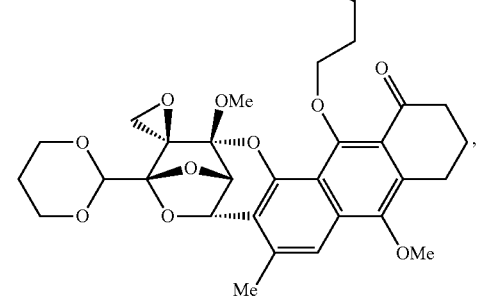
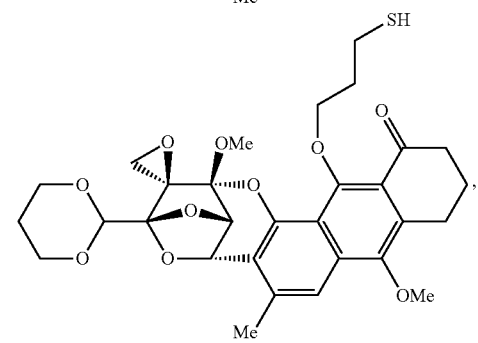
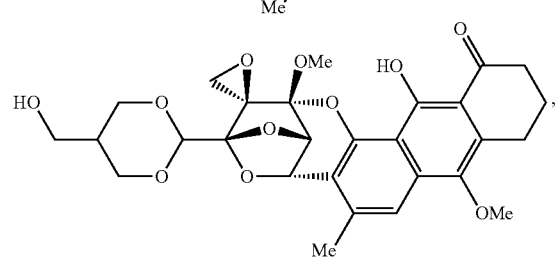
136
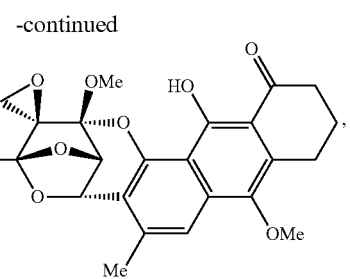
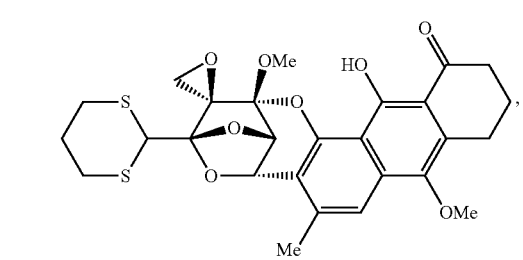
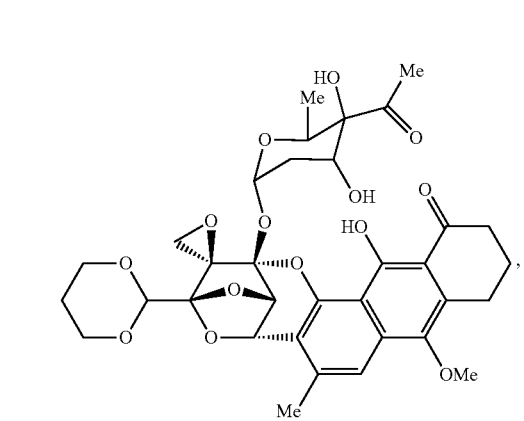
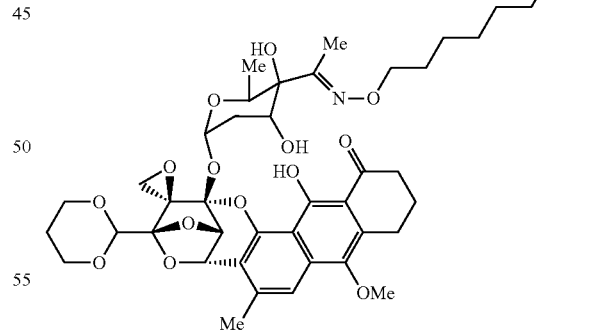
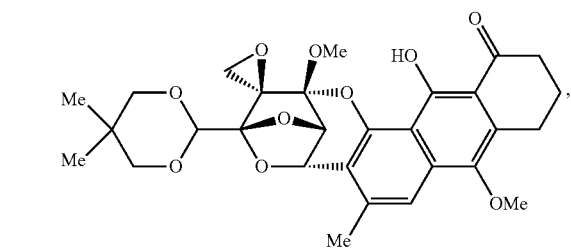

137
-continued
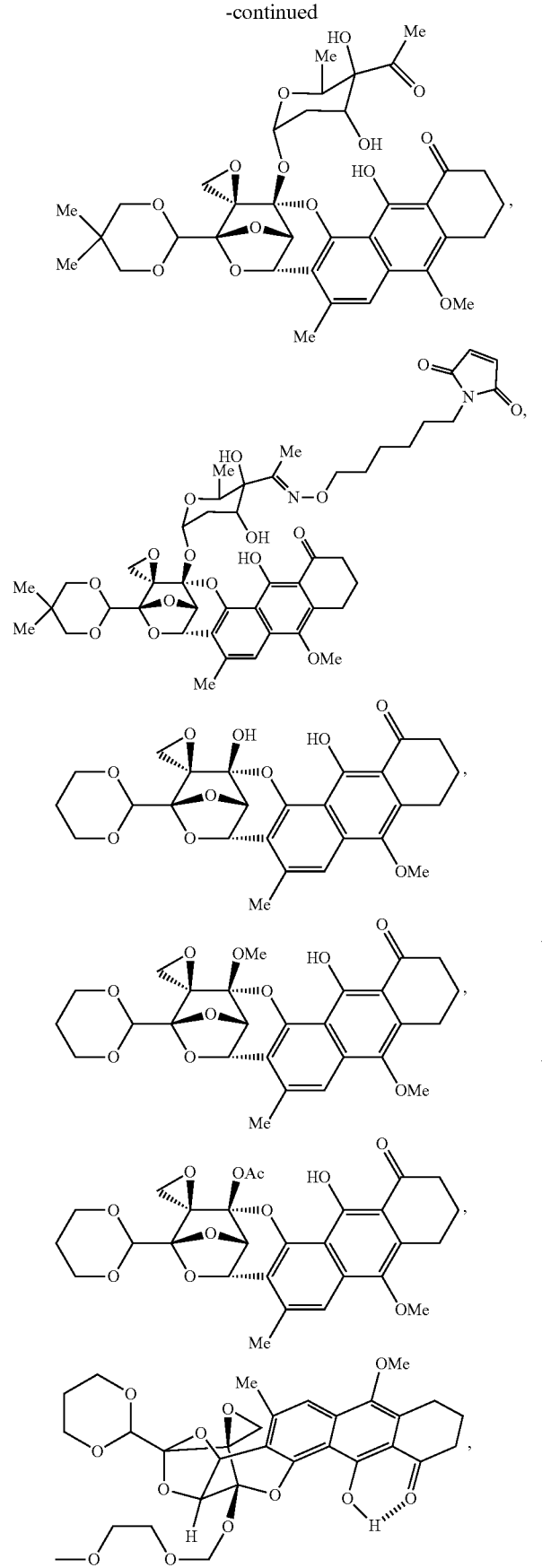
138
-continued
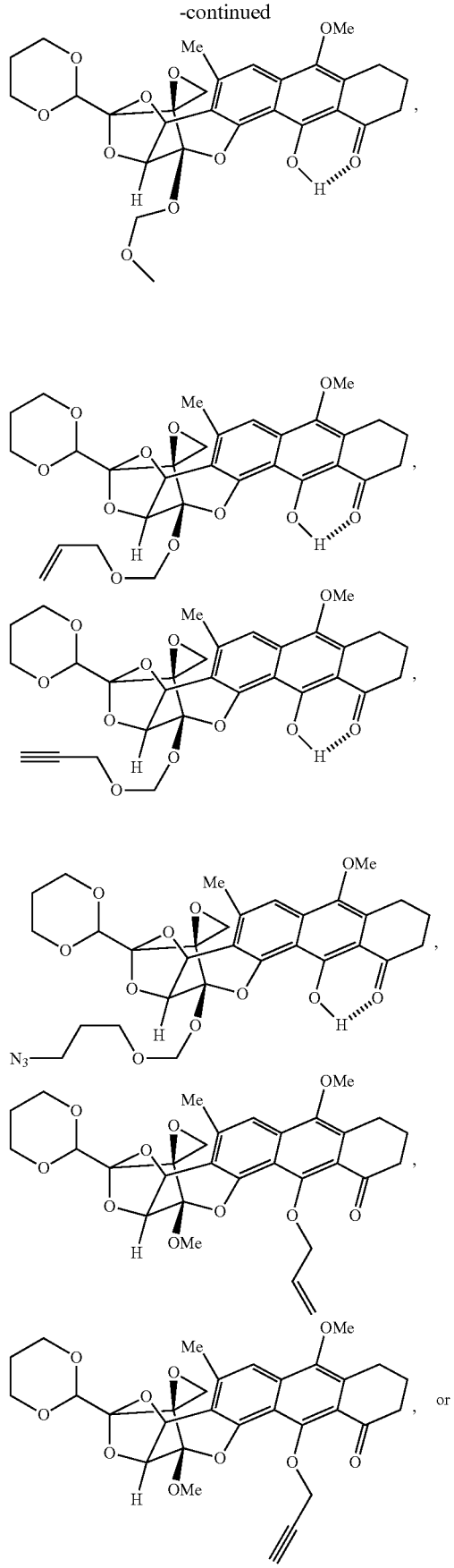

-continued

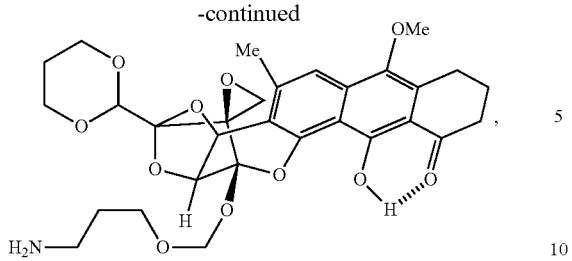
5 or a pharmaceutically acceptable salt thereof.

11. A pharmaceutical composition comprising a compound of claim 1 and a pharmaceutically acceptable carrier.

12. A conjugate of the formula:

$$(A\text{-}L)_n\text{-}X \qquad (VI)$$

wherein:
 A is a compound of claim 1;
 L is a covalent bond or a divalent linker, wherein the divalent linker comprises a group at each end selected from a carbonyl, an amide, an amine, a hydroxy, a mercapto, an aldehyde, and a ketone;
 n is 1, 2, 3, 4, 5, 6, 7, 8, 9, 10, 11, or 12; and
 X is a cell targeting moiety, wherein the cell targeting moiety is an antibody for a specific antigen that is expressed by a cancer cell.

* * * * *